(12) United States Patent
Dean

(10) Patent No.: US 8,486,411 B2
(45) Date of Patent: Jul. 16, 2013

(54) METHODS FOR IDENTIFYING AN EPITOPE OF A POLYPEPTIDE, CHLAMYDIAL ANTIGENIC POLYPEPTIDES IDENTIFIED THEREBY, AND METHODS OF USE THEREOF

(75) Inventor: Deborah Dean, Oakland, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 340 days.

(21) Appl. No.: 12/064,327

(22) PCT Filed: Aug. 29, 2006

(86) PCT No.: PCT/US2006/034118
§ 371 (c)(1),
(2), (4) Date: Sep. 15, 2008

(87) PCT Pub. No.: WO2007/027954
PCT Pub. Date: Mar. 8, 2007

(65) Prior Publication Data
US 2009/0214582 A1    Aug. 27, 2009

Related U.S. Application Data

(60) Provisional application No. 60/713,192, filed on Aug. 30, 2005.

(51) Int. Cl.
*A61K 39/00* (2006.01)
*A61K 39/02* (2006.01)
*C07K 1/00* (2006.01)
*C07K 2/00* (2006.01)

(52) U.S. Cl.
USPC .............. 424/185.1; 424/190.1; 424/192.1; 424/234.1; 530/300; 530/350

(58) Field of Classification Search
None
See application file for complete search history.

(56) References Cited

U.S. PATENT DOCUMENTS

| | | | |
|---|---|---|---|
| 5,759,551 A * | 6/1998 | Ladd et al. ................. | 424/198.1 |
| 5,760,184 A * | 6/1998 | Swain et al. ............... | 530/387.1 |
| 5,869,608 A * | 2/1999 | Caldwell et al. ........... | 530/350 |
| 5,882,645 A * | 3/1999 | Toth et al. .................. | 424/194.1 |
| 2009/0214570 A1 | 8/2009 | Mrsny et al. | |

FOREIGN PATENT DOCUMENTS

WO    WO 2006/125076 A2    11/2006

OTHER PUBLICATIONS

Millman et al. Recombination in the ompA gene but not the omcB gene of Chlamydia contributes to serovar-specific differences in tissue tropism, immune surveillance, and persistence of the organism. (2001) J. Bacteriol. 183:5997-6008.

Montigiani et al. Genomic Approach for Analysis of Surface Proteins in Chlamydia pneumoniae. (2002) Infect. Immunity 70:368-379.

Millman et al. Population-Based Genetic and Evolutionary Analysis of Chlamydia trachomatis Urogenital Strain Variation in the United States. (2004) J. Bacteriol. 186:2457-2465.

Dean, D., et al. Direct sequence evaluation of the major outer membrane protein gene variant regions of Chlamydia trachomatis subtypes D', I', and L2'. Infection and Immunity. 1991, vol. 59, No. 4, pp. 1579-1582.

Dean, D., et al. Molecular and mutation trends analyses of omp1 alleles for serovar E of Chlamydia trachomatis. The Journal of Clinical Investigation. 1997, vol. 99, No. 3, pp. 475-483.

Lampe, M., et al. Nucleotide sequence of the variable domains within the major outer membrane protein gene from serovariants of Chlamydia trachomatis. Infection and Immunity. 1993, vol. 61, No. 1, pp. 213-219.

Sayada, C., et al. Denaturing gradient gel electrophoresis analysis for the detection of point mutations in the Chlamydia trachomatis major outer-membrane protein gene. The Journal of Medical Microbiology. 1995, vol. 43, pp. 14-25.

* cited by examiner

*Primary Examiner* — Albert Navarro
(74) *Attorney, Agent, or Firm* — Paula A. Borden; Bozicevic, Field & Francis LLP.

(57) ABSTRACT

The present invention provides a method of classifying an epitope displayed by a polypeptide; a method of determining the presence of an epitope on a polypeptide encoded by a test nucleotide sequence; and a method of generating a nucleotide sequence encoding a polypeptide that exhibits a selected epitope. The present invention provides antigenic polypeptides that display selected epitope(s); chimeric macromolecules comprising such polypeptides; and compositions comprising the antigenic polypeptides or chimeric macromolecules. The present invention further provides methods of inducing an immune response to a *Chlamydia*. The present invention further provides arrays of nucleic acids, arrays of polypeptides, and arrays of antibodies, which arrays are useful in identification and/or classification of a *Chlamydia*.

6 Claims, 31 Drawing Sheets

Figure 3A:
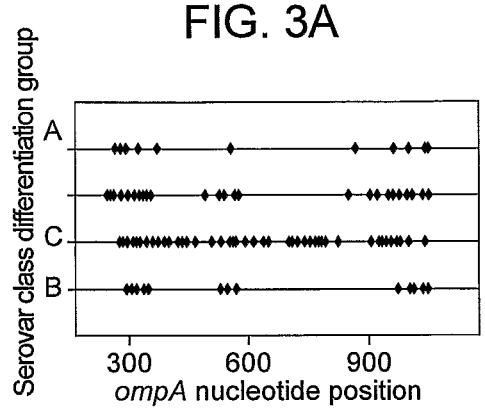

```
                                                                                              480
TGT ACA CTA GGA GCC TCT AGC GGA TAC CTT AAA GGA AAC TCT GCT TCT TTC AAT TTA GTG GGG
    .   T.  .   .   A.C T.  T.  .   .   .   .   .   .   .   .   .   .   .   .T  .A
    .   T.  .   A.C T.  T.  .   .   .   .   .   A.  .   .   .   .   .   .T  .A
    .   .   .   .   .   .   .   .   .   .   .   .   .   .   .   .   .   .   .   .
    .   T.  .   A.C T.  T.  .   .   .   .T  .   .A  .A  .   .   .   .   .T  .A
    .   T.  .   A.C T.  T.  .   .   .   .T  .   .A  .A  .   .   .   .   .T  .A
    .   T.  .   A.C T.  T.  T.  .   .   .T  .   .A  .A  .   .   .   .   .T  ..
    .   T.  .   A.C .   .   .   .   .   .T  .   .A  .A  .   .   .   .   .T  .C
    .   T.  .   A.C .   .   .   .   .   .T  .G  .A  .A  .   .   .   .   .T  .C
    .   T.G .   AA. .   .C  T.A .A  .   T.A .   .C  .   .C  .C  .C  .   .T  .A
    .   T.G .   AA. .   .C  T.A .A  .   T.A .   .C  .   .C  .C  .C  .   .T  .A
    .   T.G .   AA. .   .C  T.A .A  .   T.A .   .C  .   .C  .C  .C  .   .T  .A
    .   T.G .   AA. .   .C  T.A .A  .   T.A .G  .C  .   .C  .C  .C  .   .T  .A
    .   T.G .   AA. .   .C  T.A .A  .   T.A .   .C  .   .C  .C  .C  .   .T  .A
    .   T.G .   AA. .   .C  T.A .A  .   T.A .   .C  .   .C  .C  .C  .   .T  .A
    .   T.G .   AA. .   .C  T.A .A  .   T.A .   .C  .   .C  .C  .C  .   .T  .A
    .   T.G .   AA. .   .C  T.A .A  .   T.A .   .C  .   .C  .C  .C  .   .T  .A
```

FIG. 1I

|  | 481 |  |  |  |  |  |  |  |  |  |  | vs2 |  |  |  |  |
|---|---|---|---|---|---|---|---|---|---|---|---|---|---|---|---|---|
|  | TTA | TTC | GGA | AAT | AAT | GAG | AAC | CAG | ACT | AAA | --- | GTT | TCA | AAT | GGT | GCG | TTT | GTA |
| B | ... | ... | ... | ... | ... | ... | ... | ... | ... | ... | --- | ... | ... | ... | ... | A.. | ... | ... |
| Ba | ..G | ..T | ... | G.. | ... | ..A | ..T | ..A | .AA | .CG | --- | ... | GTC | ..A | .CG | .A.. | .C. | ... |
| D | ..G | ..T | ... | G.. | ... | ..A | ..T | ..A | .AA | .CG | --- | ... | GTC | ..A | .CG | .A.. | .C. | ... |
| Da | ..G | ..T | ... | G.. | ... | ..A | ..T | ..A | .GC | .CG | --- | ... | GTC | ..A | ACG | AAT | .C. | ... |
| E | ... | ... | ... | G.. | ... | ..A | ... | ..A | .GC | .CG | --- | ... | GTC | ..A | AAG | .AT | GC. | ... |
| L1 | ... | ... | ... | G.. | ... | ... | ... | ..T | G.. | ... | --- | ... | ... | G.. | A.. | AA. | C.. | ... |
| L2 | ... | ... | ... | G.. | ... | ..TA | ... | ..T | ... | ... | --- | ... | ... | G.. | A.. | AA. | C.. | ... |
| L2a | ... | ... | .G. | G.. | .GG. | ... | ... | .GCC | ..G | ... | --- | ... | C.T | GC. | .CA | .AT | AG. | A.T |
| F | ... | ... | .CG | G.. | .GG. | ..A | ... | .GCC | ..G | C.G | --- | ... | C.T | GC. | .CA | A.A | AG. | A.T |
| G | ... | ... | .C | G.. | ... | .A | ... | .GCC | ..G | C.G | --- | ... | C.T | GC. | .CA | A.A | AG. | A.T |
| C | ... | ... | ... | --- | --- | ACA | ..A | ACA | CAA | TCT | TCT | AGC | T.. | AAT | .CA | .CG | AA.. | C.. | A.T |
| A | ... | ... | ... | --- | --- | ACA | ..A | ACA | CAA | TCT | TCT | GGC | T.. | GAT | .CA | .CG | AAT | A.. | ..T |
| H | ... | ... | ... | --- | --- | ACA | ..A | ACA | .AA | TCT | TCT | GAT | T.. | AAT | .CA | .CG | AA.. | C.. | ... |
| I | ... | ... | ... | --- | --- | ACA | ..A | ACA | CAA | TCT | TCT | AAC | T.. | AAT | .CA | .CG | AA.. | C.. | ..T |
| Ia | ... | ... | ... | --- | --- | ACA | ..A | ACA | CAA | TCT | TCT | AAC | T.. | AAT | .CA | .CG | AA.. | C.. | A.T |
| J | ... | ... | ... | --- | --- | ACA | ..A | ACA | CAA | GCT | TCT | AGC | T.. | AAT | .CA | .CG | AA.. | C.. | A.T |
| Ja | ... | ... | ... | --- | --- | ACA | ..A | ACA | CAA | TCT | TCT | AGC | T.. | AAT | .CA | .CG | AA.. | C.. | T.T |
| K | ... | ... | ... | --- | --- | ACA | ..A | ACA | CAA | T.T | TCT | AAG | T.. | AAT | .CA | .CG | AAT | C.. | A.T |
| L3 | ... | ... | ... | --- | --- | ACA | ..A | ACA | CAA | TCT | ACT | AAC | T.. | AAT | .CA | .CG | AA.. | C.. | ..T |

B class: B, Ba, D, Da, E, L1, L2, L2a
I class: F, G
C class: C, A, H, I, Ia, J, Ja, K, L3

|  | 721 ACT | ATT | AAT | AAA | CCT | AAA | GGG | TAT | GTA | GGT | AAG | GAG | TTG | CCT | CTT | GAT | CTT | ACA | GCA | GGA |
|---|---|---|---|---|---|---|---|---|---|---|---|---|---|---|---|---|---|---|---|---|
| B | ... | ... | ... | ... | ... | ... | ... | ... | ... | ... | ... | ... | ... | ... | ... | ... | ... | ... | .T. | ... |
| Ba | ... | ... | ... | ... | ... | ... | ... | ... | ... | ... | ... | ... | ... | ... | ... | ... | ... | ... | ... | ... |
| D | ... | .C. | ... | ... | ... | ... | ... | ... | ... | ... | ... | ... | .T. | ... | ... | .CA | ..C | ..T | ... | ... |
| Da | ... | ... | ... | ... | ... | ... | ... | ... | ... | ... | ... | ... | .T. | ... | ... | ... | ... | ... | ... | ... |
| E | ... | ... | ... | .G. | ... | ... | .A. | ... | ... | .G. | C.A | ..A | ..C | ... | ... | ... | ... | .A. | ... | ... |
| L1 | ... | .C. | ... | .G. | .G. | ... | .A. | ... | ... | .G. | C.A | ..A | .T. | ... | ... | ... | ... | .A. | ... | ... |
| L2 | ... | ... | ... | .G. | ... | ... | .A. | ... | ... | .G. | C.A | ..A | ..C | ... | ... | ... | ... | ... | ... | ... |
| L2a | ... | .C. | ... | ... | ... | ... | ... | ... | ... | ... | ... | ... | .T. | ... | ... | ... | ... | ... | ... | ... |
| F | ... | ... | ... | .G. | ... | ... | .A. | ... | ... | .G. | C.A | ..A | ..C | ... | ..C | .CA | ..C | ... | ... | ... |
| G | ... | .C. | ... | .G. | .G. | ... | .A. | ... | .T. | .G. | GC. | ..A | .T. | .A. | .A. | A.. | .A. | ..C | ... | ... |
| C | ... | ... | ... | .G. | .G. | ... | .A. | ... | .T. | .G. | GC. | ..A | .T. | .A. | .A. | ... | .A. | ..C | ... | ... |
| A | ... | ... | ... | .G. | .G. | ... | .A. | ... | .T. | .G. | GC. | ..A | .T. | .A. | .A. | ... | .A. | ..C | ... | ... |
| H | ... | ... | ... | .G. | .G. | ... | .A. | ... | .T. | .G. | GC. | ..A | .T. | .A. | .A. | ... | .A. | .TC | ... | ... |
| I | ... | ... | ... | .G. | .G. | ... | .A. | ... | .T. | .G. | GC. | ..A | .T. | .A. | .A. | ... | .A. | ..C | ... | ... |
| Ia | ... | ... | ... | .G. | .G. | ... | .A. | ... | .T. | .G. | GC. | ..A | .T· | .A. | .A. | ... | .A. | ..C | ... | ... |
| J | ... | ... | ... | .G. | .G. | ... | .A. | ... | .T. | .G. | GC. | ..A | .T. | .A. | .A. | ... | .A. | ..C | ... | ... |
| Ja | ... | ... | ... | .G. | .G. | ... | .A. | ... | .T. | .G. | GC. | ..A | .T. | .A. | .A. | ... | .A. | ..C | ... | ... |
| K | ... | ... | ... | .G. | .G. | ... | .A. | ... | .T. | .G. | GT. | ..A | .T. | .A. | .A. | ... | .A. | ..C | ... | ... |
| L3 | ... | ... | ... | .G. | .G. | ... | .A. | ... | .T. | .G. | GC. | ..A | ... | .A. | .A. | ... | .A. | ..C | ... | ... |

B class: B, Ba, D, Da, E, L1, L2, L2a
I class: F, G
C class: C, A, H, I, Ia, J, Ja, K, L3 vs3

```
     1081
     AGA AAA TCT TGC GGT ATT GCA GTA GGA ACA ACT ATT GTG GAT GCA GAC AAA TAC GCA GTT
B    ... ... ... ... ... ... ... ... ... ... ... ... ... ... ... ... ... ... ... ...
Ba   ... ... ... ... ... ... ... ... ... ... ... ... ... ... ... ... ... ... ... ...
D    ... ... ... ... ... ... ... ... ... ... ... ... ... ... ... ... ... ... ... ...
Da   ... ... ... ... ... ... ... ... ... ... ... ... ... ... ... ... ... ... ... ...
E    ... ... ... ... ... ... ... ... ... ..G ... ... .A. ... ... ... ... ... ... ...
L1   ... ... ... ... ... ... ... ... ... ... ... ... ... ... ... ... ... ... ... ...
L2   ... ... ... ... ... ... ... ... ... ... ... ... ... ... ... ... ... ... ... ...
L2a  ... ... ... ... ... ... ... ... ... ... ... ... ... ... ... ... ... ... ... ...
F    ... ... ... ... ... ... ... ... ... ..G ... ... .A. ... ... ... ... ... ... ...
G    ... ... ... ... ... ... ... ... ... ... ... ... ... ... ... ... ... ... ... ...
C    ... ... ... ... ... ... ... ... ... ..G ... ... .A. ... ... ..T ... ... ... ...
A    ... ... ... ... ... ... ... ... ... ..G ... ... .A. ... ... ... ... ... ... ...
H    ... ... ... ... ... ... ... ... ... ..G ... ... .A. ... ... ... ... ... ... ...
I    ... ... ... ... ... ... ... ... ... ..G ... ... .A. ... ... ..T ... ... ... ...
Ia   ... ... ... ... ... ... ... ... ... ... ..G ... .A. ... ... ... ... ... ... ...
J    ... ... ... ... ... ... ... ... ... ..G ... ... .A. ... ... ... ... ... ... ...
Ja   ... ... ... ... ... ... ... ... ... ..G ... ... .A. ... ... ... ... ... ... ...
K    ... ... ... ... ... ... ... ... ... ..G ... ... .A. ... ... ..T ... ... ... ...
L3   ... ... ... ... ... ... ... ... ... ..G ... ... .A. ... ... ... ... ... ... ...
```

B class: B, Ba, D, Da, E, L1, L2, L2a
I class: F, G
C class: C, A, H, I, Ia, J, Ja, K, L3

FIG. 1T

| ACA | GTT | GAG | ACT | CGC | TTG | ATC | GAT | GAG | AGA | GCT | GCT | CAC | GTA | AAT | GCA | CAA | TTC | CGC | TTC | |
|---|---|---|---|---|---|---|---|---|---|---|---|---|---|---|---|---|---|---|---|---|
| | | | | | | | | | | | | | | | | | | | | (SEQ ID NO:134) |
| . | . | . | . | . | . | . | . | . | . | . | . | . | . | . | . | . | . | . | . | (SEQ ID NO:135) |
| . | . | . | . | . | . | . | . | . | . | . | .A | . | . | . | . | . | . | . | . | (SEQ ID NO:136) |
| . | . | . | . | . | . | . | . | . | . | . | .A | . | . | . | . | . | . | . | . | (SEQ ID NO:137) |
| . | . | . | . | . | . | . | . | . | . | . | . | . | . | . | . | . | . | . | . | (SEQ ID NO:138) |
| . | . | . | . | . | . | . | . | . | . | . | . | . | . | . | . | . | . | . | . | (SEQ ID NO:139) |
| . | . | . | . | . | . | . | . | . | . | . | . | . | . | . | . | . | . | . | . | (SEQ ID NO:140) |
| . | . | . | . | . | . | . | . | . | . | . | . | . | . | . | . | . | . | . | . | (SEQ ID NO:141) |
| . | . | . | .G | . | . | . | . | . | . | . | . | . | . | . | . | . | . | . | . | (SEQ ID NO:142) |
| . | . | . | . | . | . | . | . | . | . | . | . | . | . | . | . | . | . | . | . | (SEQ ID NO:143) |
| . | . | . | . | . | . | . | . | . | . | . | .A | . | . | . | . | . | . | .G | . | (SEQ ID NO:144) |
| . | . | . | . | . | .T | . | . | . | . | . | .A | . | . | . | . | . | . | . | . | (SEQ ID NO:145) |
| . | . | . | . | . | . | . | . | . | . | . | .A | . | . | . | . | . | . | . | . | (SEQ ID NO:146) |
| . | . | . | . | . | . | . | . | . | . | . | .A | . | . | . | . | . | . | .G | . | (SEQ ID NO:147) |
| . | . | . | . | . | . | . | . | . | . | . | .A | . | . | . | . | . | . | .G | . | (SEQ ID NO:148) |
| . | . | . | . | . | . | . | . | . | . | . | .A | . | . | . | . | . | . | .G | . | (SEQ ID NO:149) |
| . | . | . | . | . | . | . | . | . | . | . | .A | . | . | . | . | . | . | . | . | (SEQ ID NO:150) |
| . | . | . | . | . | . | . | . | . | . | . | .A | . | . | . | . | . | . | .G | . | (SEQ ID NO:151) |
| . | . | . | . | . | . | . | . | . | . | . | .A | . | . | . | . | . | . | . | . | (SEQ ID NO:152) |

->|       |<------VS4-->|
              1 1 1
 7 9 9 9 9 0 0 0
 8 2 4 5 5 1 1 3
 9 2 7 3 6 3 4 6
 A G G T C C T A   (SEQ ID NO:153)
 T A A C A T C T   (SEQ ID NO:154)
 3 1 2 2 2 2 3 1
 S N N N N N N N
```

FIG. 5

```
           |<-----VS1----->|      |<-----VS2----->|
           2 2 2 2 2 2 2 2 3 4 4 4 5 5 5 5 5 5 5 5 5 5 5 5 5 5
           4 5 6 7 7 8 9 9 0 7 8 8 0 1 1 2 3 3 3 3 7 7 7 8 9 9
           9 7 8 5 8 9 0 3 4 7 0 9 9 0 3 9 3 6 7 8 6 7 9 2 4 7
line 1)    A   G       A           G C             A C T C C C
line 2)                                 T   A   G
line 3)              T
line 4)                        G
line 5) CG       A A G
line 6)                          C             G
line 7)                    G                      C
line 8)      G
line 9)                                                       T
           3 2 1 2 2 1 2 2 1 3 3 3 2 3 3 1 2 2 3 1 3 1 3 3 3 3
           B N N N N N N N N S S S N N B N N N N N S S S S B S
                                       |<-----VS3--------->|
           5 6 6 6 6 6 6 6 6 6 6 6 7 7 7 7 7 7 7 7 7 7 8 8 8 8
           9 0 0 1 1 3 3 4 5 6 7 8 6 7 7 7 7 8 8 9 9 9 0 0 1 3
           8 8 9 2 8 3 6 2 4 0 8 1 5 3 4 7 9 1 9 4 5 7 1 4 0 4
line 1)  T   G     A G C           C A C T   T   A     G C A G
line 10)              A
line 11)                                                 T
line 6)      C   A        C C   C G                G   T
line 7)                       G
line 9)                 G
           1 2 3 3 3 3 3 3 3 3 3 2 3 3 2 1 3 2 3 2 3 3 3 3
           N N B S S S B S S S S N N N S N N S N B N S S S S
           |<------VS4-------->|
                               1 1 1 1
           8 9 9 9 9 9 9 9 0 0 0 0
           8 2 5 5 5 5 5 6 0 3 3 3
           2 1 0 4 5 6 7 1 8 3 4 6
  2)       G T             G   A
  10)                            A
  5)                        G
  6)                    G
  7)  T        C G A G
           3 3 2 3 1 2 3 1 3 1 2 1
           S S N S N N N N N N N N
``` line 1) Nt differentiates E from B,Ba,D,Da,L1,L2, and L2a.
line 2) Nt differentiates L1 from B,Ba,D,Da,E,L2, and L2a.
line 3) Nt differentiates B from Ba,D,Da,E,L1,L2, and L2a.
line 11) Nt differentiates Ba from B,D,Da,E,L1,L2, and L2a.
line 4) Nt differentiates L2a from B,Ba,D,Da,E,L1 and L2.
line 10) Nt differentiates Da from B,Ba,E,L1,L2 and L2a.
line 5) Nt differentiates D and Da from B,Ba,E,L1,L2, and L2a.
line 6) Nt differentiates L2 and L2a from B,Ba,D,Da,E, and L1.
line 7) Nt differentiates B and Ba from D,Da,E,L1,L2 and L2a.
line 8) Nt differentiates Ba and L1 from B,D,Da,E,L2 and L2a.
line 9) Nt differentiates E and L1 from B,Ba,D,Da,L2, and L2a
Nucleotide ambiguity code: C/T =Y;A/G=R;A/T=W;
G/C=S;T/G=K;C/A=M;NOT C=D;NOT T=V;NOT G=H; NOT A=B.

FIG. 6A

```
          |<-----------------------VS1----------------------->|       |<-
          2 2 2 2 2 2 2 2 2 2 2 2 2 2 3 3 3 3 3 3 3 4 4 4 5
          4 4 5 5 6 6 6 7 7 8 8 8 8 9 9 0 0 0 0 1 1 2 1 4 5 0
          6 9 5 8 0 8 9 7 8 1 2 4 9 0 4 4 5 7 8 2 3 1 7 9 9 8
line 12)                          G G T G           C
line 13)C A T C A         G   T C
line 14)                                        T C
line 15)          A                                         G
line 16)            A           A
line 17)                                                      C
line 18)    G T                                 A
line 19)                                              A   T
 line 2)        A
 line 3)          C
          3 3 3 3 2 1 2 1 2 2 3 2 1 2 3 1 2 1 2 3 1 3 3 2 3 1
          S S S S N N N N N B N N N N N N N N S N S S N S N ----------VS2---------->|              |-3-|
          5 5 5 5 5 5 5 5 5 5 5 5 5 5 5 6 6 6 7 7 7 8 8 8
          0 1 1 1 1 2 3 3 5 5 5 6 6 7 8 8 9 2 2 9 1 5 7 0 2 5
          9 0 1 2 3 6 7 8 0 1 9 2 3 0 4 6 1 5 7 6 2 8 2 4 8 2
line 12)          G A                                     A
line 13)                                            G
line 14)                    G       T                 A
line 15)      G           G         C           T
line 16)    G           T
line 17)A A   C
line 18)      G                             A       T
line 19)                              A                   T
line 20)                                        T G
line 22)          G
 line 4)              G
 line 5)    T
 line 6)                        A
          2 3 1 2 3 1 3 1 1 2 1 1 2 3 2 1 3 1 3 3 1 2 1 3 3 3
          N N N B N N N N N N N N N S N N S S S S N G N S S S
```

FIG. 6B

```
        |<----------------VS4---------------->|
                        1 1 1 1 1 1 1 1 1 1
        8 8 9 9 9 9 9 9 9 9 9 9 0 0 0 0 0 0 0 0 0 0
        5 6 5 5 6 7 7 8 8 9 9 9 0 0 3 3 3 3 3 3 3 3
        5 5 5 8 1 0 1 6 7 0 2 3 6 7 0 2 3 4 6 7 8 9
line 12)    A C     A C
line 14)            G A T C T       G
line 15)                        G
line 16)  C
line 19)C
line 21)                                T T       G   A
line 22)G
 line 7)    G
 line 8)                    G
 line 9)                                    C
line 10)                                    C
line 11)                                        C
        3 1 1 1 1 2 2 3 3 2 3 1 2 1 3 1 2 3 1 2 3
        S S N N N N N N S N N N N N B N N N N N
```

Line 12: Nt differentiates A from C,H,I,Ia,J,Ja,K and L3.
Line 13: Nt differentiates L3 from A,C,H,I,Ia,J,Ja and K.
Line 14: Nt differentiates C from A,H,I,Ia,J,Ja,K and L3.
Line 15: Nt differentiates K from A,C,H,I,Ia,J,Ja and L3.
Line 16: Nt differentiates H from A,C,I,Ia,J,Ja,K and L3.
Line 17: Nt differentiates A, C and L3 from I,Ia,J,Ja and K.
Line 18: Nt differentiates Ja from A,C,H,Ia,K and L3.
Line 19: Nt differentiates C from A,H,Ia,J,Ja,K and L3.
Line 20: Nt differentiates K from A,C,H,Ia,Ja and L3.
Line 21: Nt differentiates A from C,H,Ia,J,Ja,K and L3.
Line 22: Nt differentiates Ia from A,C,H,J,Ja,K and L3.
Line 2: Nt differentiates Ia and L3 from A,C,H,I,J,Ja,and K.
Line 3: Nt differentiates H and L3 from A,C,I,Ia,J,Ja, and K.
Line 4: Nt differentiates H and K from A,C,I,Ia,J,Ja and L3.
Line 5: Nt differentiates A and K from C,H,I,Ia,Ja and L3.
Line 6: Nt differentiates Ja and L3 from A,C,H,I,Ia,J and K.
Line 7: Nt differentiates A and L3 from C,H,I,Ia,J,Ja and K.
Line 8: Nt differentiates C and L3 from A,H,I,Ia,J,Ja,and K.
Line 9: Nt differentiates A from C,Ia,J,Ja,K and L3.
Line 10: Nt differentiates A and L3 from C,H,Ia,J,Ja, and K.
Line 11: Nt differentiates A and C from H,Ia,J,Ja,K and L3.

N Differentiating nt. encodes for nonsynonymous changes only
S Differentiating nt. encodes for synonymous changes only
B Differentiating nt. encodes for both nonsynonymous and synonymous changes
G Unable to evaluate changes due to presence of gap within codon.
Nucleotide ambiguity code: C/T =Y;A/G=R;A/T=W;
G/C=S;T/G=K;C/A=M;NOT C=D;NOT T=V;NOT G=H; NOT A=B

FIG. 8

C CLASS
$^{267}T^{270}C^{279}A^{280}G^{286}T^{287}T^{288}A^{291}A^{293}A^{296}A$
$^{310}A^{311}A^{315}T^{318}T^{321}Y^{322}C^{324}A^{330}C^{345}C$
$^{360}A^{369}G^{372}C^{390}A^{396}C^{426}G^{432}A^{437}C^{441}T^{445}T^{44}$
$^{7}A^{465}C^{508}Y^{527}A^{552}T^{553}G^{554}C^{555}T^{558}G$
$^{565}G^{588}C^{609}A^{612}T^{639}G^{648}G^{702}T^{708}T^{718}T^{720}C^{72}$
$^{3}A^{741}G^{753}T^{757}G^{758}Y^{768}A^{775}A^{780}C^{792}A$
$^{825}C^{867}A^{904}A^{908}T^{930}C^{936}G^{945}T^{960}A^{966}G^{972}C^{98}$
$^{1}A^{999}T^{1001}A^{1002}A^{1005}A^{1042}A^{1044}C^{1045}G$
$^{1047}M^{1050}G$

NOT C CLASS
$^{267}M^{270}W^{279}T^{280}W^{286}A^{287}A^{288}T^{291}K^{293}Y^{296}C$
$^{310}Y^{311}K^{315}A^{318}A^{321}A^{322}R^{324}G^{330}T^{345}T^{360}G$
$^{369}M^{372}T^{390}G^{396}T^{426}A^{432}C^{437}G^{441}A^{445}C^{447}T$
$^{465}T^{508}R^{527}Y^{552}G^{553}M^{554}R^{555}S^{558}W^{565}T^{588}T$
$^{609}B^{612}M^{639}A^{648}T^{702}C^{708}C^{718}G^{720}W^{723}G^{741}T$
$^{753}A^{757}M^{758}A^{768}T^{775}C^{780}A^{792}T^{825}T^{867}S^{904}C$
$^{908}C^{930}T^{936}W^{945}R^{960}T^{966}W^{972}T^{981}K^{999}A^{1001}S$
$^{1002}Y^{1005}C^{1042}G^{1044}W^{1045}C^{1047}G^{1050}M$

I CLASS
$^{247}G^{255}C^{261}T^{262}T^{263}T^{264}A^{265}G^{267}C^{270}A^{280}T^{282}T$
$^{285}G^{291}G^{295}T^{298}A^{300}T^{308}A^{312}G^{317}A^{322}A^{327}C^{333}A$
$^{342}G^{354}C^{357}A^{369}C^{489}C^{526}C^{534}A^{539}G^{553}C^{554}A^{555}G$
$^{564}G^{573}G^{850}T^{867}C^{906}T^{919}T^{921}T^{954}A^{964}G^{966}A^{978}C$
$^{996}A^{1000}T^{1002}C^{1011}A^{1038}G^{1044}A^{1048}A^{1050}A^{1051}T$

B CLASS
$^{247}C^{255}T^{261}G^{262}C^{263}C^{264}T^{265}A^{267}A^{270}T$
$^{280}A^{282}A^{285}C^{291}T^{295}G^{298}C^{300}A^{308}C^{312}T^{31}$
$^{7}C^{322}G^{327}T^{333}T^{342}A^{354}T^{357}T^{369}A^{489}R$
$^{526}G^{534}K^{539}Y^{553}A^{554}G^{555}C^{564}A^{573}T$
$^{850}G^{867}G^{906}A^{919}G^{921}V^{954}Y^{964}T^{966}T^{978}K^{99}$
$^{6}T^{1000}R^{1002}T^{1011}G^{1038}A^{1044}T^{1048}C$
$^{1050}C^{1051}G$

| Y = C/T | W = A/T | K = T/G |
|---------|---------|---------|
| R = A/G | S = G/C | M = C/A |

D = NOT C
V = NOT T
H = NOT G
B = NOT A

FIG. 9

```
                    ┌──────────────────────────────────────┐
                    E                                      B, Ba, D, Da, L1, L2, L2a
        257A 269G 304A 509G                      257C 269C 304T 509M 510D 576G
        510C 576A 577C 579T                      577T 579G 582T 594T 597T 598G 609Y
        582C 594C 597C 598T                      618Y 633A 636T 773A 774T 777T 779M
        609G 618A 633G 636C                      789A 795T 801A 804A 810G 834A
        773C 774A 777C 779T
        789T 795A 801G 804C
        810A 834G

┌──────────────────────────────────────┐
                    L1                                     B, Ba, D, Da, L2, L2a
        513T 533A 538G 921G 950T                 513V 533S 538Y 921M
        1008G 1034A                              950C 1008T 1034G

┌──────────────────────────────────────┐
                    L2, L2a                                B, Ba, D, Da
        480C 529G 608C 612A                      480R 529A 608T 612C
        642C 654C 678C 681G                      642T 654R 678T 681A
        794G 797T 961G                           794C 797C 961A

┌──────────────────────────────────────┐
                    B, Ba                                  D, Da
        477G 536C 765G                           477T 536A 765Y 882

FIG. 10
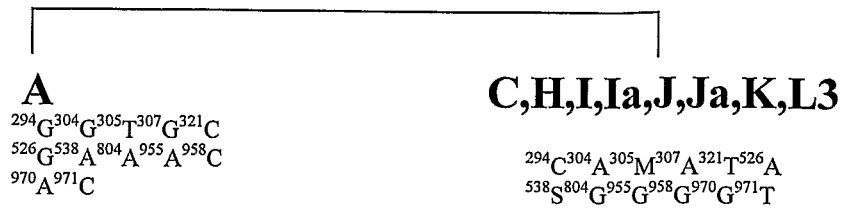
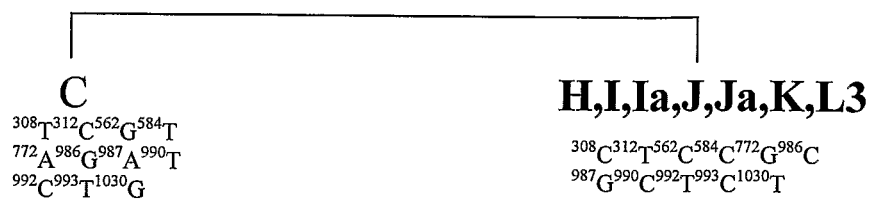
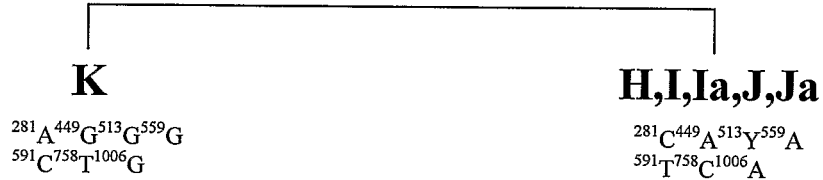
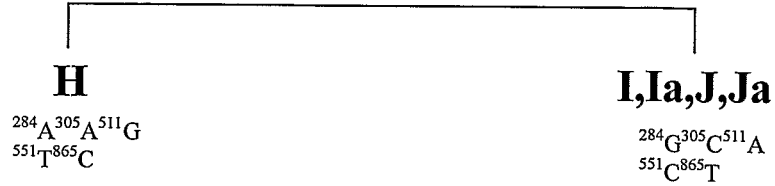

SEQUENCE LISTING

<160> NUMBER OF SEQ ID NOS: 154

<210> SEQ ID NO 1
<211> LENGTH: 27
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(1)
<223> OTHER INFORMATION: Xaa = A, V, or absent
<220> FEATURE:
<221> NAME/KEY: VARIANT
<222> LOCATION: (2)...(2)
<223> OTHER INFORMATION: Xaa = E, T, K, or absent
<220> FEATURE:
<221> NAME/KEY: VARIANT
<222> LOCATION: (3)...(3)
<223> OTHER INFORMATION: Xaa = A, T, P, or absent
<220> FEATURE:
<221> NAME/KEY: VARIANT
<222> LOCATION: (4)...(4)
<223> OTHER INFORMATION: Xaa = I, V, or absent
<220> FEATURE:
<221> NAME/KEY: VARIANT
<222> LOCATION: (5)...(5)
<223> OTHER INFORMATION: Xaa = F, L, V, or absent
<220> FEATURE:
<221> NAME/KEY: VARIANT
<222> LOCATION: (6)...(6)
<223> OTHER INFORMATION: Xaa = D or absent
<220> FEATURE:
<221> NAME/KEY: VARIANT
<222> LOCATION: (7)...(7)
<223> OTHER INFORMATION: Xaa = V, T, I, or absent
<220> FEATURE:
<221> NAME/KEY: VARIANT
<222> LOCATION: (8)...(8)
<223> OTHER INFORMATION: Xaa = T
<220> FEATURE:
<221> NAME/KEY: VARIANT
<222> LOCATION: (9)...(9)
<223> OTHER INFORMATION: Xaa = T
<220> FEATURE:
<221> NAME/KEY: VARIANT
<222> LOCATION: (10)...(10)
<223> OTHER INFORMATION: Xaa = L
<220> FEATURE:
<221> NAME/KEY: VARIANT
<222> LOCATION: (11)...(11)
<223> OTHER INFORMATION: Xaa = N
<220> FEATURE:
<221> NAME/KEY: VARIANT
<222> LOCATION: (11)...(11)
<223> OTHER INFORMATION: Xaa = N
<220> FEATURE:
<221> NAME/KEY: VARIANT
<222> LOCATION: (12)...(12)
<223> OTHER INFORMATION: Xaa = P or R
<220> FEATURE:
<221> NAME/KEY: VARIANT
<222> LOCATION: (13)...(13)
<223> OTHER INFORMATION: Xaa = T
<220> FEATURE:
<221> NAME/KEY: VARIANT
<222> LOCATION: (14)...(14)
<223> OTHER INFORMATION: Xaa = T or I
<220> FEATURE:
<221> NAME/KEY: VARIANT
<222> LOCATION: (15)...(15)
<223> OTHER INFORMATION: Xaa = A or T
<220> FEATURE:
<221> NAME/KEY: VARIANT
<222> LOCATION: (16)...(16)
<223> OTHER INFORMATION: Xaa = G

```
<220> FEATURE:
<221> NAME/KEY: VARIANT
<222> LOCATION: (17)...(17)
<223> OTHER INFORMATION: Xaa = A, C, K or absent
<220> FEATURE:
<221> NAME/KEY: VARIANT
<222> LOCATION: (18)...(18)
<223> OTHER INFORMATION: Xaa = G or absent
<220> FEATURE:
<221> NAME/KEY: VARIANT
<222> LOCATION: (19)...(19)
<223> OTHER INFORMATION: Xaa = S, G, T, A, E, D or absent
<220> FEATURE:
<221> NAME/KEY: VARIANT
<222> LOCATION: (20)...(20)
<223> OTHER INFORMATION: Xaa = V or absent
<220> FEATURE:
<221> NAME/KEY: VARIANT
<222> LOCATION: (21)...(21)
<223> OTHER INFORMATION: Xaa = A, V, I, K or absent
<220> FEATURE:
<221> NAME/KEY: VARIANT
<222> LOCATION: (22)...(22)
<223> OTHER INFORMATION: Xaa = A, G, S, T or absent
<220> FEATURE:
<221> NAME/KEY: VARIANT
<222> LOCATION: (23)...(23)
<223> OTHER INFORMATION: Xaa = A, G, N, S or absent
<220> FEATURE:
<221> NAME/KEY: VARIANT
<222> LOCATION: (24)...(24)
<223> OTHER INFORMATION: Xaa = G, N or absent
<220> FEATURE:
<221> NAME/KEY: VARIANT
<222> LOCATION: (25)...(25)
<223> OTHER INFORMATION: Xaa = A, S, T or absent
<220> FEATURE:
<221> NAME/KEY: VARIANT
<222> LOCATION: (26)...(26)
<223> OTHER INFORMATION: Xaa = D, E or absent
<220> FEATURE:
<221> NAME/KEY: VARIANT
<222> LOCATION: (27)...(27)
<223> OTHER INFORMATION: Xaa = G, N or absent

<400> SEQUENCE: 1

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa
            20                  25

<210> SEQ ID NO 2
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)...(2)
<223> OTHER INFORMATION: Xaa = A or T
<220> FEATURE:
<221> NAME/KEY: VARIANT
<222> LOCATION: (5)...(5)
<223> OTHER INFORMATION: Xaa = D or E
<220> FEATURE:
<221> NAME/KEY: VARIANT
<222> LOCATION: 1, 7
<223> OTHER INFORMATION: Xaa = Any Amino Acid

<400> SEQUENCE: 2

Xaa Xaa Gly Thr Xaa Ala Xaa
 1               5

<210> SEQ ID NO 3
```

```
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Ala Gly Thr Glu Ala
 1               5

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Ala Gly Thr Asp Ala
 1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Leu Asp Leu Thr Ala Gly Thr Asp Ala
 1               5

<210> SEQ ID NO 6
<211> LENGTH: 10
<212> TYPE: PRT
<213> ORGANISM: Artificial Sequence
<220> FEATURE:
<223> OTHER INFORMATION: synthetic peptide

<400> SEQUENCE: 6

Leu Asp Leu Thr Ala Gly Thr Asp Ala Thr
 1               5                  10

<210> SEQ ID NO 7
<211> LENGTH: 8
<212> TYPE: PRT
<213> ORGANISM: Artificial Sequence
<220> FEATURE:
<223> OTHER INFORMATION: synthetic peptide

<400> SEQUENCE: 7

Asp Leu Thr Ala Gly Thr Asp Ala
 1               5

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Leu Asp Ile Thr Ala Gly Thr Glu Ala
 1               5

<210> SEQ ID NO 9
<211> LENGTH: 10
<212> TYPE: PRT
```

<213> ORGANISM: Artificial Sequence
<220> FEATURE:
<223> OTHER INFORMATION: synthetic peptide

<400> SEQUENCE: 9

Leu Asp Ile Thr Ala Gly Thr Glu Ala Thr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: synthetic peptide

<400> SEQUENCE: 10

Asp Ile Thr Ala Gly Thr Glu Ala
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)...(4)
<223> OTHER INFORMATION: Xaa = D or E

<400> SEQUENCE: 11

Thr Gly Thr Xaa Ala
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 6
<223> OTHER INFORMATION: Xaa = Any Amino Acid

<400> SEQUENCE: 12

Xaa Thr Ile Ala Gly Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 2, 7
<223> OTHER INFORMATION: Xaa = Any Amino Acid

<400> SEQUENCE: 13

Cys Xaa Thr Ile Ala Gly Xaa Cys
1               5

<210> SEQ ID NO 14
<211> LENGTH: 11
<212> TYPE: PRT
<213> ORGANISM: Artificial Sequence
<220> FEATURE:
<223> OTHER INFORMATION: synthetic peptide

```
-continued

<220> FEATURE:
<221> NAME/KEY: VARIANT
<222> LOCATION: 1, 11
<223> OTHER INFORMATION: Xaa = Any Amino Acid

<400> SEQUENCE: 14

Xaa Thr Thr Leu Asn Pro Thr Ile Ala Gly Xaa
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 2, 12
<223> OTHER INFORMATION: Xaa = Any Amino Acid

<400> SEQUENCE: 15

Cys Xaa Thr Thr Leu Asn Pro Thr Ile Ala Gly Xaa Cys
 1               5                  10

<210> SEQ ID NO 16
<211> LENGTH: 7
<212> TYPE: PRT
<213> ORGANISM: Artificial Sequence
<220> FEATURE:
<223> OTHER INFORMATION: synthetic peptide

<400> SEQUENCE: 16

Ala Glu Thr Ile Phe Asp Val
 1               5

<210> SEQ ID NO 17
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(1)
<223> OTHER INFORMATION: Xaa = A or K
<220> FEATURE:
<221> NAME/KEY: VARIANT
<222> LOCATION: (3)...(3)
<223> OTHER INFORMATION: Xaa = D or T
<220> FEATURE:
<221> NAME/KEY: VARIANT
<222> LOCATION: (5)...(5)
<223> OTHER INFORMATION: Xaa = K or V
<220> FEATURE:
<221> NAME/KEY: VARIANT
<222> LOCATION: (6)...(6)
<223> OTHER INFORMATION: Xaa = T or S
<220> FEATURE:
<221> NAME/KEY: VARIANT
<222> LOCATION: (7)...(7)
<223> OTHER INFORMATION: Xaa = S or G
<220> FEATURE:
<221> NAME/KEY: VARIANT
<222> LOCATION: (8)...(8)
<223> OTHER INFORMATION: Xaa = A or S
<220> FEATURE:
<221> NAME/KEY: VARIANT
<222> LOCATION: (9)...(9)
<223> OTHER INFORMATION: Xaa = E or D
<220> FEATURE:
<221> NAME/KEY: VARIANT
<222> LOCATION: (10)...(10)
<223> OTHER INFORMATION: Xaa = G or N
```

-continued

```
<400> SEQUENCE: 17

Xaa Gly Xaa Val Xaa Xaa Xaa Xaa Xaa
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic peptide

<400> SEQUENCE: 18

Ala Gly Asp Val Lys Thr Ser Ala Glu Gly
1               5                   10

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

Ala Gly Asp Val Lys Thr Ser Ala Glu
1               5

<210> SEQ ID NO 20
<211> LENGTH: 9
<212> TYPE: PRT
<213> ORGANISM: Artificial Sequence
<220> FEATURE:
<223> OTHER INFORMATION: synthetic peptide

<400> SEQUENCE: 20

Lys Gly Thr Val Val Thr Ser Ala Glu
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic peptide

<400> SEQUENCE: 21

Lys Gly Thr Val Val Ser Ser Ala Glu
1               5

<210> SEQ ID NO 22
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (6)...(6)
<223> OTHER INFORMATION: Xaa = A or S

<400> SEQUENCE: 22

Lys Gly Thr Val Val Xaa Ser Ser Ala Glu
1               5                   10

<210> SEQ ID NO 23
<211> LENGTH: 11
<212> TYPE: PRT
<213> ORGANISM: Artificial Sequence
<220> FEATURE:
```

```
<223> OTHER INFORMATION: synthetic peptide

<400> SEQUENCE: 23

Cys Thr Thr Leu Asn Pro Thr Ile Ala Gly Cys
1               5                  10

<210> SEQ ID NO 24
<211> LENGTH: 16
<212> TYPE: PRT
<213> ORGANISM: Artificial Sequence
<220> FEATURE:
<223> OTHER INFORMATION: synthetic peptide

<400> SEQUENCE: 24

Ala Glu Thr Ile Phe Asp Val Thr Thr Leu Asn Pro Thr Ile Ala Gly
1               5                   10                  15

<210> SEQ ID NO 25
<211> LENGTH: 18
<212> TYPE: PRT
<213> ORGANISM: Artificial Sequence
<220> FEATURE:
<223> OTHER INFORMATION: synthetic peptide

<400> SEQUENCE: 25

Cys Ala Glu Thr Ile Phe Asp Val Thr Thr Leu Asn Pro Thr Ile Ala
1               5                   10                  15

Gly Cys

<210> SEQ ID NO 26
<211> LENGTH: 26
<212> TYPE: PRT
<213> ORGANISM: Artificial Sequence
<220> FEATURE:
<223> OTHER INFORMATION: synthetic peptide

<400> SEQUENCE: 26

Ala Glu Thr Ile Phe Asp Val Thr Thr Leu Asn Pro Thr Ile Ala Gly
1               5                   10                  15

Ala Gly Cys Val Lys Thr Ser Ala Glu Gly
            20                  25

<210> SEQ ID NO 27
<211> LENGTH: 28
<212> TYPE: PRT
<213> ORGANISM: Artificial Sequence
<220> FEATURE:
<223> OTHER INFORMATION: synthetic peptide

<400> SEQUENCE: 27

Cys Ala Glu Thr Ile Phe Asp Val Thr Thr Leu Asn Pro Thr Ile Ala
1               5                   10                  15

Gly Ala Gly Cys Val Lys Thr Ser Ala Glu Gly Cys
            20                  25

<210> SEQ ID NO 28
<211> LENGTH: 16
<212> TYPE: PRT
<213> ORGANISM: Artificial Sequence
<220> FEATURE:
<223> OTHER INFORMATION: synthetic peptide

<400> SEQUENCE: 28

Ala Glu Thr Ile Leu Asp Val Thr Thr Leu Asn Pro Thr Ile Ala Gly
1               5                   10                  15
```

-continued

<210> SEQ ID NO 29
<211> LENGTH: 18
<212> TYPE: PRT
<213> ORGANISM: Artificial Sequence
<220> FEATURE:
<223> OTHER INFORMATION: synthetic peptide

<400> SEQUENCE: 29

Cys Ala Glu Thr Ile Leu Asp Val Thr Thr Leu Asn Pro Thr Ile Ala
1               5                   10                  15

Gly Cys

<210> SEQ ID NO 30
<211> LENGTH: 19
<212> TYPE: PRT
<213> ORGANISM: Artificial Sequence
<220> FEATURE:
<223> OTHER INFORMATION: synthetic peptide

<400> SEQUENCE: 30

Thr Thr Leu Asn Pro Thr Ile Ala Gly Ala Gly Cys Val Lys Thr Ser
1               5                   10                  15

Ala Glu Gly

<210> SEQ ID NO 31
<211> LENGTH: 21
<212> TYPE: PRT
<213> ORGANISM: Artificial Sequence
<220> FEATURE:
<223> OTHER INFORMATION: synthetic peptide

<400> SEQUENCE: 31

Cys Thr Thr Leu Asn Pro Thr Ile Ala Gly Ala Gly Cys Val Lys Thr
1               5                   10                  15

Ser Ala Glu Gly Cys
            20

<210> SEQ ID NO 32
<211> LENGTH: 18
<212> TYPE: PRT
<213> ORGANISM: Artificial Sequence
<220> FEATURE:
<223> OTHER INFORMATION: synthetic peptide

<400> SEQUENCE: 32

Thr Thr Leu Asn Pro Thr Ile Ala Gly Ala Gly Asp Val Lys Thr Ser
1               5                   10                  15

Ala Glu

<210> SEQ ID NO 33
<211> LENGTH: 20
<212> TYPE: PRT
<213> ORGANISM: Artificial Sequence
<220> FEATURE:
<223> OTHER INFORMATION: synthetic peptide

<400> SEQUENCE: 33

Cys Thr Thr Leu Asn Pro Thr Ile Ala Gly Ala Gly Asp Val Lys Thr
1               5                   10                  15

Ser Ala Glu Cys
            20

<210> SEQ ID NO 34
<211> LENGTH: 18

```
<212> TYPE: PRT
<213> ORGANISM: Artificial Sequence
<220> FEATURE:
<223> OTHER INFORMATION: synthetic peptide

<400> SEQUENCE: 34

Thr Thr Leu Asn Pro Thr Ile Ala Gly Lys Gly Thr Val Val Thr Ser
1               5                   10                  15

Ala Glu

<210> SEQ ID NO 35
<211> LENGTH: 20
<212> TYPE: PRT
<213> ORGANISM: Artificial Sequence
<220> FEATURE:
<223> OTHER INFORMATION: synthetic peptide

<400> SEQUENCE: 35

Cys Thr Thr Leu Asn Pro Thr Ile Ala Gly Lys Gly Thr Val Val Thr
1               5                   10                  15

Ser Ala Glu Cys
            20

<210> SEQ ID NO 36
<211> LENGTH: 18
<212> TYPE: PRT
<213> ORGANISM: Artificial Sequence
<220> FEATURE:
<223> OTHER INFORMATION: synthetic peptide

<400> SEQUENCE: 36

Thr Thr Leu Asn Pro Thr Ile Ala Gly Lys Gly Thr Val Val Ser Ser
1               5                   10                  15

Ala Glu

<210> SEQ ID NO 37
<211> LENGTH: 20
<212> TYPE: PRT
<213> ORGANISM: Artificial Sequence
<220> FEATURE:
<223> OTHER INFORMATION: synthetic peptide

<400> SEQUENCE: 37

Cys Thr Thr Leu Asn Pro Thr Ile Ala Gly Lys Gly Thr Val Val Ser
1               5                   10                  15

Ser Ala Glu Cys
            20

<210> SEQ ID NO 38
<211> LENGTH: 19
<212> TYPE: PRT
<213> ORGANISM: Artificial Sequence
<220> FEATURE:
<223> OTHER INFORMATION: synthetic peptide

<400> SEQUENCE: 38

Thr Thr Leu Asn Pro Thr Ile Ala Gly Lys Gly Thr Val Val Ala Ser
1               5                   10                  15

Ser Ala Glu

<210> SEQ ID NO 39
<211> LENGTH: 21
<212> TYPE: PRT
<213> ORGANISM: Artificial Sequence
<220> FEATURE:
```

<223> OTHER INFORMATION: synthetic peptide

<400> SEQUENCE: 39

Cys Thr Thr Leu Asn Pro Thr Ile Ala Gly Lys Gly Thr Val Val Ala
1               5                   10                  15

Ser Ser Ala Glu Cys
            20

<210> SEQ ID NO 40
<211> LENGTH: 24
<212> TYPE: PRT
<213> ORGANISM: Artificial Sequence
<220> FEATURE:
<223> OTHER INFORMATION: synthetic peptide

<400> SEQUENCE: 40

Thr Thr Leu Asn Pro Thr Thr Leu Asn Pro Thr Ile Ala Gly Lys Gly
1               5                   10                  15

Thr Val Val Ala Ser Ser Ala Glu
            20

<210> SEQ ID NO 41
<211> LENGTH: 16
<212> TYPE: PRT
<213> ORGANISM: Artificial Sequence
<220> FEATURE:
<223> OTHER INFORMATION: synthetic peptide

<400> SEQUENCE: 41

Cys Thr Ile Ala Gly Lys Gly Thr Val Val Ala Ser Ser Ala Glu Cys
1               5                   10                  15

<210> SEQ ID NO 42
<211> LENGTH: 25
<212> TYPE: PRT
<213> ORGANISM: Artificial Sequence
<220> FEATURE:
<223> OTHER INFORMATION: synthetic peptide

<400> SEQUENCE: 42

Ala Glu Thr Ile Leu Asp Val Thr Thr Leu Asn Pro Thr Ile Ala Gly
1               5                   10                  15

Lys Gly Thr Val Val Thr Ser Ala Glu
            20                  25

<210> SEQ ID NO 43
<211> LENGTH: 27
<212> TYPE: PRT
<213> ORGANISM: Artificial Sequence
<220> FEATURE:
<223> OTHER INFORMATION: synthetic peptide

<400> SEQUENCE: 43

Cys Ala Glu Thr Ile Leu Asp Val Thr Thr Leu Asn Pro Thr Ile Ala
1               5                   10                  15

Gly Lys Gly Thr Val Val Thr Ser Ala Glu Cys
            20                  25

<210> SEQ ID NO 44
<211> LENGTH: 23
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (7)...(7)
<223> OTHER INFORMATION: Xaa = T or A
<220> FEATURE:
<221> NAME/KEY: VARIANT
<222> LOCATION: (8)...(8)
<223> OTHER INFORMATION: Xaa = T or D
<220> FEATURE:
<221> NAME/KEY: VARIANT
<222> LOCATION: (12)...(12)
<223> OTHER INFORMATION: Xaa = A or S
<220> FEATURE:
<221> NAME/KEY: VARIANT
<222> LOCATION: (13)...(13)
<223> OTHER INFORMATION: Xaa = V, T or A
<220> FEATURE:
<221> NAME/KEY: VARIANT
<222> LOCATION: 1, 23
<223> OTHER INFORMATION: Xaa = Any Amino Acid

<400> SEQUENCE: 44

Xaa Gly Ala Lys Pro Thr Xaa Xaa Thr Gly Asn Xaa Xaa Ala Pro Ser
1               5                   10                  15

Thr Leu Thr Ala Arg Glu Xaa
            20

<210> SEQ ID NO 45
<211> LENGTH: 25
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)...(4)
<223> OTHER INFORMATION: Xaa = A or D
<220> FEATURE:
<221> NAME/KEY: VARIANT
<222> LOCATION: (8)...(8)
<223> OTHER INFORMATION: Xaa = T, A or S
<220> FEATURE:
<221> NAME/KEY: VARIANT
<222> LOCATION: (9)...(9)
<223> OTHER INFORMATION: Xaa = T, D or A
<220> FEATURE:
<221> NAME/KEY: VARIANT
<222> LOCATION: (13)...(13)
<223> OTHER INFORMATION: Xaa = A or S
<220> FEATURE:
<221> NAME/KEY: VARIANT
<222> LOCATION: (14)...(14)
<223> OTHER INFORMATION: Xaa = V, T or A
<220> FEATURE:
<221> NAME/KEY: VARIANT
<222> LOCATION: (17)...(17)
<223> OTHER INFORMATION: Xaa = S or T
<220> FEATURE:
<221> NAME/KEY: VARIANT
<222> LOCATION: (19)...(19)
<223> OTHER INFORMATION: Xaa = L or C
<220> FEATURE:
<221> NAME/KEY: VARIANT
<222> LOCATION: 2, 24
<223> OTHER INFORMATION: Xaa = Any Amino Acid

<400> SEQUENCE: 45

Cys Xaa Gly Xaa Lys Pro Thr Xaa Xaa Thr Gly Asn Xaa Xaa Ala Pro
1               5                   10                  15

Xaa Thr Xaa Thr Ala Arg Glu Xaa Cys
            20                  25

<210> SEQ ID NO 46
<211> LENGTH: 21
<212> TYPE: PRT
<213> ORGANISM: Artificial Sequence

```
<220> FEATURE:
<223> OTHER INFORMATION: synthetic peptide

<400> SEQUENCE: 46

Gly Ala Lys Pro Thr Ala Thr Thr Gly Asn Ala Thr Ala Pro Ser Thr
1               5                   10                  15

Leu Thr Ala Arg Glu
            20

<210> SEQ ID NO 47
<211> LENGTH: 21
<212> TYPE: PRT
<213> ORGANISM: Artificial Sequence
<220> FEATURE:
<223> OTHER INFORMATION: synthetic peptide

<400> SEQUENCE: 47

Gly Ala Lys Pro Thr Ala Thr Thr Gly Asn Ala Thr Ala Pro Ser Thr
1               5                   10                  15

Leu Thr Ala Arg Glu
            20

<210> SEQ ID NO 48
<211> LENGTH: 23
<212> TYPE: PRT
<213> ORGANISM: Artificial Sequence
<220> FEATURE:
<223> OTHER INFORMATION: synthetic peptide

<400> SEQUENCE: 48

Cys Gly Ala Lys Pro Thr Ala Thr Thr Gly Asn Ala Thr Ala Pro Ser
1               5                   10                  15

Thr Leu Thr Ala Arg Glu Cys
            20

<210> SEQ ID NO 49
<211> LENGTH: 21
<212> TYPE: PRT
<213> ORGANISM: Artificial Sequence
<220> FEATURE:
<223> OTHER INFORMATION: synthetic peptide

<400> SEQUENCE: 49

Gly Ala Lys Pro Thr Thr Asp Thr Gly Asn Ser Ala Ala Pro Ser Thr
1               5                   10                  15

Leu Thr Ala Arg Glu
            20

<210> SEQ ID NO 50
<211> LENGTH: 23
<212> TYPE: PRT
<213> ORGANISM: Artificial Sequence
<220> FEATURE:
<223> OTHER INFORMATION: synthetic peptide

<400> SEQUENCE: 50

Cys Gly Ala Lys Pro Thr Thr Asp Thr Gly Asn Ser Ala Ala Pro Ser
1               5                   10                  15

Thr Leu Thr Ala Arg Glu Cys
            20

<210> SEQ ID NO 51
<211> LENGTH: 21
<212> TYPE: PRT
<213> ORGANISM: Artificial Sequence
```

```
<220> FEATURE:
<223> OTHER INFORMATION: synthetic peptide

<400> SEQUENCE: 51

Gly Ala Lys Pro Thr Thr Thr Thr Gly Asn Ala Val Ala Pro Ser Thr
 1               5                  10                  15

Leu Thr Ala Arg Glu
            20

<210> SEQ ID NO 52
<211> LENGTH: 23
<212> TYPE: PRT
<213> ORGANISM: Artificial Sequence
<220> FEATURE:
<223> OTHER INFORMATION: synthetic peptide

<400> SEQUENCE: 52

Cys Gly Ala Lys Pro Thr Thr Thr Thr Gly Asn Ala Val Ala Pro Ser
 1               5                  10                  15

Thr Leu Thr Ala Arg Glu Cys
            20

<210> SEQ ID NO 53
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (4)...(4)
<223> OTHER INFORMATION: Xaa = S or K
<220> FEATURE:
<221> NAME/KEY: VARIANT
<222> LOCATION: 1, 14
<223> OTHER INFORMATION: Xaa = Any Amino Acid

<400> SEQUENCE: 53

Xaa Thr Thr Xaa Asp Val Ala Gly Leu Gln Asn Asp Pro Xaa
 1               5                  10

<210> SEQ ID NO 54
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (5)...(5)
<223> OTHER INFORMATION: Xaa = S or K
<220> FEATURE:
<221> NAME/KEY: VARIANT
<222> LOCATION: 2, 15
<223> OTHER INFORMATION: Xaa = Any Amino Acid

<400> SEQUENCE: 54

Cys Xaa Thr Thr Xaa Asp Val Ala Gly Leu Gln Asn Asp Pro Xaa Cys
 1               5                  10                  15

<210> SEQ ID NO 55
<211> LENGTH: 4
<212> TYPE: PRT
<213> ORGANISM: Artificial Sequence
<220> FEATURE:
<223> OTHER INFORMATION: synthetic peptide

<400> SEQUENCE: 55

Gly Ala Ala Pro
 1
```

<210> SEQ ID NO 56
<211> LENGTH: 7
<212> TYPE: PRT
<213> ORGANISM: Artificial Sequence
<220> FEATURE:
<223> OTHER INFORMATION: synthetic peptide

<400> SEQUENCE: 56

Thr Thr Asn Val Ala Ala Pro
1               5

<210> SEQ ID NO 57
<211> LENGTH: 12
<212> TYPE: PRT
<213> ORGANISM: Artificial Sequence
<220> FEATURE:
<223> OTHER INFORMATION: synthetic peptide

<400> SEQUENCE: 57

Thr Thr Ser Asp Val Ala Gly Leu Gln Asn Asp Pro
1               5                   10

<210> SEQ ID NO 58
<211> LENGTH: 14
<212> TYPE: PRT
<213> ORGANISM: Artificial Sequence
<220> FEATURE:
<223> OTHER INFORMATION: synthetic peptide

<400> SEQUENCE: 58

Cys Thr Thr Ser Asp Val Ala Gly Leu Gln Asn Asp Pro Cys
1               5                   10

<210> SEQ ID NO 59
<211> LENGTH: 16
<212> TYPE: PRT
<213> ORGANISM: Artificial Sequence
<220> FEATURE:
<223> OTHER INFORMATION: synthetic peptide

<400> SEQUENCE: 59

Gly Ala Ala Pro Thr Thr Ser Asp Val Ala Gly Leu Gln Asn Asp Pro
1               5                   10                  15

<210> SEQ ID NO 60
<211> LENGTH: 18
<212> TYPE: PRT
<213> ORGANISM: Artificial Sequence
<220> FEATURE:
<223> OTHER INFORMATION: synthetic peptide

<400> SEQUENCE: 60

Cys Gly Ala Ala Pro Thr Thr Ser Asp Val Ala Gly Leu Gln Asn Asp
1               5                   10                  15

Pro Cys

<210> SEQ ID NO 61
<211> LENGTH: 19
<212> TYPE: PRT
<213> ORGANISM: Artificial Sequence
<220> FEATURE:
<223> OTHER INFORMATION: synthetic peptide

<400> SEQUENCE: 61

Thr Thr Ser Asp Val Ala Gly Leu Gln Asn Asp Pro Thr Thr Asn Val

```
                1               5                  10                 15
Ala Ala Pro

<210> SEQ ID NO 62
<211> LENGTH: 21
<212> TYPE: PRT
<213> ORGANISM: Artificial Sequence
<220> FEATURE:
<223> OTHER INFORMATION: synthetic peptide

<400> SEQUENCE: 62

Cys Thr Thr Ser Asp Val Ala Gly Leu Gln Asn Asp Pro Thr Thr Asn
1               5                  10                 15

Val Ala Ala Pro Cys
            20

<210> SEQ ID NO 63
<211> LENGTH: 23
<212> TYPE: PRT
<213> ORGANISM: Artificial Sequence
<220> FEATURE:
<223> OTHER INFORMATION: synthetic peptide

<400> SEQUENCE: 63

Gly Ala Ala Pro Thr Thr Ser Asp Val Ala Gly Leu Gln Asn Asp Pro
1               5                  10                 15

Thr Thr Asn Val Ala Ala Pro
            20

<210> SEQ ID NO 64
<211> LENGTH: 25
<212> TYPE: PRT
<213> ORGANISM: Artificial Sequence
<220> FEATURE:
<223> OTHER INFORMATION: synthetic peptide

<400> SEQUENCE: 64

Cys Gly Ala Ala Pro Thr Thr Ser Asp Val Ala Gly Leu Gln Asn Asp
1               5                  10                 15

Pro Thr Thr Asn Val Ala Ala Pro Cys
            20                  25

<210> SEQ ID NO 65
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)...(2)
<223> OTHER INFORMATION: Xaa = S or A
<220> FEATURE:
<221> NAME/KEY: VARIANT
<222> LOCATION: (15)...(15)
<223> OTHER INFORMATION: Xaa = K, Q, A or V
<220> FEATURE:
<221> NAME/KEY: VARIANT
<222> LOCATION: 1, 17
<223> OTHER INFORMATION: Xaa = Any Amino Acid

<400> SEQUENCE: 65

Xaa Xaa Glu Phe Thr Ile Asn Lys Pro Lys Gly Tyr Val Gly Xaa Glu
1               5                  10                 15

Xaa
```

```
<210> SEQ ID NO 66
<211> LENGTH: 15
<212> TYPE: PRT
<213> ORGANISM: Artificial Sequence
<220> FEATURE:
<223> OTHER INFORMATION: synthetic peptide

<400> SEQUENCE: 66

Ser Glu Phe Thr Ile Asn Lys Pro Lys Gly Tyr Val Gly Lys Glu
 1               5                  10                  15

<210> SEQ ID NO 67
<211> LENGTH: 15
<212> TYPE: PRT
<213> ORGANISM: Artificial Sequence
<220> FEATURE:
<223> OTHER INFORMATION: synthetic peptide

<400> SEQUENCE: 67

Ser Glu Phe Thr Ile Asn Lys Pro Lys Gly Tyr Val Gly Ala Glu
 1               5                  10                  15

<210> SEQ ID NO 68
<211> LENGTH: 15
<212> TYPE: PRT
<213> ORGANISM: Artificial Sequence
<220> FEATURE:
<223> OTHER INFORMATION: synthetic peptide

<400> SEQUENCE: 68

Ser Glu Phe Thr Ile Asn Lys Pro Lys Gly Tyr Val Gly Val Glu
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: synthetic peptide

<400> SEQUENCE: 69

Ala Glu Phe Thr Ile Asn Lys Pro Lys Gly Tyr Val Gly Gln Glu
 1               5                  10                  15

<210> SEQ ID NO 70
<211> LENGTH: 18
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 18
<223> OTHER INFORMATION: Xaa = Any Amino Acid

<400> SEQUENCE: 70

Xaa Ile Leu Trp Glu Gly Phe Gly Gly Asp Pro Cys Asp Pro Cys Thr
 1               5                  10                  15

Thr Xaa

<210> SEQ ID NO 71
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 12
```

<223> OTHER INFORMATION: Xaa = Any Amino Acid

<400> SEQUENCE: 71

Xaa Ala Leu Asn Ile Trp Asp Arg Phe Asp Val Xaa
1               5                   10

<210> SEQ ID NO 72
<211> LENGTH: 26
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 26
<223> OTHER INFORMATION: Xaa = Any Amino Acid

<400> SEQUENCE: 72

Xaa Lys Met Lys Ser Arg Lys Ser Cys Gly Ile Ala Val Gly Thr Thr
1               5                   10                  15

Val Ser Ala Asp Lys Tyr Ala Val Thr Xaa
            20                  25

<210> SEQ ID NO 73
<211> LENGTH: 6
<212> TYPE: PRT
<213> ORGANISM: Artificial Sequence
<220> FEATURE:
<223> OTHER INFORMATION: synthetic linker peptide

<400> SEQUENCE: 73

Ala Ala Ala Gly Gly Met
1               5

<210> SEQ ID NO 74
<211> LENGTH: 14
<212> TYPE: PRT
<213> ORGANISM: Artificial Sequence
<220> FEATURE:
<223> OTHER INFORMATION: synthetic linker peptide

<400> SEQUENCE: 74

Ala Ala Ala Gly Gly Met Pro Pro Ala Ala Ala Gly Gly Met
1               5                   10

<210> SEQ ID NO 75
<211> LENGTH: 6
<212> TYPE: PRT
<213> ORGANISM: Artificial Sequence
<220> FEATURE:
<223> OTHER INFORMATION: synthetic linker peptide

<400> SEQUENCE: 75

Ala Ala Ala Gly Gly Met
1               5

<210> SEQ ID NO 76
<211> LENGTH: 8
<212> TYPE: PRT
<213> ORGANISM: Artificial Sequence
<220> FEATURE:
<223> OTHER INFORMATION: synthetic linker peptide

<400> SEQUENCE: 76

Pro Pro Ala Ala Ala Gly Gly Met
1               5

```
<210> SEQ ID NO 77
<211> LENGTH: 5
<212> TYPE: PRT
<213> ORGANISM: Artificial Sequence
<220> FEATURE:
<223> OTHER INFORMATION: synthetic peptide

<400> SEQUENCE: 77

Ala Asp Thr Glu Ala
 1               5

<210> SEQ ID NO 78
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (8)...(8)
<223> OTHER INFORMATION: N = A or G
<220> FEATURE:
<221> NAME/KEY: misc_feature
<222> LOCATION: (9)...(9)
<223> OTHER INFORMATION: N = C or T
<220> FEATURE:
<221> NAME/KEY: misc_feature
<222> LOCATION: (12)...(12)
<223> OTHER INFORMATION: N = G or A
<220> FEATURE:
<221> NAME/KEY: misc_feature
<222> LOCATION: (13)...(13)
<223> OTHER INFORMATION: N = C or A
<220> FEATURE:
<221> NAME/KEY: misc_feature
<222> LOCATION: (17)...(17)
<223> OTHER INFORMATION: N = A or G
<220> FEATURE:
<221> NAME/KEY: misc_feature
<222> LOCATION: (18)...(18)
<223> OTHER INFORMATION: N = C or T
<220> FEATURE:
<221> NAME/KEY: misc_feature
<222> LOCATION: (21)...(21)
<223> OTHER INFORMATION: N = C or A
<220> FEATURE:
<221> NAME/KEY: misc_feature
<222> LOCATION: (29)...(29)
<223> OTHER INFORMATION: N = T or C
<220> FEATURE:
<221> NAME/KEY: misc_feature
<222> LOCATION: (30)...(30)
<223> OTHER INFORMATION: N = C or A
<220> FEATURE:
<221> NAME/KEY: misc_feature
<222> LOCATION: 1, 62
<223> OTHER INFORMATION: N = A, C, T, or G

<400> SEQUENCE: 78
ncctactnnc anngatnnag ngggcttann aaacgatcca acaacaaatg ttgctcgtcc      60 an                                                                    62

<210> SEQ ID NO 79
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 79
```

-continued

```
ncctactacc agcgatacag cgggcttatc aaacgatcca acaacaaatg ttgctcgtcc    60 an                                                                   62

<210> SEQ ID NO 80
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 80
ncctactgtc agcgatacag cgggcttatc aaacgatcca acaacaaatg ttgctcgtcc    60 an                                                                   62

<210> SEQ ID NO 81
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 81
ncctactacc aaggatacag cgggcttatc aaacgatcca acaacaaatg ttgctcgtcc    60 an                                                                   62

<210> SEQ ID NO 82
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 82
ncctactacc aacgatacag cgggcttatc aaacgatcca acaacaaatg ttgctcgtcc    60 an                                                                   62

<210> SEQ ID NO 83
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 83
ncctactacc agagatacag cgggcttatc aaacgatcca acaacaaatg ttgctcgtcc    60 an                                                                   62

<210> SEQ ID NO 84
<211> LENGTH: 62
<212> TYPE: DNA
```

```
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 84
ncctactacc agcgatgtag cgggcttatc aaacgatcca acaacaaatg ttgctcgtcc      60 an                                                                    62

<210> SEQ ID NO 85
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 62
<223> OTHER INFORMATION: n = A,T,C or G

<400> SEQUENCE: 85
ncctactacc agcgatgtag agggcttatc aaacgatcca acaacaaatg ttgctcgtcc      60 an                                                                    62

<210> SEQ ID NO 86
<211> LENGTH: 52
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 52
<223> OTHER INFORMATION: n = A,T,C or G

<400> SEQUENCE: 86
ngcgatacag cgggcttatc aaacgatcca acaacaaatg ttgctcgtcc an              52

<210> SEQ ID NO 87
<211> LENGTH: 42
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 42
<223> OTHER INFORMATION: n = A,T,C or G

<400> SEQUENCE: 87
ngggcttatc aaacgatcca acaacaaatg ttgctcgtcc an                        42

<210> SEQ ID NO 88
<211> LENGTH: 32
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 32
<223> OTHER INFORMATION: n = A,T,C or G

<400> SEQUENCE: 88
naacgatcca acaacaaatg ttgctcgtcc an                                   32
```

<210> SEQ ID NO 89
<211> LENGTH: 22
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 22
<223> OTHER INFORMATION: n = A,T,C or G

<400> SEQUENCE: 89
ncaacaaatg ttgctcgtcc an                                      22

<210> SEQ ID NO 90
<211> LENGTH: 44
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 44
<223> OTHER INFORMATION: n = A,T,C or G

<400> SEQUENCE: 90
nacattggga gcaactaccg gttatttaaa aggaaactcc gctn               44

<210> SEQ ID NO 91
<211> LENGTH: 32
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 32
<223> OTHER INFORMATION: n = A,T,C or G

<400> SEQUENCE: 91
nacattggga gcaactaccg gttatttaaa an                            32

<210> SEQ ID NO 92
<211> LENGTH: 35
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 35
<223> OTHER INFORMATION: n = A,T,C or G

<400> SEQUENCE: 92
ntgtacattg ggagcaacta ccggttattt aaaan                         35

<210> SEQ ID NO 93
<211> LENGTH: 62
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (24)...(24)
<223> OTHER INFORMATION: N = C or T
<220> FEATURE:
<221> NAME/KEY: misc_feature
<222> LOCATION: 1, 62
<223> OTHER INFORMATION: n = A,T,C or G -continued

<400> SEQUENCE: 93
naagccgaaa ggatatgttg gggnggaatt tccacttgat attaccgcag gaacagaagc    60 tn                                                                  62

<210> SEQ ID NO 94
<211> LENGTH: 41
<212> TYPE: DNA
<213> ORGANISM: Artificial Sequence
<220> FEATURE:
<223> OTHER INFORMATION: synthetic oligonucleotide probe

<400> SEQUENCE: 94
aagccgaaag gatatgttgg ggcggaattt ccacttgata t                       41

<210> SEQ ID NO 95
<211> LENGTH: 41
<212> TYPE: DNA
<213> ORGANISM: Artificial Sequence
<220> FEATURE:
<223> OTHER INFORMATION: synthetic oligonucleotide probe

<400> SEQUENCE: 95
aagccgaaag gatatgttgg ggtggaattt ccacttgata t                       41

<210> SEQ ID NO 96
<211> LENGTH: 45
<212> TYPE: DNA
<213> ORGANISM: Artificial Sequence
<220> FEATURE:
<223> OTHER INFORMATION: synthetic oligonucleotide probe

<400> SEQUENCE: 96
gttggggcgg aatttccact tgatattacc gcaggaacag aagct                   45

<210> SEQ ID NO 97
<211> LENGTH: 45
<212> TYPE: DNA
<213> ORGANISM: Artificial Sequence
<220> FEATURE:
<223> OTHER INFORMATION: synthetic oligonucleotide probe

<400> SEQUENCE: 97
gttggggtgg aatttccact tgatattacc gcaggaacag aagct                   45

<210> SEQ ID NO 98
<211> LENGTH: 50
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (14)...(14)
<223> OTHER INFORMATION: N = A or G
<220> FEATURE:
<221> NAME/KEY: misc_feature
<222> LOCATION: (15)...(15)
<223> OTHER INFORMATION: N = G or C
<220> FEATURE:
<221> NAME/KEY: misc_feature
<222> LOCATION: (23)...(23)
<223> OTHER INFORMATION: N = G or T
<220> FEATURE:
<221> NAME/KEY: misc_feature
<222> LOCATION: (29)...(29)
<223> OTHER INFORMATION: N = G or T
<220> FEATURE:
<221> NAME/KEY: misc_feature
<222> LOCATION: (30)...(30)

```
<223> OTHER INFORMATION: N = G or C
<220> FEATURE:
<221> NAME/KEY: misc_feature
<222> LOCATION: (31)...(31)
<223> OTHER INFORMATION: N = C or A
<220> FEATURE:
<221> NAME/KEY: misc_feature
<222> LOCATION: (37)...(37)
<223> OTHER INFORMATION: N = A or T
<220> FEATURE:
<221> NAME/KEY: misc_feature
<222> LOCATION: (43)...(43)
<223> OTHER INFORMATION: N = A or C
<220> FEATURE:
<221> NAME/KEY: misc_feature
<222> LOCATION: 1, 50
<223> OTHER INFORMATION: n = A,T,C or G

<400> SEQUENCE: 98
ngctggtaaa gganntgtgg tcncttccnn nagcganaac ganctggctn            50

<210> SEQ ID NO 99
<211> LENGTH: 48
<212> TYPE: DNA
<213> ORGANISM: Artificial Sequence
<220> FEATURE:
<223> OTHER INFORMATION: synthetic oligonucleotide probe

<400> SEQUENCE: 99
gctggtaaag gaagtgtggt cgcttccggc agcgaaaacg aactggct              48

<210> SEQ ID NO 100
<211> LENGTH: 48
<212> TYPE: DNA
<213> ORGANISM: Artificial Sequence
<220> FEATURE:
<223> OTHER INFORMATION: synthetic oligonucleotide probe

<400> SEQUENCE: 100
gctggtaaag gagctgtggt ctcttccgga agcgataacg aactggct              48

<210> SEQ ID NO 101
<211> LENGTH: 53
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (5)...(5)
<223> OTHER INFORMATION: N = A or G
<220> FEATURE:
<221> NAME/KEY: misc_feature
<222> LOCATION: (6)...(6)
<223> OTHER INFORMATION: N = C or G
<220> FEATURE:
<221> NAME/KEY: misc_feature
<222> LOCATION: (8)...(8)
<223> OTHER INFORMATION: N = A or G
<220> FEATURE:
<221> NAME/KEY: misc_feature
<222> LOCATION: (9)...(9)
<223> OTHER INFORMATION: N = C or A
<220> FEATURE:
<221> NAME/KEY: misc_feature
<222> LOCATION: (20)...(20)
<223> OTHER INFORMATION: N = G or A
<220> FEATURE:
<221> NAME/KEY: misc_feature
<222> LOCATION: (21)...(21)
<223> OTHER INFORMATION: N = C or G
<220> FEATURE:
<221> NAME/KEY: misc_feature
<222> LOCATION: (23)...(23)
```

```
<223> OTHER INFORMATION: N = G or A
<220> FEATURE:
<221> NAME/KEY: misc_feature
<222> LOCATION: (24)...(24)
<223> OTHER INFORMATION: N = T or C
<220> FEATURE:
<221> NAME/KEY: misc_feature
<222> LOCATION: (38)...(38)
<223> OTHER INFORMATION: N = C or T
<220> FEATURE:
<221> NAME/KEY: misc_feature
<222> LOCATION: (39)...(39)
<223> OTHER INFORMATION: N = T or G
<220> FEATURE:
<221> NAME/KEY: misc_feature
<222> LOCATION: 1, 53
<223> OTHER INFORMATION: n = A,T,C or G

<400> SEQUENCE: 101
nacanntnnt acaggcaatn ntnnagctcc atccactnnt acagcaagag agn          53

<210> SEQ ID NO 102
<211> LENGTH: 51
<212> TYPE: DNA
<213> ORGANISM: Artificial Sequence
<220> FEATURE:
<223> OTHER INFORMATION: synthetic oligonucleotide probe

<400> SEQUENCE: 102
acaactacta caggcaatgc tgtagctcca tccactctta cagcaagaga g            51

<210> SEQ ID NO 103
<211> LENGTH: 51
<212> TYPE: DNA
<213> ORGANISM: Artificial Sequence
<220> FEATURE:
<223> OTHER INFORMATION: synthetic oligonucleotide probe

<400> SEQUENCE: 103
acagctacta caggcaatgc tacagctcca tccactctta cagcaagaga g            51

<210> SEQ ID NO 104
<211> LENGTH: 51
<212> TYPE: DNA
<213> ORGANISM: Artificial Sequence
<220> FEATURE:
<223> OTHER INFORMATION: synthetic oligonucleotide probe

<400> SEQUENCE: 104
acaactgata caggcaatag tgcagctcca tccactctta cagcaagaga g            51

<210> SEQ ID NO 105
<211> LENGTH: 51
<212> TYPE: DNA
<213> ORGANISM: Artificial Sequence
<220> FEATURE:
<223> OTHER INFORMATION: synthetic oligonucleotide probe

<400> SEQUENCE: 105
acaactgcta caggcaatgc tgcagctcca tccacttgta cagcaagaga g            51

<210> SEQ ID NO 106
<211> LENGTH: 47
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: (13)...(13)
```

```
<223> OTHER INFORMATION: N = T or G
<220> FEATURE:
<221> NAME/KEY: misc_feature
<222> LOCATION: (20)...(20)
<223> OTHER INFORMATION: N = A or G
<220> FEATURE:
<221> NAME/KEY: misc_feature
<222> LOCATION: (23)...(23)
<223> OTHER INFORMATION: N = A or G
<220> FEATURE:
<221> NAME/KEY: misc_feature
<222> LOCATION: (24)...(24)
<223> OTHER INFORMATION: N = G or A
<220> FEATURE:
<221> NAME/KEY: misc_feature
<222> LOCATION: (26)...(26)
<223> OTHER INFORMATION: N = G or A
<220> FEATURE:
<221> NAME/KEY: misc_feature
<222> LOCATION: 1, 47
<223> OTHER INFORMATION: n = A,T,C or G

<400> SEQUENCE: 106
nggagctggc gangtgaaan ctnncncaga gggtcagctc ggagacn          47

<210> SEQ ID NO 107
<211> LENGTH: 45
<212> TYPE: DNA
<213> ORGANISM: Artificial Sequence
<220> FEATURE:
<223> OTHER INFORMATION: synthetic oligonucleotide probe

<400> SEQUENCE: 107
ggagctggcg atgtgaaaac tagcgcagag ggtcagctcg gagac           45

<210> SEQ ID NO 108
<211> LENGTH: 45
<212> TYPE: DNA
<213> ORGANISM: Artificial Sequence
<220> FEATURE:
<223> OTHER INFORMATION: synthetic oligonucleotide probe

<400> SEQUENCE: 108
ggagctggcg aggtgaaagc taacgcagag ggtcagctcg gagac           45

<210> SEQ ID NO 109
<211> LENGTH: 45
<212> TYPE: DNA
<213> ORGANISM: Artificial Sequence
<220> FEATURE:
<223> OTHER INFORMATION: synthetic oligonucleotide probe

<400> SEQUENCE: 109
ggagctggcg atgtgaaaac tggcacagag ggtcagctcg gagac           45

<210> SEQ ID NO 110
<211> LENGTH: 44
<212> TYPE: DNA
<213> ORGANISM: Artificial Sequence
<220> FEATURE:
<223> OTHER INFORMATION: synthetic oligonucleotide probe

<400> SEQUENCE: 110
ggagctggcg atgtgaaagt agcgcagagg gtcagctcgg agac            44

<210> SEQ ID NO 111
<211> LENGTH: 77
<212> TYPE: DNA
<213> ORGANISM: Artificial Sequence
<220> FEATURE:
```

-continued

<223> OTHER INFORMATION: synthetic oligonucleotide probe
<220> FEATURE:
<221> NAME/KEY: misc_feature
<222> LOCATION: 1, 77
<223> OTHER INFORMATION: n = A,T,C or G

<400> SEQUENCE: 111
natgggcgag gctttagccg gagcttctgg gaatacgacc tctactcttt caaaattggt    60
agaacgaacg aaccctn                                                  77

<210> SEQ ID NO 112
<211> LENGTH: 69
<212> TYPE: DNA
<213> ORGANISM: Artificial Sequence
<220> FEATURE:
<223> OTHER INFORMATION: synthetic oligonucleotide probe

<400> SEQUENCE: 112
ggcgaggctt tagccggagc ttctgggaat acgacctcta ctctttcaaa attggtagaa    60
cgaacgaac                                                           69

<210> SEQ ID NO 113
<211> LENGTH: 42
<212> TYPE: DNA
<213> ORGANISM: Artificial Sequence
<220> FEATURE:
<223> OTHER INFORMATION: synthetic oligonucleotide probe

<400> SEQUENCE: 113
aatacgacct ctactctttc aaaattggta gaacgaacga ac                      42

<210> SEQ ID NO 114
<211> LENGTH: 30
<212> TYPE: DNA
<213> ORGANISM: Artificial Sequence
<220> FEATURE:
<223> OTHER INFORMATION: synthetic oligonucleotide probe

<400> SEQUENCE: 114
atgggcgagg ctttagccgg agcttctggg                                    30

<210> SEQ ID NO 115
<211> LENGTH: 26
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 26
<223> OTHER INFORMATION: n = A,T,C or G

<400> SEQUENCE: 115
natgggtgac aagcctacaa gtactn                                        26

<210> SEQ ID NO 116
<211> LENGTH: 23
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 23
<223> OTHER INFORMATION: n = A,T,C or G

<400> SEQUENCE: 116
ngtcaaaacg aattctgtac can            23

<210> SEQ ID NO 117
<211> LENGTH: 20
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 20
<223> OTHER INFORMATION: n = A,T,C or G

<400> SEQUENCE: 117
ngcactcata gcaggaactn            20

<210> SEQ ID NO 118
<211> LENGTH: 17
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 17
<223> OTHER INFORMATION: n = A,T,C or G

<400> SEQUENCE: 118
ncttacagca ggaacan            17

<210> SEQ ID NO 119
<211> LENGTH: 17
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 17
<223> OTHER INFORMATION: n = A,T,C or G

<400> SEQUENCE: 119
ncttacatca ggaacan            17

<210> SEQ ID NO 120
<211> LENGTH: 20
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 20
<223> OTHER INFORMATION: n = A,T,C or G

<400> SEQUENCE: 120
ngtcaaaaag gatgctgtan            20

<210> SEQ ID NO 121
<211> LENGTH: 23
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 23
<223> OTHER INFORMATION: n = A,T,C or G

<400> SEQUENCE: 121

```
nggcgaggtg aaagctaacg can                                            23

<210> SEQ ID NO 122
<211> LENGTH: 20
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 20
<223> OTHER INFORMATION: n = A,T,C or G

<400> SEQUENCE: 122
nccagtagta aatgttgctn                                                20

<210> SEQ ID NO 123
<211> LENGTH: 17
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 17
<223> OTHER INFORMATION: n = A,T,C or G

<400> SEQUENCE: 123
ntctggcttt gatacan                                                   17

<210> SEQ ID NO 124
<211> LENGTH: 20
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 20
<223> OTHER INFORMATION: n = A,T,C or G

<400> SEQUENCE: 124
nccaacaata aacgttgctn                                                20

<210> SEQ ID NO 125
<211> LENGTH: 17
<212> TYPE: DNA
<213> ORGANISM: Artificial Sequence
<220> FEATURE:
<223> OTHER INFORMATION: synthetic oligonucleotide probe
<220> FEATURE:
<221> NAME/KEY: misc_feature
<222> LOCATION: 1, 17
<223> OTHER INFORMATION: n = A,T,C or G

<400> SEQUENCE: 125
ntctgccgga accgatn                                                   17

<210> SEQ ID NO 126
<211> LENGTH: 25
<212> TYPE: DNA
<213> ORGANISM: Artificial Sequence
<220> FEATURE:
<223> OTHER INFORMATION: synthetic primer

<400> SEQUENCE: 126
tgaaaaaact cttgaaatcg gtatt                                          25

<210> SEQ ID NO 127
```

```
<211> LENGTH: 33
<212> TYPE: DNA
<213> ORGANISM: Artificial Sequence
<220> FEATURE:
<223> OTHER INFORMATION: synthetic primer

<400> SEQUENCE: 127
tacggtacct tagaagcgga attgtgcatt tac                          33

<210> SEQ ID NO 128
<211> LENGTH: 45
<212> TYPE: DNA
<213> ORGANISM: Artificial Sequence
<220> FEATURE:
<223> OTHER INFORMATION: synthetic primer

<400> SEQUENCE: 128
tgtaaaacga cggccagtgc cgtattagtg tttgccgctt tgagt             45

<210> SEQ ID NO 129
<211> LENGTH: 21
<212> TYPE: DNA
<213> ORGANISM: Artificial Sequence
<220> FEATURE:
<223> OTHER INFORMATION: synthetic primer

<400> SEQUENCE: 129
catcgtagtc aatagaggca t                                       21

<210> SEQ ID NO 130
<211> LENGTH: 6
<212> TYPE: PRT
<213> ORGANISM: Artificial Sequence
<220> FEATURE:
<223> OTHER INFORMATION: synthetic peptide

<400> SEQUENCE: 130

Ala Gly Thr Glu Ala Ala
 1               5

<210> SEQ ID NO 131
<211> LENGTH: 6
<212> TYPE: PRT
<213> ORGANISM: Artificial Sequence
<220> FEATURE:
<223> OTHER INFORMATION: synthetic peptide

<400> SEQUENCE: 131

Ala Gly Thr Asp Ala Ala
 1               5

<210> SEQ ID NO 132
<211> LENGTH: 28
<212> TYPE: PRT
<213> ORGANISM: Artificial Sequence
<220> FEATURE:
<223> OTHER INFORMATION: synthetic peptide

<400> SEQUENCE: 132

Cys Ala Glu Thr Ile Phe Asp Val Thr Thr Leu Asn Pro Thr Ile Ala
 1               5                  10                  15

Gly Ala Gly Asp Val Lys Thr Ser Ala Glu Gly Cys
             20                  25

<210> SEQ ID NO 133
<211> LENGTH: 25
<212> TYPE: PRT
```

<213> ORGANISM: Artificial Sequence
<220> FEATURE:
<223> OTHER INFORMATION: synthetic peptide

<400> SEQUENCE: 133

Lys Met Lys Ser Arg Lys Ser Cys Gly Ile Ala Val Gly Thr Thr Val
1               5                   10                  15

Val Ser Ala Asp Lys Tyr Ala Val Thr
            20                  25

<210> SEQ ID NO 134
<211> LENGTH: 1182
<212> TYPE: DNA
<213> ORGANISM: Chlamydia trachomatis

<400> SEQUENCE: 134

```
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggtttcg gcggagatcc ttgcgatcct tgcaccactt ggtgtgacgc tatcagcatg     180
cgtataggtt actatggtga ctttgttttc gaccgtgttt tgaaaacaga tgtgaataaa     240
gaattccaaa tgggtgccaa gcctacaact actacaggca atgctgcagc tccatccact     300
cttacagcaa gagagaatcc tgcttacggc cgacatatgc aggatgctga tgtttaca     360 aatgccgctt gcatggcatt gaatatttgg gatcgctttg atgtattctg tacactagga     420
gcctctagcg ataccttaa aggaaactct gcttctttca atttagtggg gttattcgga     480
aataatgaga accagactaa agtttcaaat ggtacgtttg taccaaatat gagcttagat     540
caatctgttg ttgagttgta tacagatact gcttttgcgt ggagcgtcgg cgctcgcgca     600
gctttgtggg aatgtggatg tgcaacttta ggagcttctt tccaatatgc tcaatctaaa     660
cctaaagtag aagaattaaa cgttctctgc aatgcagcag agtttactat taataaaccct    720 aaagggtatg taggtaagga gttgcctctt gatcttacag caggaacaga tgctgcgaca     780
ggaactaagg atgcctctat tgattaccat gaatggcaag caagtttagc tctctcttac     840
agattgaata tgttcactcc ttacattgga gttaaatggt ctcgagcaag ctttgatgca     900
gacacgattc gtattgctca gccgaagtca gccgagacta tctttgatgt taccactctg     960
aacccaacta ttgctggagc tggcgatgtg aaaactagcg cagagggtca gctcggagac    1020
acaatgcaaa tcgtctcctt gcaattgaac aagatgaaat ctagaaaatc ttgcggtatt    1080
gcagtaggaa caactattgt ggatgcagac aaatacgcaa ttacagttga gactcgcttg    1140
atcgatgaga gagctgctca cgtaaatgca caattccgct tc                        1182
```

<210> SEQ ID NO 135
<211> LENGTH: 1182
<212> TYPE: DNA
<213> ORGANISM: Chlamydia trachomatis

<400> SEQUENCE: 135

```
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggtttcg gcggagatcc ttgcgatcct tgcaccactt ggtgtgacgc tatcagcatg     180
cgtatgggtt actatggtga ctttgttttc gaccgtgttt tgaaaacaga tgtgaataaa     240
gaattccaaa tgggtgccaa gcctacagct actacaggca atgctacagc tccatccact     300
cttacagcaa gagagaatcc tgcttacggc cgacatatgc aggatgctga tgtttaca     360
```

```
aatgccgctt gcatggcatt gaatatttgg gatcgctttg atgtattctg tacactagga    420
gcctctagcg gataccttaa aggaaactct gcttctttca atttagtggg gttattcgga    480
aataatgaga accagactaa agtttcaaat ggtacgtttg taccaaatat gagcttagat    540
caatctgttg ttgagttgta tacagatact gcttttgcgt ggagcgtcgg cgctcgcgca    600
gctttgtggg aatgtggatg tgcaacttta ggagcttctt tccaatatgc tcaatctaaa    660
cctaaagtag aagaattaaa cgttctctgc aatgcagcag agtttactat taataaacct    720
aaagggtatg taggtaagga gttgcctctt gatcttacag caggaacaga tgctgcgaca    780
ggaactaagg atgcctctat tgattaccat gaatggcaag caagtttagc tctctcttac    840
agattgaata tgttcactcc ttacattgga gttaaatggt ctcgagcaag ctttgatgca    900
gacacgattc gtattgctca gccgaagtca gccgagacta tctttgatgt taccactctg    960
aacccaacta ttgctggagc tggcgatgtg aaaactagcg cagagggtca gctcggagac   1020
acaatgcaaa tcgtctcctt gcaattgaac aagatgaaat ctagaaaatc ttgcggtatt   1080
gcagtaggaa caactattgt ggatgcagac aaatacgcag ttacagttga gactcgcttg   1140
atcgatgaga gagctgctca cgtaaatgca caattccgct tc                      1182
```

<210> SEQ ID NO 136
<211> LENGTH: 1179
<212> TYPE: DNA
<213> ORGANISM: Chlamydia trachomatis

<400> SEQUENCE: 136

```
atgaaaaaac tcttgaaatc ggtattagta tttgccgctt tgagttctgc ttcctccttg     60
caagctctgc ctgtggggaa tcctgctgaa ccaagcctta tgatcgacgg aattctgtgg    120
gaaggtttcg gtggagatcc ttgcgatcct tgcaccactt ggtgtgacgc tatcagcatg    180
cgtatgggtt actatggaga ctttgttttc gaccgtgttt tggaaacaga tgtgaataaa    240
gaattccaca tgggtgccaa gcctacagct gatacaggca atagtacagc tccatccact    300
cttacagcaa gagagaatcc tgcttacggc cgacatatgc aggatgctga tgtgtttaca    360
aatgccgctt gcatggcatt gaatatttgg gatcgttttg atgtattctg tacattagga    420
gccaccagtg gatatcttaa aggaaactct gcttctttca atttagttgg attgtttgga    480
gataatgaaa tcaaaaaac ggtcaaaacg aagtctgtac caaatatgag ctttgatcaa    540
tctgttgttg agttgtatac agatactact tttgcgtgga gcgtcggcgc tcgcgcagct    600
ttgtgggaat gtggatgtgc aactttagga gcttcattcc aatatgctca atctaaacct    660
aaagtagaag aattaaacgt tctctgcaat gcagcagagt ttactattaa taaacctaaa    720
gggtatgtag gtaaggagtt tcctcttgat cttacatcag aacagatgc tgcgacagga    780
actaaggatg cctctattga ttaccatgaa tggcaagcaa gtttagctct ctcttacaga    840
ctgaatatgt tcactcccta cattggagtt aaatggtctc gagcaagctt tgatgccgat    900
acgattcgta tagcccagcc aaaatcagct acagctattt ttgatactac cacgcttaac    960
ccaactattg ctggagctgg cgatgtgaaa actggcgcag agggtcagct cggagacaca   1020
atgcaaatcg tttccttgca attgaacaag atgaaatcta gaaaatcttg cggtattgca   1080
gtaggaacaa ctattgtgga tgcagacaaa tacgcagtta cagttgagac tcgcttgatc   1140
gatgagagag cagctcacgt aaatgcacaa ttccgcttc                           1179
```

<210> SEQ ID NO 137
<211> LENGTH: 1179
<212> TYPE: DNA

<213> ORGANISM: Chlamydia trachomatis

<400> SEQUENCE: 137

| | |
|---|---|
| atgaaaaaac tcttgaaatc ggtattagta tttgccgctt tgagttctgc ttcctccttg | 60 |
| caagctctgc ctgtggggaa tcctgctgaa ccaagcctta tgatcgacgg aattctgtgg | 120 |
| gaaggtttcg gtggagatcc ttgcgatcct tgcaccactt ggtgtgacgc tatcagcatg | 180 |
| cgtatgggtt actatggaga ctttgttttc gaccgtgttt tggaaacaga tgtgaataaa | 240 |
| gaattccaca tgggtgccaa gcctacagct gatacaggca atagtacagc tccatccact | 300 |
| cttacagcaa gagagaatcc tgcttacggc cgacatatgc aggatgctga gatgtttaca | 360 |
| aatgccgctt gcatggcatt gaatatttgg gatcgttttg atgtattctg tacattagga | 420 |
| gccaccagtg gatatcttaa aggaaactct gcttctttca atttagttgg attgtttgga | 480 |
| gataatgaaa atcaaaaaac ggtcaaaacg aagtctgtac caaatatgag ctttgatcaa | 540 |
| tctgttgttg agttgtatac agatactact tttgcgtgga gcgtcggcgc tcgcgcagct | 600 |
| ttgtgggaat gtggatgtgc aactttagga gcttcattcc aatatgctca atctaaacct | 660 |
| aaagtagaag aattaaacgt tctctgcaat gcagcagagt ttactattaa taaacctaaa | 720 |
| gggtatgtag gtaaggagtt tcctcttgat cttacatcag gaacagatgc tgcgacagga | 780 |
| actaaggatg cctctattga ttaccatgaa tggcaagcaa gtttagctct ctcttacaga | 840 |
| ctgaatatgt tcactcccta cattggagtt aaatggtctc gagcaagctt tgatgccgat | 900 |
| acgattcgta tagcccagcc aaaatcagct cagctatttt ttgatactac cacgcttaac | 960 |
| ccaactattg ctggagctgg cgatgtgaaa actggcacag agggtcagct cggagacaca | 1020 |
| atgcaaatcg tttccttgca attgaacaag atgaaatcta gaaaatcttg cggtattgca | 1080 |
| gtaggaacaa ctattgtgga tgcagacaaa tacgcagtta cagttgagac tcgcttgatc | 1140 |
| gatgagagag cagctcacgt aaatgcacaa ttccgcttc | 1179 |

<210> SEQ ID NO 138
<211> LENGTH: 1179
<212> TYPE: DNA
<213> ORGANISM: Chlamydia trachomatis

<400> SEQUENCE: 138

| | |
|---|---|
| atgaaaaaac tcttgaaatc ggtattagta tttgccgctt tgagttctgc ttcctccttg | 60 |
| caagctctgc ctgtggggaa tcctgctgaa ccaagcctta tgatcgacgg aattctgtgg | 120 |
| gaaggtttcg gtggagatcc ttgcgatcct tgcaccactt ggtgtgacgc tatcagcatg | 180 |
| cgtatgggtt actatggaga ctttgttttc gaccgtgttt tggaaacaga tgtgaataaa | 240 |
| gaattccaca tgggtgacaa gcctacaggt gatacaggca atagtacagc tccaaccact | 300 |
| cttacagcaa gagagaatcc tgcttacggc cgacatatgc aggatgctga gatgtttaca | 360 |
| aatgccgctt gcatggcatt gaatatttgg gatcgttttg atgtattctg tacattagga | 420 |
| gccaccagtg gatatcttaa aggaaactct gcttctttca atttagttgg attgtttgga | 480 |
| gataatgaaa atcaaagcac ggtcaaaacg aattctgtac caaatatgag ctttgatcaa | 540 |
| tctgttgttg aactttacac agatactacc ttctcttgga gcgtgggcgc tcgagcagct | 600 |
| ttgtgggagt gcggatgtgc gactttaggg gcttcattcc aatacgctca atctaaacct | 660 |
| aaagtcgaag aattaaacgt tctctgtaac gcagctgagt ttactatcaa taagcctaaa | 720 |
| ggatatgtag gcaagaatt cctcttgca ctcatatcag gaactgatgc agcgacgggc | 780 |
| actaaagatg cctctattga ttaccatgag tggcaagcaa gtttagctct ctcttacaga | 840 |

| ctgaatatgt tcactcccta cattggagtt aaatggtctc gagcaagttt tgatgccgat | 900 |
| acgattcgta tagcccagcc aaaatcagct acagctattt ttgatactac cacgcttaac | 960 |
| ccaactattg ctggagctgg cgatgtgaaa gctggcacag agggtcagct cggagatacc | 1020 |
| atgcaaatcg tttccttgca attgaacaag atgaaatcta gaaaatcttg cggtattgca | 1080 |
| gtaggaacga ctattgtaga tgcagacaaa tacgcagtta cagttgagac tcgcttgatc | 1140 |
| gatgagagag cagctcacgt aaatgcacaa ttccgcttc | 1179 |

<210> SEQ ID NO 139
<211> LENGTH: 1179
<212> TYPE: DNA
<213> ORGANISM: Chlamydia trachomatis

<400> SEQUENCE: 139

| atgaaaaaac tcttgaaatc ggtattagtg tttgccgctt tgagttctgc ttcctccttg | 60 |
| caagctctgc ctgtggggaa tcctgctgaa ccaagcctta tgatcgacgg aattctatgg | 120 |
| gaaggtttcg gtggagatcc ttgcgatcct tgcaccactt ggtgtgacgc tatcagcatg | 180 |
| cgtatgggtt actatggaga ctttgttttc gaccgtgttt tgcaaacaga gtgaataaa | 240 |
| gaattccaca tgggtgacaa gcctacaggt gatacaggca atagtacagc tccaaccact | 300 |
| tgtacagcaa gagagaatcc tgcttacggc cgacatatgc aggatgctga gatgtttaca | 360 |
| aatgctgctt acatggcatt gaatatttgg gatcgttttg atgtattctg tacattagga | 420 |
| gccaccagtg gatatcttaa aggaaattca gcatctttca acttagttgg attgtttgga | 480 |
| gataatgaaa atcaaagcac ggtcaaaacg aatgctgtac caaatatgag ctttgatcaa | 540 |
| tctgttgttg aactttacac agatactacc ttctcttgga gcgtgggcgc tcgagcagct | 600 |
| ttgtgggagt gcggatgtgc gactttaggg gcttcattcc aatacgctca atctaaacct | 660 |
| aaagtcgaag aattaaacgt tctctgtaac gcagctgagt ttactatcaa taagcctaaa | 720 |
| ggatatgtag ggcaagaatt tcctcttgca ctcatatcag gaactgatgc agcgacgggc | 780 |
| actaaagatg cctctattga ttaccatgag tggcaagcaa gtttagctct ctcttacaga | 840 |
| ctgaatatgt tcactcccta cattggagtt aaatggtctc gagcaagttt tgatgccgat | 900 |
| acgattcgta tagcccagcc aaaattagct acagctattt ttgatactac cacgcttaac | 960 |
| ccaactattg ctggagctgg cgaggtgaaa gctgacacag agggtcagct cggagatacc | 1020 |
| atgcaaatcg tttccttgca attgaacaag atgaaatcta gaaaatcttg cggtattgca | 1080 |
| gtaggaacga ctattgtaga tgcagacaaa tacgcagtta cagttgagac tcgcttgatc | 1140 |
| gatgagagag cagctcacgt aaatgcacaa ttccgcttc | 1179 |

<210> SEQ ID NO 140
<211> LENGTH: 1182
<212> TYPE: DNA
<213> ORGANISM: Chlamydia trachomatis

<400> SEQUENCE: 140

| atgaaaaaac tcttgaaatc ggtattagtg tttgccgctt tgagttctgc ttcctccttg | 60 |
| caagctctgc ctgtggggaa tcctgctgaa ccaagcctta tgatcgacgg aattctatgg | 120 |
| gaaggtttcg gtggagatcc ttgcgatcct tgcaccactt ggtgtgacgc tatcagcatg | 180 |
| cgtatgggtt actatggaga ctttgttttc gaccgtgttt tgcaaacaga gtgaataaa | 240 |
| gaattccaca tgggtgacaa gcctacaggt gatacaggca atagtacagc tccaaccact | 300 |
| tgtacagcaa gagagaatcc tgcttacggc cgacatatgc aggatgctga gatgtttaca | 360 | aatgctgctt acatggcatt gaatatttgg gatcgttttg atgtattctg tacattagga 420 gccaccagtg gatatcttaa aggaaattca gcatctttca acttagttgg cttgtttgga 480 gataatgaaa atcatggcac ggttgtcgaa acgaatcctg taccaaatat gagctttgat 540 caatctgttg ttgaacttta cacagatact accttctctt ggagtgctgg agctcgtgca 600 gctttgtggg agtgcggatg cgcgacttta ggcgcttcat tccaatacgc tcaatccaag 660 cctaaagtcg aagaattaaa cgttctctgt aacgcagctg agtttactat caataagcct 720 aaaggatatg tagggcaaga attccctctt gcactcaaat caggaactga tggagtgacg 780 ggcactaaag atgcctctat tgattaccat gagtggcaag caagtttagc tctctcttac 840 agactgaata tgttcactcc ctacattgga gttaaatggt ctcgagcaag ttttgatgcg 900 gatacgattc gtatagccca gccaaaatta gctacagctg tttttgatac taccacgctt 960 aacccaacta ttgctggagc tggcgaggtg aaagctgaca cagagggtca gctcggagat 1020 accatgcaaa tcgtttcctt gcaattgaac aagatgaaat ctagaaaatc ttgcggtatt 1080 gcagtaggaa cgactattgt agatgcagac aaatacgcag ttacagttga gactcgcttg 1140 atcgatgaga gagcagctca cgtaaatgca caattccgct tc 1182

<210> SEQ ID NO 141
<211> LENGTH: 1182
<212> TYPE: DNA
<213> ORGANISM: Chlamydia trachomatis

<400> SEQUENCE: 141
atgaaaaaac tcttgaaatc ggtattagtg tttgccgctt tgagttctgc ttcctccttg 60
caagctctgc ctgtggggaa tcctgctgaa ccaagcctta tgatcgacgg aattctatgg 120
gaaggtttcg gtggagatcc ttgcgatcct tgcaccactt ggtgtgacgc tatcagcatg 180
cgtatgggtt actatggaga ctttgttttc gaccgtgttt tgcaaacaga tgtgaataaa 240
gaattccaca tgggtgacaa gcctacaggt gatacaggca atagtacagc tccaaccact 300
tgtacagcaa gagagaatcc tgcttacggc cgacatatgc aggatgctga gatgtttaca 360
aatgctgctt acatggcatt gaatatttgg gatcgttttg atgtattctg tacattagga 420
gccaccagtg gatatcttaa aggaaattca gcatctttca acttagttgg cttgtttggg 480
gataatgaaa atcatggcac ggttgtcgaa acgaatcctg taccaaatat gagctttgat 540
caatctgttg ttgaacttta cacagatact accttctctt ggagtgctgg agctcgtgca 600
gctttgtggg agtgcggatg cgcgacttta ggcgcttcat tccaatacgc tcaatccaag 660
cctaaagtcg aagaattaaa cgttctctgt aacgcagctg agtttactat caataagcct 720
aaaggatatg tagggcaaga attccctctt gcactcaaat caggaactga tggagtgacg 780
ggcactaaag atgcctctat tgattaccat gagtggcaag caagtttagc tctctcttac 840
agactgaata tgttcactcc ctacattgga gttaaatggt ctcgagcaag ttttgatgcg 900
gatacgattc gtatagccca gccaaaatta gctacagctg tttttgatac taccacgctt 960
aacccaacta ttgctggagc tggcgaggtg aaagctgaca cagagggtca gctcggagat 1020
accatgcaaa tcgtttcctt gcaattgaac aagatgaaat ctagaaaatc ttgcggtatt 1080
gcagtaggaa cgactattgt agatgcagac aaatacgcag ttacagttga gactcgcttg 1140
atcgatgaga gagcagctca cgtaaatgca caattccgct tc 1182

<210> SEQ ID NO 142
<211> LENGTH: 1185
<212> TYPE: DNA

<213> ORGANISM: Chlamydia trachomatis

<400> SEQUENCE: 142

```
atgaaaaaac tc

```
agactcaata tgttcactcc ctacattgga gttaaatggt ctcgtgcaag ttttgattct      900
aatacaattc gtatagccca gccaagattg gtaacacctg ttgtagatac tacaacccctt     960 aacccaacta ttgcaggatg cggcagggta gtcgcagctg actcggaagg acagatatct    1020
gataccatgc aaatcgtttc cttgcaatta aacaagatga atctagaaaa atcttgcggt    1080
attgcagtag gaacgactat tgtagatgca gacaaatacg cagttacagt tgagactcgc    1140
ttgatcgatg agagagcagc tcacgtaaat gcacaattcc gcttc                    1185
```

<210> SEQ ID NO 144
<211> LENGTH: 1191
<212> TYPE: DNA
<213> ORGANISM: Chlamydia trachomatis

<400> SEQUENCE: 144

```
atgaaaaaac tcttgaaatc ggtattagtg tttgccgctt tgagttctgc ttcctccttg       60
caagctctgc ctgtggggaa tcctgctgaa ccaagcctta tgatcgacgg aattctatgg     120
gaaggttttg gtggagatcc ttgcgatcct tgcaccactt ggtgtgacgc tatcagcatg     180
cgtgttggtt actacggaga ctttgttttc gaccgtgttt tgcaaactga tgtgaataaa     240
gagtttgaga tgggagaggc tttagctggc agcgatgtag ctgggttaca aactatact      300 acaataaacg ttgatcgtcc aaaccccgca tatggcaagc acatgcaaga cgcagaaatg     360
tttacgaacg ctgcttacat gacattaaat atctgggatc gttttgatgt attctgtaca     420
ttgggagcaa ccactggtta tttaagagga aattcagcat ccttcaactt agttggattg     480
tttggcacaa aaacacaatc ttctagcttt aatgcaacga acgtattcc taacgctgct      540 ttgaatgagg ctgtggtgga actttacata aacactacct tctcttggag tgcaggtgct     600
cgtgcagctc tctgggagtg cgggtgcgcg acgttaggcg cttcattcca atacgctcaa     660
tccaagccta aaatcgaaga gttaaatgtt ctttgtaacg catccgaatt tactatcaat     720
aagccgaaag gatatgttgg ggcagaattt ccacttacaa tcaactcagg aactgaagga     780
gtgacgggga ctaaagatgc ctctattgac taccatgagt ggcaagcaag tttatctctt     840
tcttacagac taaatatgtt cactccctac attggagtta aatggtctag tgtaagtttt     900
gattccaata caatccgtat cgcccagcct agattggtta cagcagttgt ggataccact     960 accccttaacc cgactatcgc aggtaaagga agggtagtct ctgccgaaac cgataacgaa   1020
atgtctgata ccatgcaaat cgtttccttg cagttaaaca agatgaaatc tagaaaatct    1080
tgcggtattg cagtaggaac gactattgta gatgcagaca aatacgcagt tacagttgag    1140
gctcgcttga tcgatgagag agcagctcac gtaaatgcac aattccggtt c             1191
```

<210> SEQ ID NO 145
<211> LENGTH: 1188
<212> TYPE: DNA
<213> ORGANISM: Chlamydia trachomatis

<400> SEQUENCE: 145

```
atgaaaaaac tcttgaaatc ggtattagtg tttgccgctt tgagttctgc ttcctccttg       60
caagctctgc ctgtggggaa tcctgctgaa ccaagcctta tgatcgacgg aattctatgg     120
gaaggttttg gtggagatcc ttgcgatcct tgcaccactt ggtgtgacgc tatcagcatg     180
cgtgttggtt actacggaga ctttgttttc gaccgtgttt tgcaaactga tgtgaataaa     240
gagtttgaga tgggagaggc tttagctggc agagatgtag ctgggttaca aagtatact      300 gtagtaaacg ttgatcgccc aaaccccgca tatggcaagc acatgcaaga cgcagaaatg     360
```

```
tttacgaacg ctgcttacat gacattaaat atctgggatc gttttgatgt attttgtaca      420
ttgggagcaa ccactggtta tttaagagga aattccgcat ccttcaactt agttggattg      480
tttggcacaa aaacacaatc ttctggcttt gatgcaacga atagtattcc taacgctgct      540
ttgaatgagg ctgtggtgga actttacata aacactacct tctcttggag tgcaggtgct      600
cgtgcagctc tctgggagtg cgggtgcgcg acgttaggcg cttcattcca atacgctcaa      660
tccaagccta aaatcgaaga gttgaatgtt ctttgtaacg catccgaatt tactatcaat      720
aagccgaaag gatatgttgg ggcagaattt ccacttacaa tcaactcagg aactgaagga      780
gtgacgggga ctaaagatgc ctctattgac taccatgagt ggcaagcaag tttatccctt      840
tcttacagac taaatatgtt cactccctac attggagtta aatggtctag tgtaagtttt      900
gattccaata caatccgtat cgcccagcct agattggtta caccagttgt ggataccact      960
accctaaacc cgaccatcgc aggtaaagga accgtagtct cctcaaccga aaacgaaatg     1020
tctgatacca tgcaaatcgt ttccttgcag ttaaacaaga tgaaatctag aaaatcttgc     1080
ggtattgcag taggaacgac tattgtagat gcagataaat acgcagttac agttgaggct     1140
cgcttgatcg atgagagagc agctcacgta aatgcacaat tccggttc                  1188

<210> SEQ ID NO 146
<211> LENGTH: 1190
<212> TYPE: DNA
<213> ORGANISM: Chlamydia trachomatis

<400> SEQUENCE: 146
atgaaaaaac tcttgaaatc ggtattagtg tttgccgctt tgagttctgc ttcctccttg       60
caagctctgc ctgtggggaa tcctgctgaa ccaagcctta tgatcgacgg aattctatgg      120
gaaggttttg gtggagatcc ttgcgatcct tgcgccactt ggtgtgacgc tatcagcatg      180
cgtgttggtt actacggaga ctttgttttc gaccgtgttt tgcaaactga tgtgaataaa      240
gagtttgaga tgggagaggc tttagctggc aacgatgtag ctgagttaca aaactatact      300
aaagtaaacg ttgatcgtcc aaaccccgca tatggcaagc acatgcaaga cgcagaaatg      360
tttacgaacg ctgcttacat gacattaaat atctgggatc gttttgatgt attttgtaca      420
ttgggagcaa ccactggtta tttaagagga aattccgcat ccttcaactt agttggattg      480
tttggcacaa aaacaaatct tctgatttta atgcaacgaa tcgtattcct aacgctgctt      540
tgaatggggc tgtggtggaa ctttacataa acactacctt ctcttggagt gcaggtgctc      600
gtgcagctct ctgggagtgc gggtgcgcga cgttaggcgc ttcattccaa tacgctcaat      660
ccaagcctaa aatcgaagag ttgaatgttc tttgtaacgc atccgaattt actatcaata      720
agccgaaagg atatgttggg gcagaatttc cacttacaat caactcagga actgaaggag      780
tgacggggac taaagatgcc tctattgact accatgagtg gcaagcaagt ttatcccttt      840
cttacagact aaatatgttc actccctaca ttggagttaa atggtctagt gtaagttttg      900
attccaatac aatccgtatc gcccagccta gattggttac agcagttgtg gataccacta      960
ccctaaaccc gaccatcgca ggtaaaggaa ccgtagtcgc ttccgcaagc gataacgaca     1020
tgtctgatac catgcaaatc gtttccttgc agttaaacaa gatgaaatct agaaaatctt     1080
gcggtattgc agtaggaacg actattgtag atgcagataa atacgcagtt acagttgagg     1140
ctcgcttgat cgatgagaga gcagctcacg taaatgcaca attccggttc                1190

<210> SEQ ID NO 147
<211> LENGTH: 1188
<212> TYPE: DNA
```

<213> ORGANISM: Chlamydia trachomatis

<400> SEQUENCE: 147

```
atgaaaaaac tc

| | |
|---|---|
| cttacagact aaatatgttc actccctaca ttggagttaa atggtctagt gtaagttttg | 900 |
| attccaatac aatccgtatc gcccagccta gattggttaa agcagttgtg gataccacta | 960 |
| ccctaaaccc gaccatcgca ggtaaaggaa ccgtagtcgc ttccgcaagc gataacgaca | 1020 |
| tgtctgatac catgcaaatc gtttccttgc agttaaacaa gatgaaatct agaaaatctt | 1080 |
| gcggtattgc agtaggaacg actattgtag atgcagataa atacgcagtt acagttgagg | 1140 |
| ctcgtttgat cgatgagaga gcagctcacg taaatgcaca attccggttc | 1190 |

<210> SEQ ID NO 149
<211> LENGTH: 1191
<212> TYPE: DNA
<213> ORGANISM: Chlamydia trachomatis

<400> SEQUENCE: 149

| | |
|---|---|
| atgaaaaaac tcttgaaatc ggtattagtg tttgccgctt tgagttctgc ttcctccttg | 60 |
| caagctctgc ctgtggggaa tcctgctgaa ccaagcctta tgatcgacgg aattctatgg | 120 |
| gaaggttttg gtggagatcc ttgcgatcct tgcgccactt ggtgtgacgc tatcagcatg | 180 |
| cgtgttggtt actacggaga cttttgttttc gaccgtgttt tgcaaactga tgtgaataaa | 240 |
| gagtttgaga tgggagaggc tttagctggc agcgatgtag ctgagttaca aaactatact | 300 |
| aaagtaaacg ttgatcgtcc aaaccccgca tatggcaagc acatgcaaga cgcagaaatg | 360 |
| tttacgaacg ctgcttacat gacattaaat atctgggatc gttttgatgt attttgtaca | 420 |
| ttgggagcaa ccactggtta tttaaggaga aattccgcat ccttcaactt agttggattg | 480 |
| tttggcacaa aaacacaagc ttctagcttt aatgcaacga atcgttttcc taacgctgct | 540 |
| ttgaatgggg ctgtggtgga actttacata aacactacct tctcttggag tgcaggtgct | 600 |
| cgtgcagctc tctgggagtg cgggtgcgcg acgttaggcg cttcattcca atacgctcaa | 660 |
| tccaagccta aaatcgaaga gttgaatgtt ctttgtaacg catccgaatt tactatcaat | 720 |
| aagccgaaag gatatgttgg ggcagaattt ccacttacaa tcatctcagg aactgaagga | 780 |
| gtgacgggga ctaaagatgc ctctattgac taccatgagt ggcaagcaag tttatccctt | 840 |
| tcttacagac taaatatgtt cactccctac attggagtta atggtctag tgtaagtttt | 900 |
| gattccaata caatccgtat cgcccagcct agattggtta cagcagttgt ggataccact | 960 |
| accctaaacc cgaccatcgc aggtaaagga accgtagtcg cttccgcaag cgaaaacgac | 1020 |
| atgtctgata ccatgcaaat cgtttccttg cagttaaaca agatgaaatc tagaaaatct | 1080 |
| tgcggtattg cagtaggaac gactattgta gatgcagata aatacgcagt tacagttgag | 1140 |
| gctcgtttga tcgatgagag agcagctcac gtaaatgcac aattccggtt c | 1191 |

<210> SEQ ID NO 150
<211> LENGTH: 1191
<212> TYPE: DNA
<213> ORGANISM: Chlamydia trachomatis

<400> SEQUENCE: 150

| | |
|---|---|
| atgaaaaaac tcttgaaatc ggtattagtg tttgccgctt tgagttctgc ttcctccttg | 60 |
| caagctctgc ctgtggggaa tcctgctgaa ccaagcctta tgatcgacgg aattctatgg | 120 |
| gaaggttttg gtggagatcc ttgcgatcct tgcgccactt ggtgtgacgc tatcagcatg | 180 |
| cgtgttggtt actacggaga cttttgttttc gaccgtgttt tgcaaactga tgtgaataaa | 240 |
| gagtttgaga tgggagaggc tttagctgtc agcgatgtag ctgagttaca aaactatact | 300 |
| aaagtaaacg ttgatcgtcc aaaccccgca tatggcaagc acatgcaaga cgcagaaatg | 360 |

```
tttacgaacg ctgcttacat gacattaaat atctgggatc gttttgatgt attttgtaca      420
ttgggagcaa ccactggtta tttaagagga aattccgcat ccttcaactt agttggattg      480
tttggcacaa aaacacaatc ttctagcttt aatgcaacga atcgtattcc taacgctgct      540
ttgaatgggg ctgtagtgga actttacata aacactacct tctcttggag tgcaggtgct      600
cgtgcagctc tctgggagtg cgggtgcgcg acgttaggcg cttcattcca atacgctcaa      660
tccaagccta aaatcgaaga gttgaatgtt ctttgtaacg catccgaatt tactatcaat      720
aagccgaaag gatatgttgg ggcagaattt ccacttacaa tcatctcagg aactgaagga      780
gtgacgggga ctaaagatgc ctctattgac taccatgagt ggcaagcaag tttatccctt      840
tcttacagac taaatatgtt cactccctac attggagtta aatggtctag tgtaagtttt      900
gattccaata caatccgtat cgcccagcct agattggtta cagcagttgt ggataccact      960 acccctaaacc cgaccatcgc aggtaaagga accgtagtcg cttccgcaag cgaaaacgaa     1020
atgtctgata ccatgcaaat cgtttccttg cagttaaaca agatgaaatc tagaaaatct     1080
tgcggtattg cagtaggaac ggctattgta gatgcagata aatacgcagt tacagttgag     1140
gctcgtttga tcgatgagag agcagctcac gtaaatgcac aattccggtt c             1191
```

<210> SEQ ID NO 151
<211> LENGTH: 1190
<212> TYPE: DNA
<213> ORGANISM: Chlamydia trachomatis

<400> SEQUENCE: 151

```
atgaaaaaac tcttgaaatc ggtattagtg tttgccgctt tgagttctgc ttcctccttg       60
caagctctgc ctgtggggaa tcctgctgaa ccaagcctta tgatcgacgg aattctatgg      120
gaaggttttg gtggagatcc ttgcgatcct tgcgccactt ggtgtgacgc tatcagcatg      180
cgcgttggtt actacggaga ctttgttttc gaccgtgttt tgcaaactga tgtgaataaa      240
gagtttgaga tgggagaggc tttagctgtc agcgatgtag atgagttaca aaactatact      300
aaagtaaacg ttgatcgtcc aaaccccgca tatgcaagc acatgcaaga cgcagaaatg      360
tttacgaacg ctgcttacat gacattaaat atctgggatc gttttgatgt attttgtaca      420
ttgggagcaa ccactggtta tttaagagga aattccgcat ccttcaactt agttggattg      480
tttggcacaa aaacacaatt tctaagttta atgcaacgaa tcgtattcct aacgctgctt      540
tgaatggggc tgtggtggaa ctttacataa acaccacctt ctcttggagt gcaggtgctc      600
gtgcagctct ctgggagtgc gggtgcgcga cgttaggcgc ttcattccaa tacgctcaat      660
ccaagcctaa aatcgaagag ttgaatgttc tttgtaacgc atccgaattt actatcaata      720
agccgaaagg atatgttggg gtagaatttc cacttacaat catctcagga actgaaggag      780
tgacggggac taaagatgcc tctattgact accatgagtg gcaagcaagt ttatccttt     840 cttacagact aaatatgttc actccctaca ttggagttaa atggtctagt gtaagttttg      900
attccaatac aatccgtatc gcccagccta gattggttac agcagttgtg gataccacta      960
ccctaaaccc gaccatcgca ggtaaaggaa ccgtagtctc ttccgcaagc gataacgaaa     1020
tgtctgatac catgcaaatc gtttccttgc agttaaacaa gctgaaatct agaaaatctt     1080
gcggtattgc agtaggaacg gctattgtag atgcagataa atacgcagtt acagttgagg     1140
ctcgtttgat cgatgagaga gcagctcacg taaatgcaca attccggttc              1190
```

<210> SEQ ID NO 152
<211> LENGTH: 1191
<212> TYPE: DNA

<213> ORGANISM: Chlamydia trachomatis

<400> SEQUENCE: 152

| | | | | | |
|---|---|---|---|---|---|
| atgaaaaaac

METHODS FOR IDENTIFYING AN EPITOPE OF A POLYPEPTIDE, CHLAMYDIAL ANTIGENIC POLYPEPTIDES IDENTIFIED THEREBY, AND METHODS OF USE THEREOF

CROSS-REFERENCE

This application claims the benefit of U.S. Provisional Patent Application No. 60/713,192, filed Aug. 30, 2005, which application is incorporated herein by reference in its entirety.

STATEMENT REGARDING FEDERALLY SPONSORED RESEARCH

The U.S. government has certain rights in this invention, pursuant to grant nos. AI39499 and EY/AI12219 awarded by the National Institutes of Health.

FIELD OF THE INVENTION

The present invention is in the field of epitope mapping of polypeptides.

BACKGROUND OF THE INVENTION

*Chlamydia trachomatis* is a human pathogen of worldwide importance. This obligate intracellular bacterium is responsible for ocular, respiratory, and sexually transmitted diseases, many of which result in significant sequelae including blindness, small airways disease, infertility and ectopic pregnancy. The host immune response to chlamydial infection is characterized as both protective and pathogenic[1]. While protective immune responses likely occur at mucosal sites of bacterial invasion, the extent of this response and those that lead to clinical pathology in humans remain ill defined. This is in part due to the difficulty in studying human populations and our inadequate understanding of the host-pathogen immune interactions.

To date, the major outer membrane protein (MOMP) of *C. trachomatis* is the organism's most antigenically diverse protein. Its interactions with the host mucosal immune system are far encompassing and include the elicitation of T cell help for the production of antibodies[2,3] and neutralizing infection in vitro[4]. Reactivity to monoclonal antibodies (MAb) against MOMP B cell determinants form the basis for immunotyping chlamydial strains into serological variants, or serovars[5]. These serovars have been grouped into the following classes: B class (serovars B, Ba, D, Da, E, L1, L2, L2a); C class (serovars A, C, H, I, Ia, J, Ja, K, and L3); and Intermediate class (serovars F, G, and Ga). Through the cumulative efforts of a number of mapping studies, serovar-, serovar class-, subspecies-, and genus-specific epitopes and T cell determinants have been mapped to variable segments (VSs) and constant (C) regions of MOMP[2,3,5-28].

Over the last decade, analyses of the genetic diversity of the MOMP gene, ompA, have identified genotypes with surface antigens immunologically distinct from the parent serovar[29-33]. Consequently, serotyping of *C. trachomatis* has been limited by the MAbs available for such typing, evidenced by the fact that only through the development of additional MAbs were later serovars identified. Moreover, as new serotypes of the organism emerge, currently available MAbs may fail to identify them. The use of epitope mapping to identify determinants of newly identified ompA genotypes is not feasible because this technique is laborious, time consuming, and expensive since numerous recombinant fusion proteins[2,5,14,16,28] or overlapping synthetic peptides need to be generated and tested[3,6,7,11,13,15,24,25,27,34]. Employing this technique for more extensive studies of functional domains on MOMP, including additional B and T cell recognition sites and HLA restriction[12,17-19] would be important but also limited by the same factors.

There is a need in the art for methods for predicting structural and functional characteristics of a protein based on a nucleotide sequence encoding the protein and/or the amino acid sequence. The present invention addresses this need.

LITERATURE

Millman et al. (2001) *J. Bacteriol.* 183:5997-6008; Montigiani et al. (2002) *Infect. Immunity* 70:368-379; Millman et al. (2004) *J. Bacteriol.* 186:2457-2465.

SUMMARY OF THE INVENTION

The present invention provides a method of classifying an epitope displayed by a polypeptide; a method of determining the presence of an epitope on a polypeptide encoded by a test nucleotide sequence; and a method of generating a nucleotide sequence encoding a polypeptide that exhibits a selected epitope. The present invention provides antigenic polypeptides that display selected epitope(s); macromolecules comprising such polypeptides; and compositions (including immunogenic compositions) comprising the antigenic polypeptides or macromolecules. The present invention further provides methods of inducing an immune response to a *Chlamydia*. The present invention further provides arrays of nucleic acids, arrays of polypeptides, and arrays of antibodies, which arrays are useful in identification and/or classification of a *Chlamydia*.

BRIEF DESCRIPTION OF THE DRAWINGS

Figure 1A:
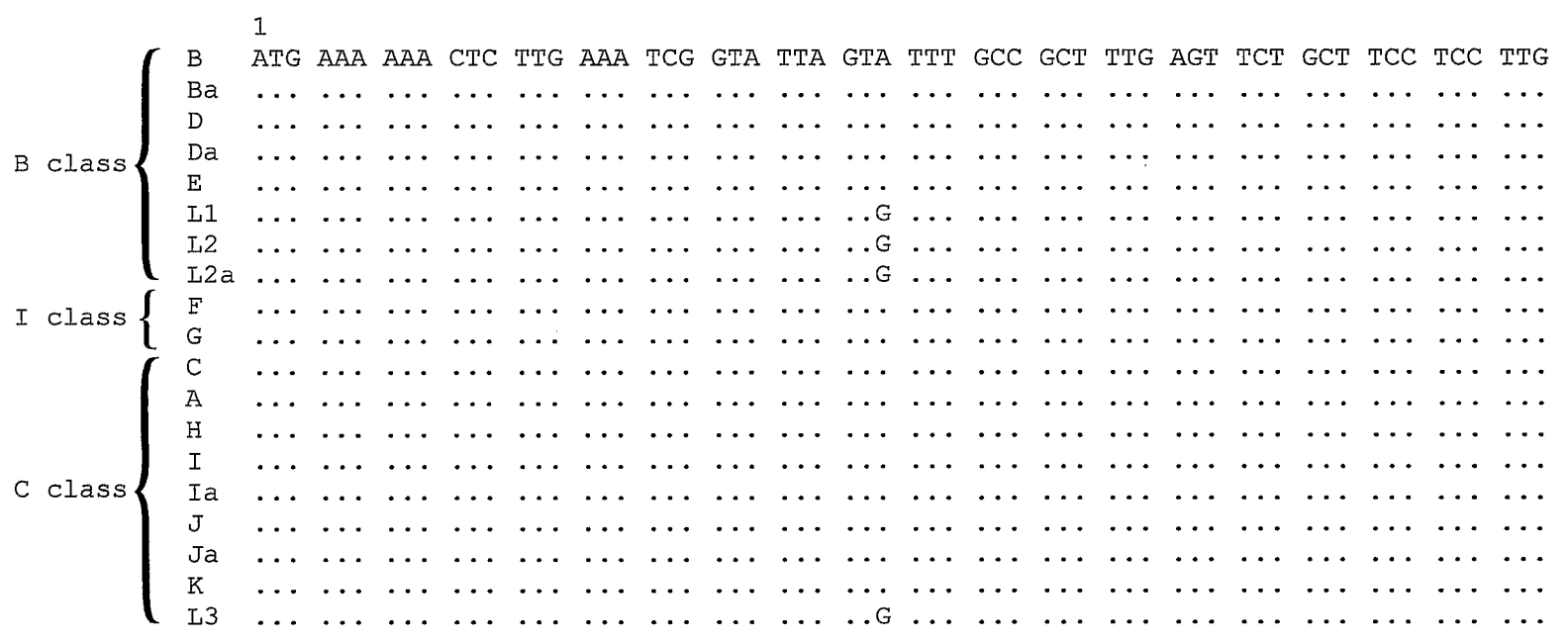
Figure 1B:
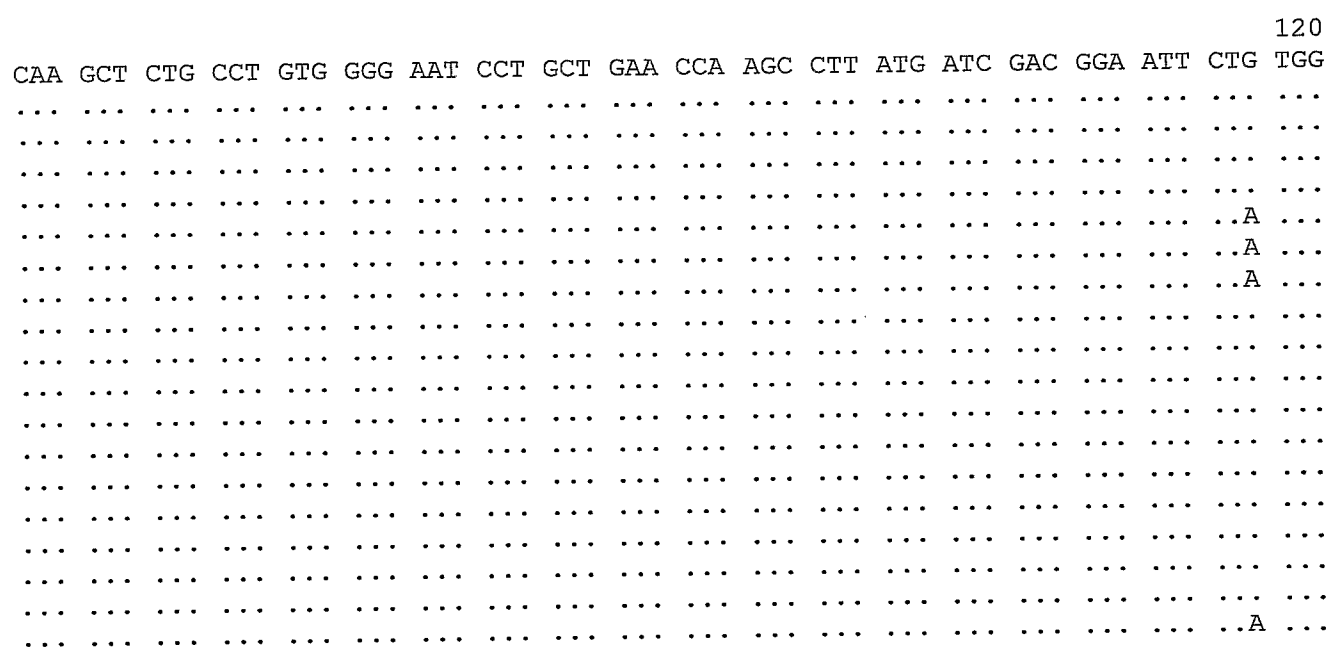
Figure 1C:
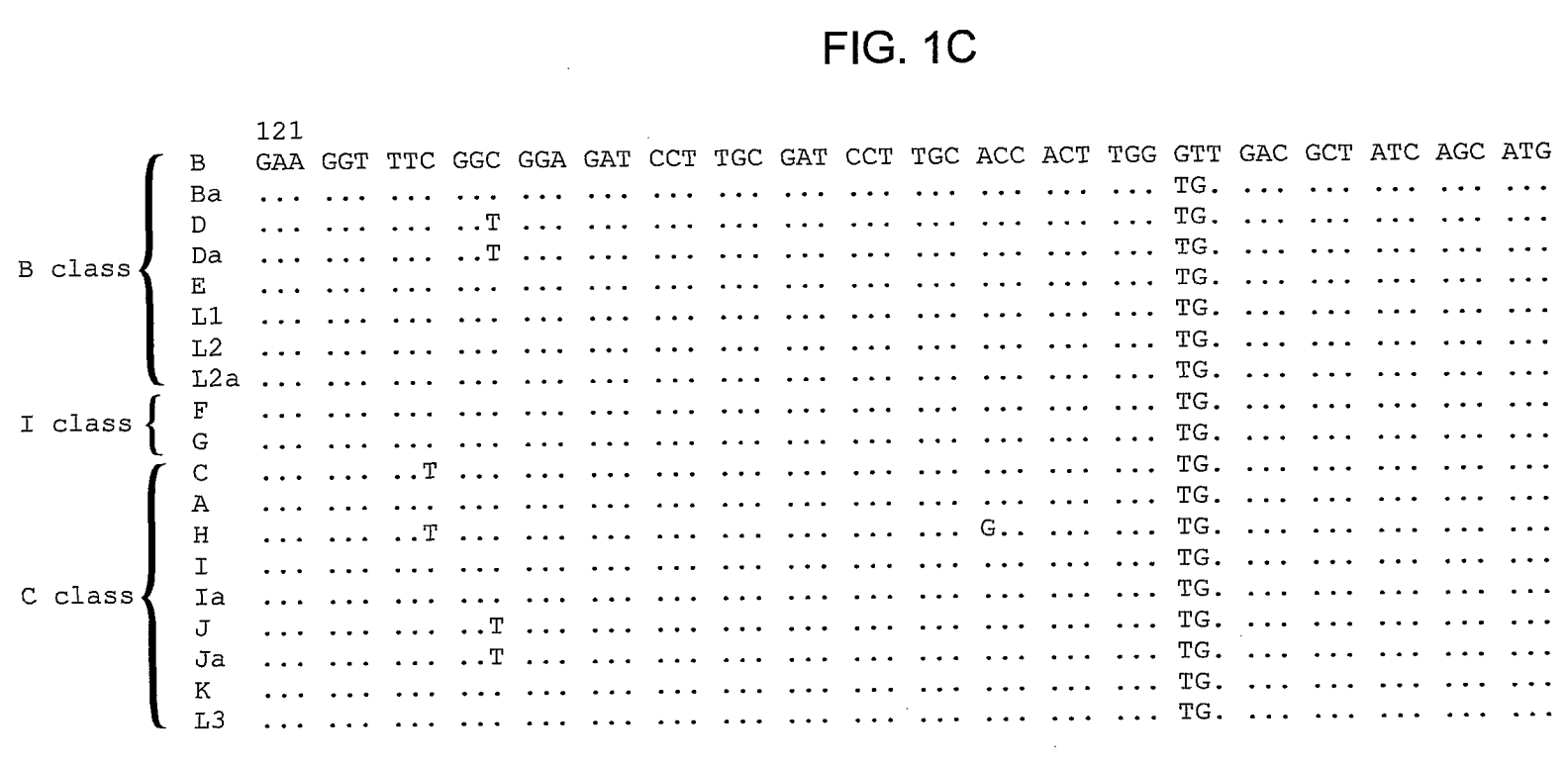
Figure 1D:
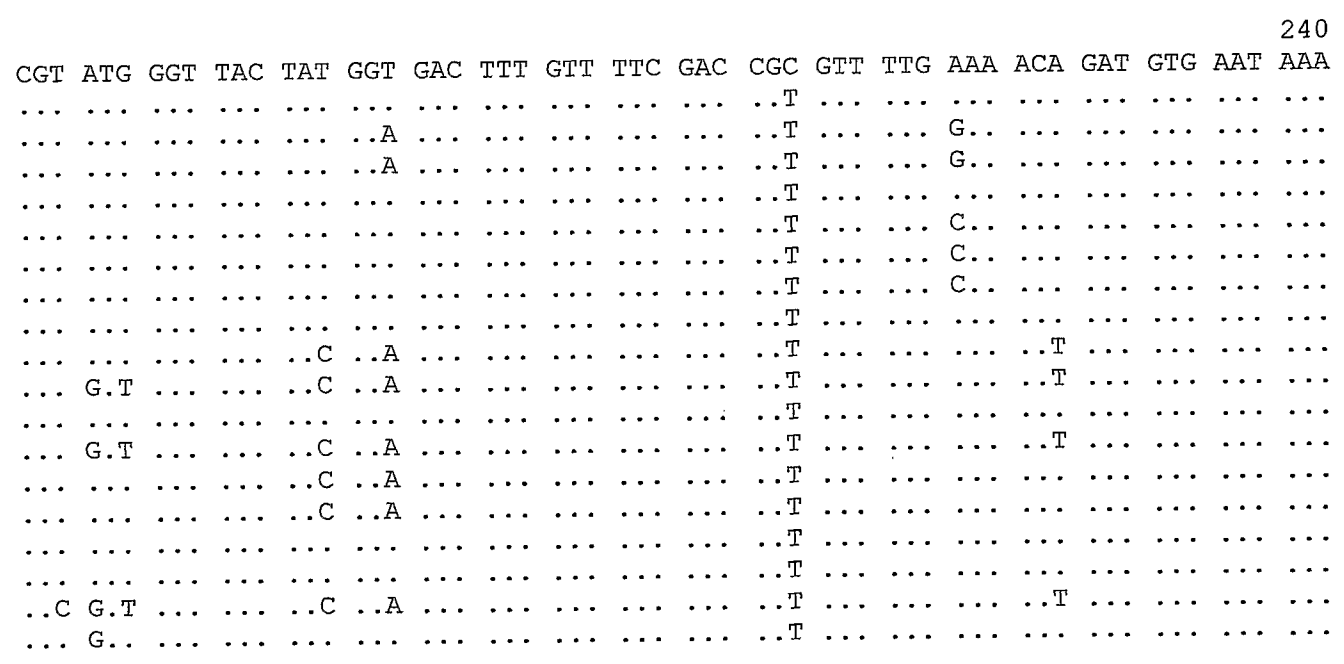
Figure 1E:
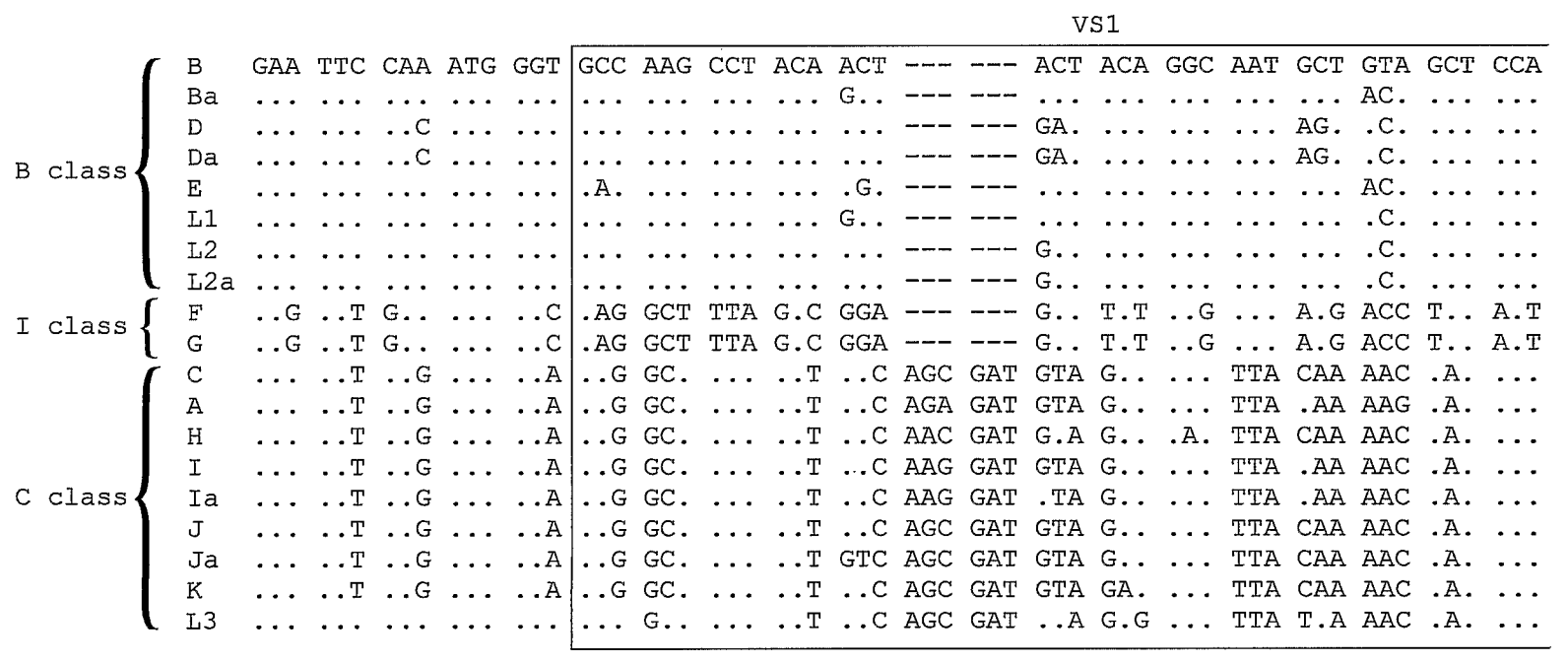
Figure 1F:
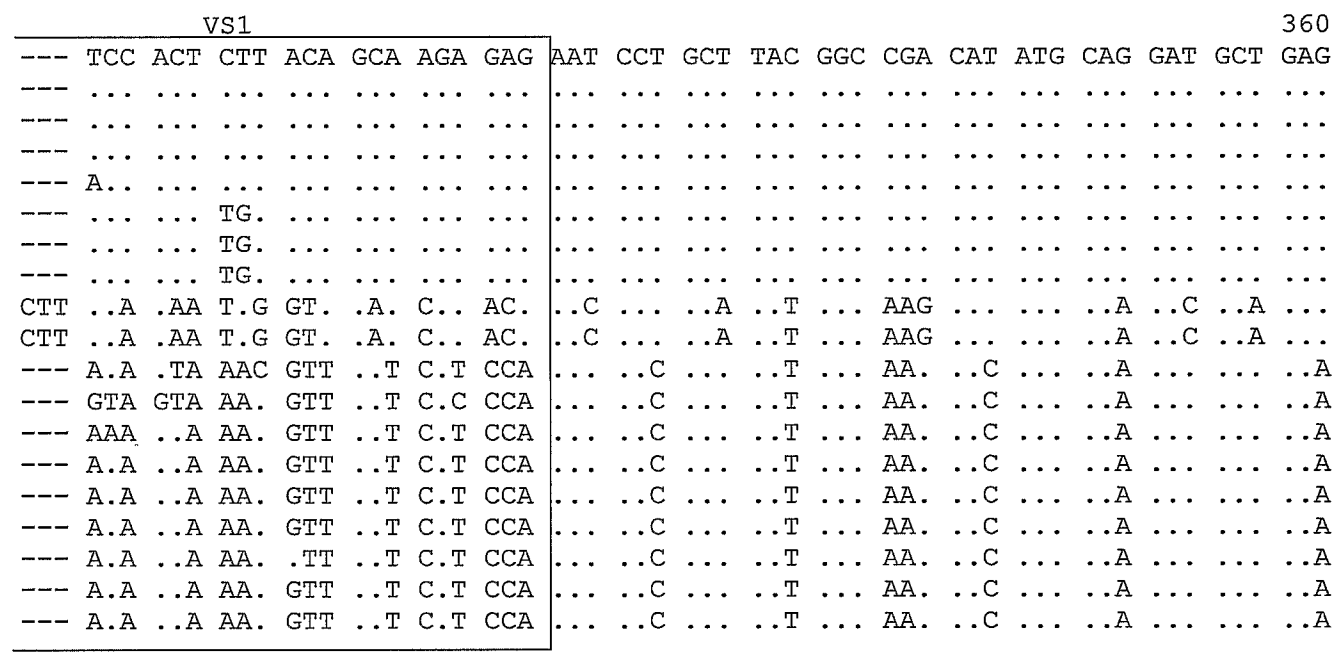
Figure 1G:
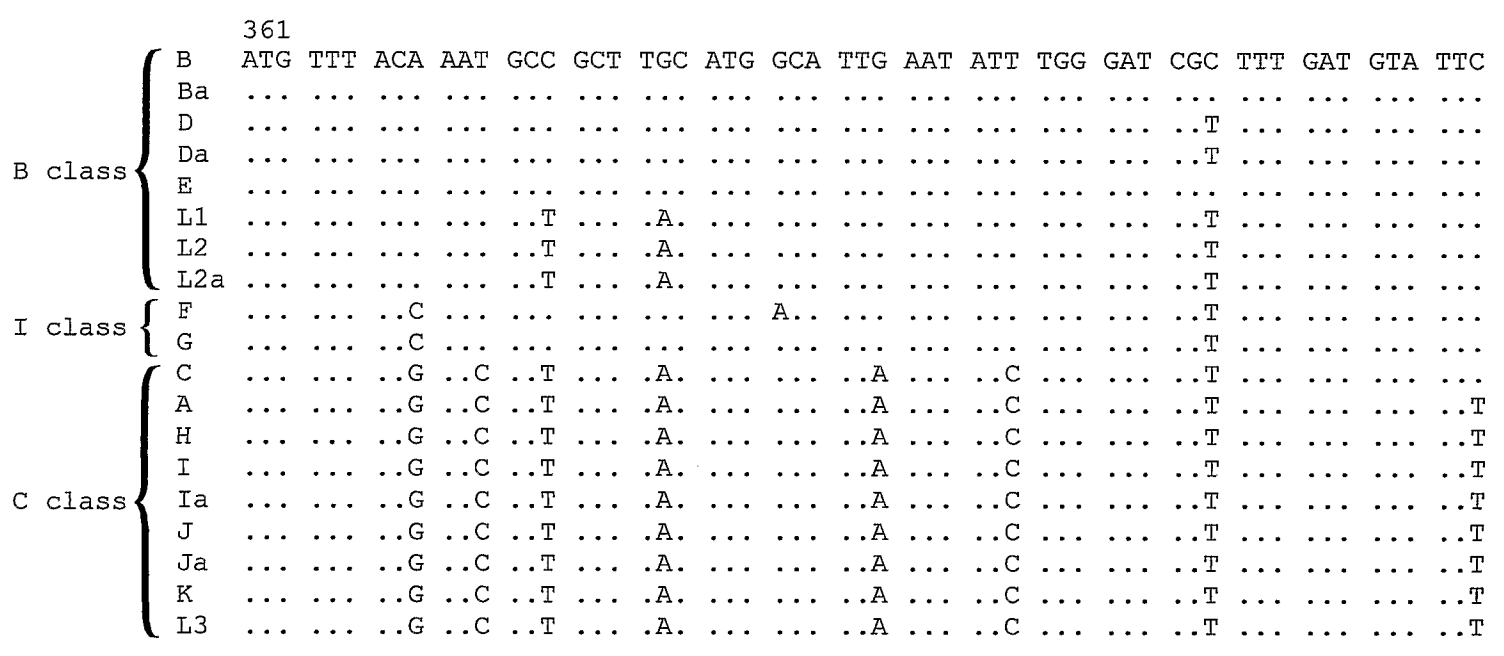
Figure 1J:
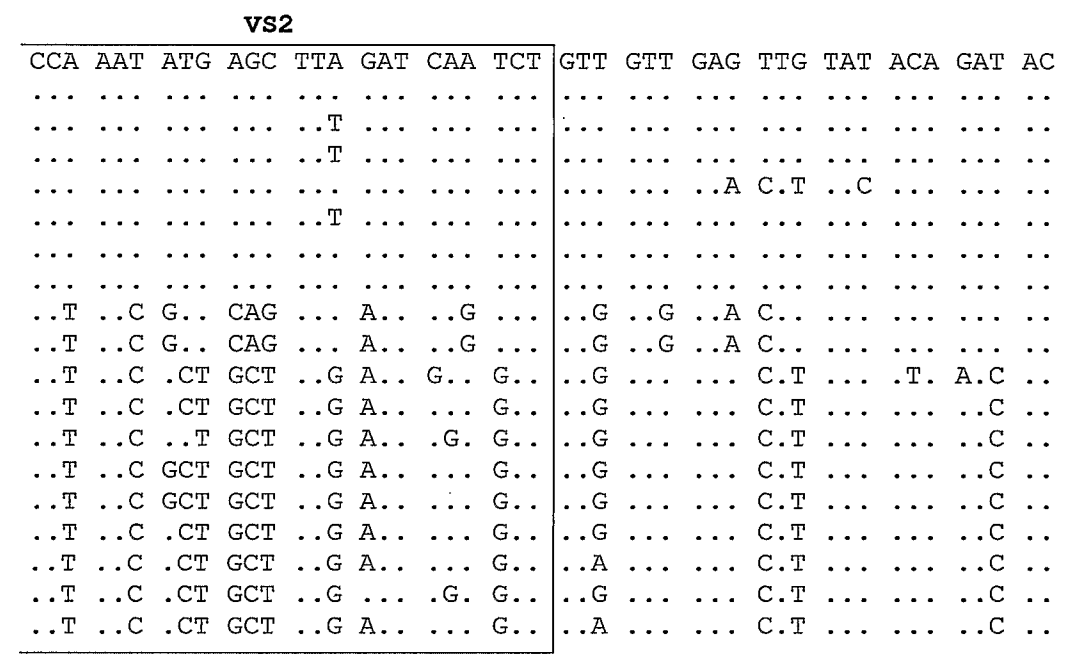
Figure 1K:
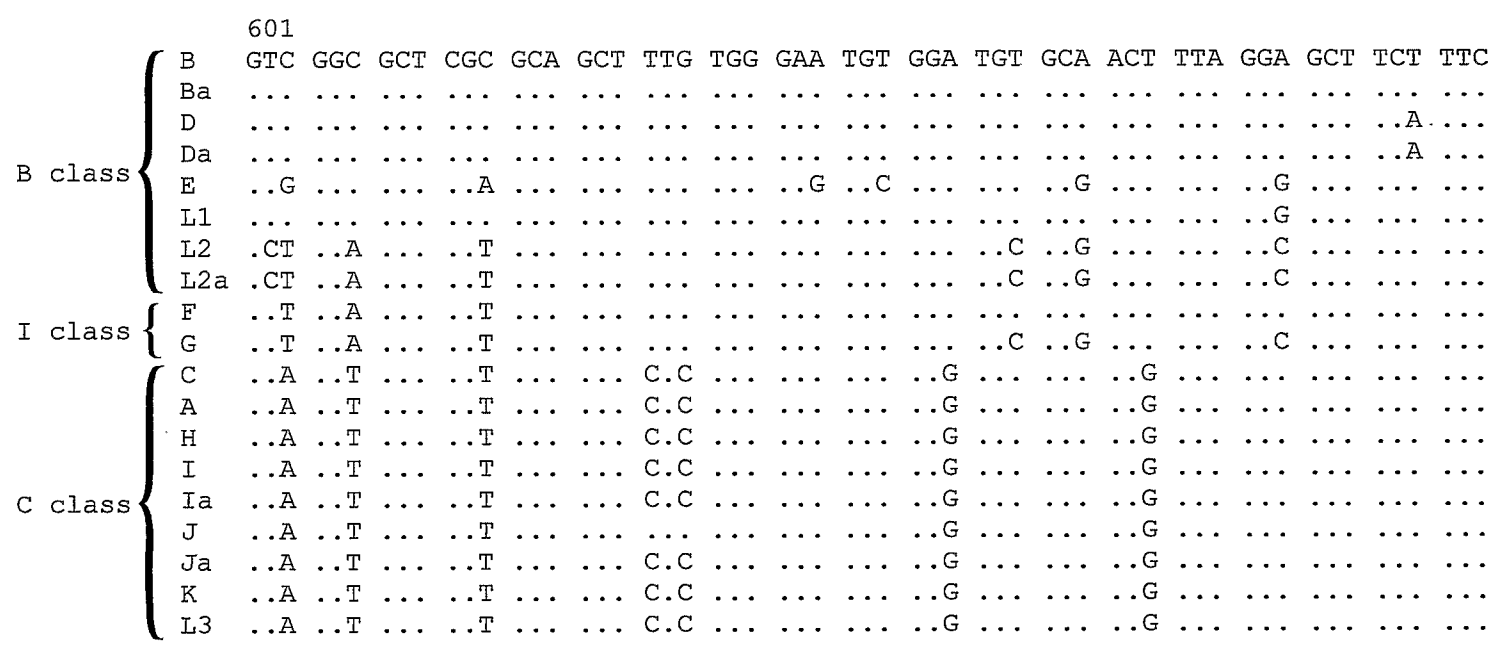
Figure 1L:
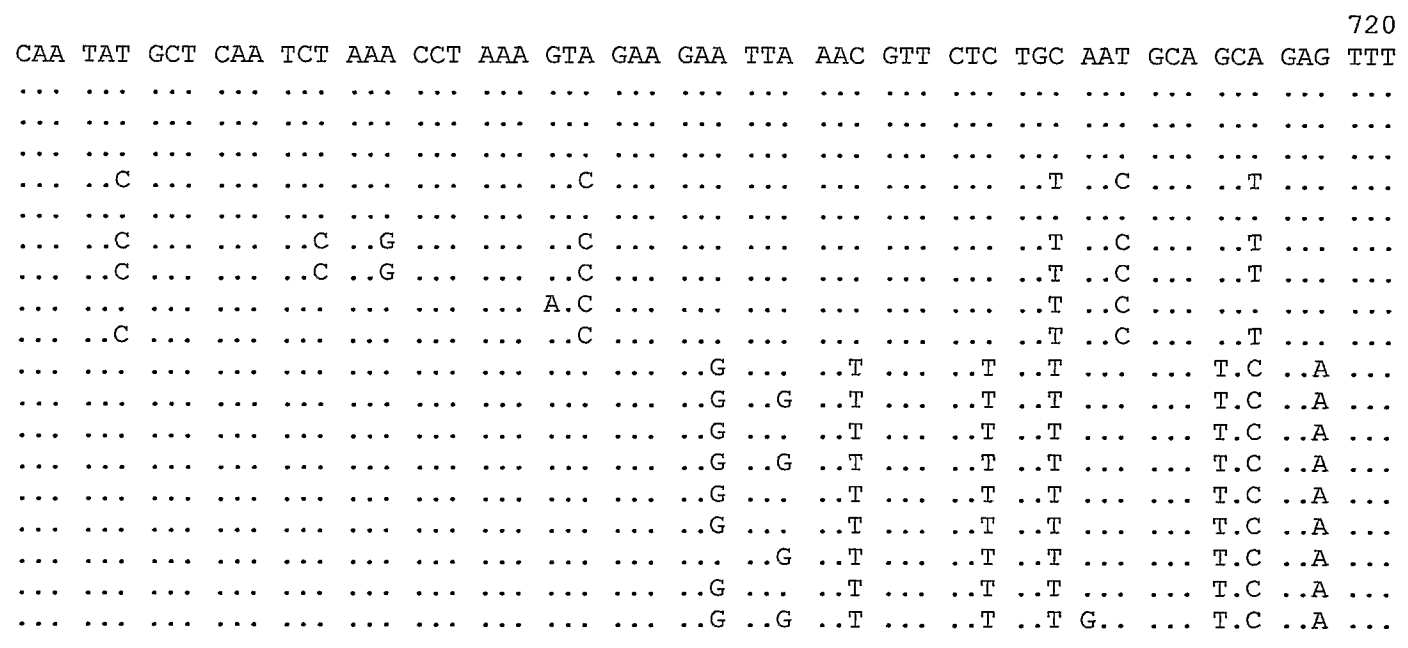
Figure 1N:
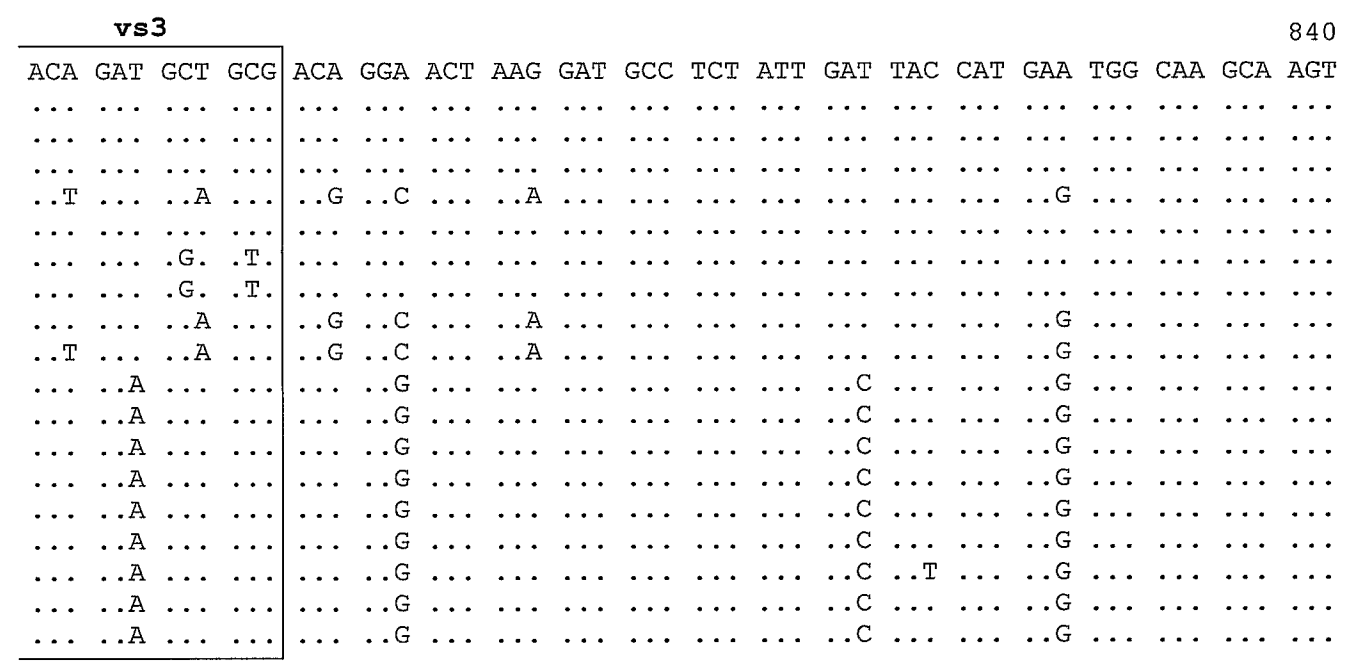
Figure 1P:
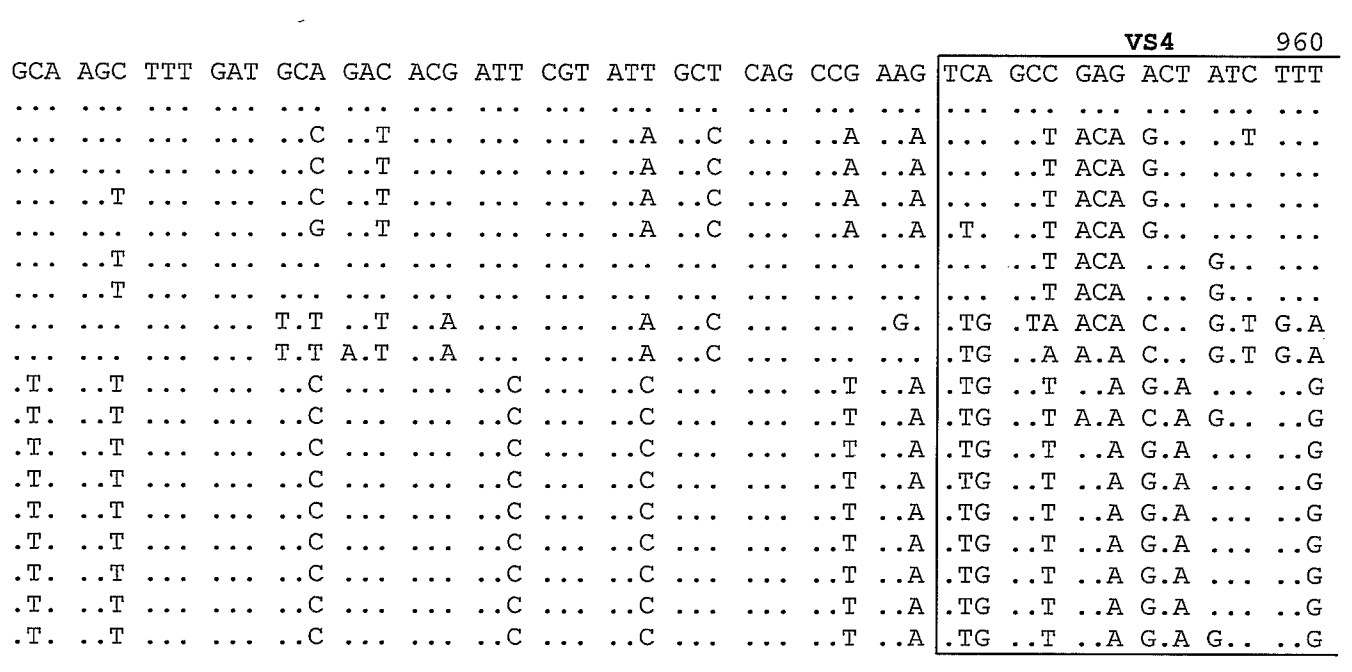
Figure 1Q:
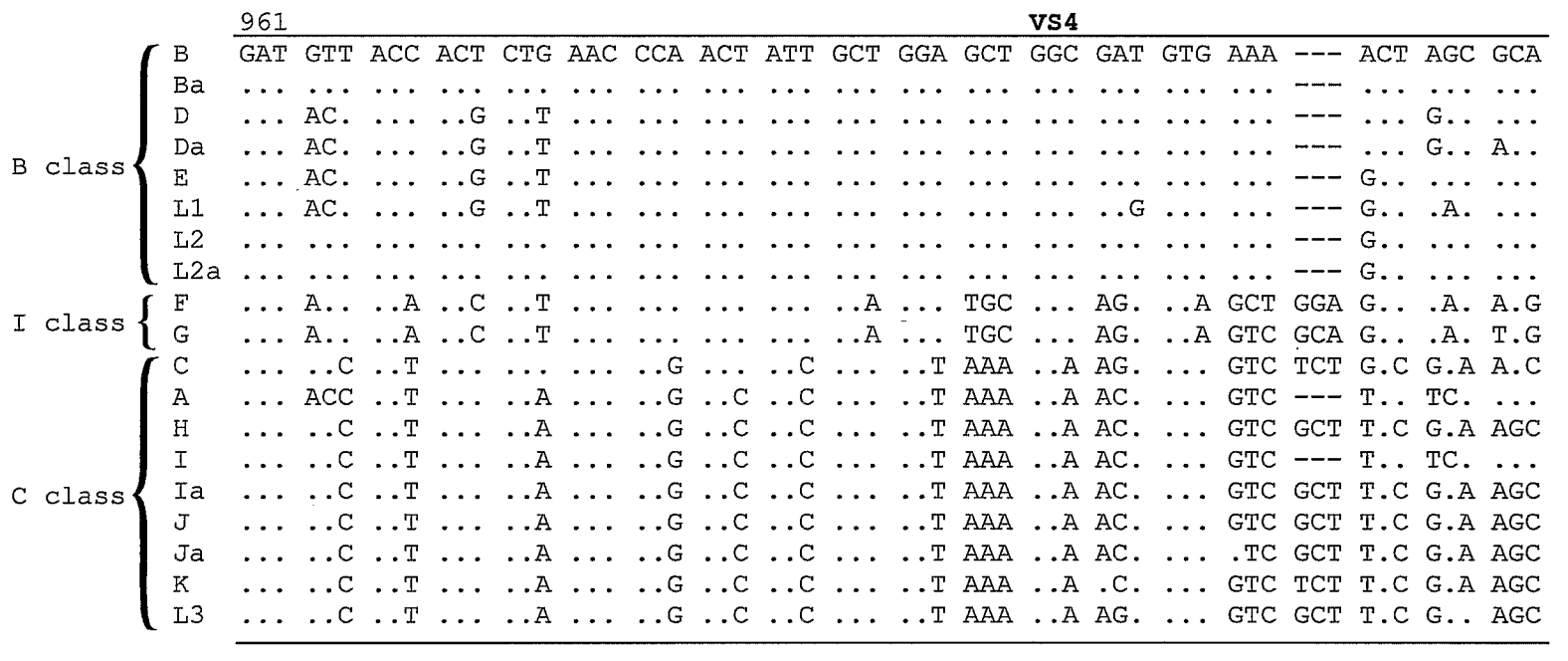
Figure 1R:
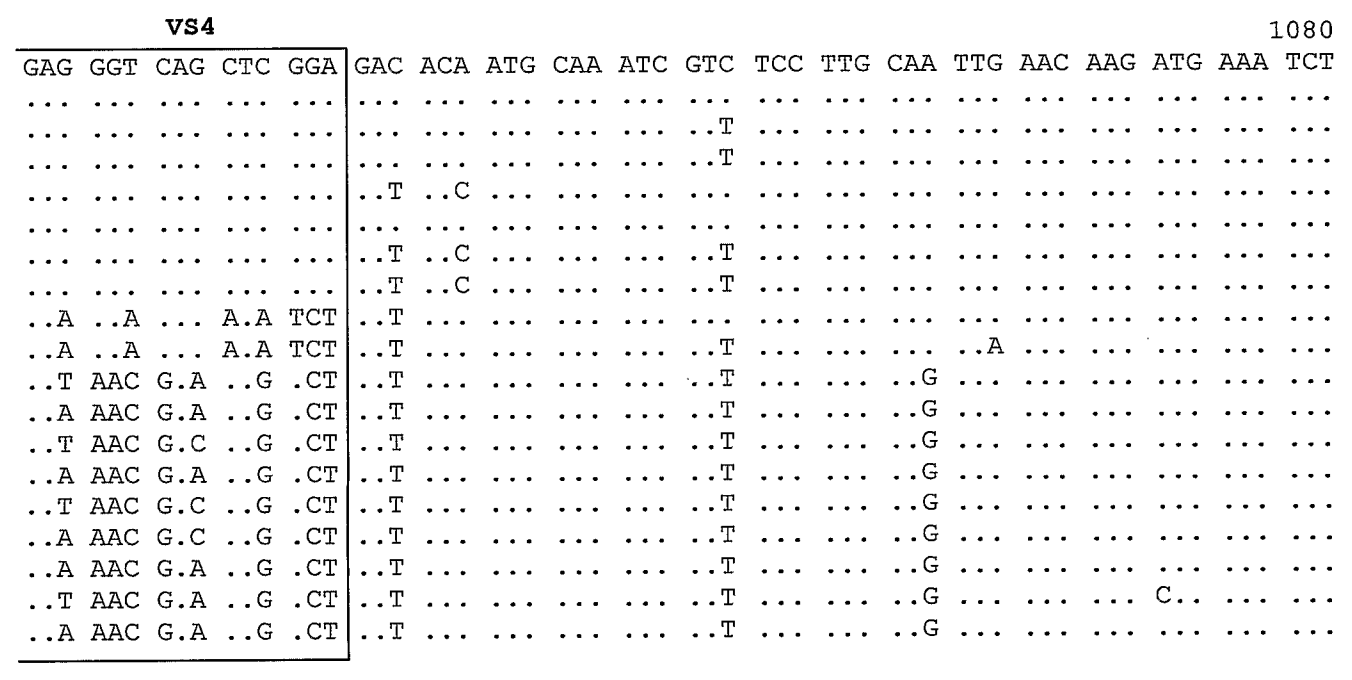

FIGS. 1A-1T depict an alignment of amino acid sequences of the major outer membrane protein of 19 *Chlamydia* serovars.

FIG. 2 depicts OmpA nucleotide positions that differentiate serovar class.

FIGS. 3A-D depict variation of positions that differentiate serovar class (A, all classes from one another; I, I class from C and B; C, C class from B and I; B, B class from I and C) with type of differentiation (FIG. 3A) ompA nucleotide region (FIG. 3B; constant regions C1, C2, C3, and C4, and variable regions V1, V2, V3, and V4), codon position (FIG. 3C), and type of change (FIG. 3D; B, both; G, gap, N, non-synonymous; S, synonymous).

FIG. 4 depicts ompA nucleotide positions that differentiate the I class serovars.

FIG. 5 depicts ompA nucleotide positions that differentiate the B class serovars.

FIGS. 6A and 6B depict ompA nucleotide positions that differentiate the C class serovars.

FIGS. 7A-D depict variation of positions that differentiate serovar by type of differentiation (FIG. 7A), ompA nucleotide region (FIG. 7B), codon position (FIG. 7C) and type of change (FIG. 7D).

FIG. 8 depicts a model that differentiates serotype class.

FIG. 9 depicts a model that differentiates serovars of the B class.

FIG. 10 depicts a model that differentiates serovars of the C class.

FIG. 11 depicts an exemplary test device.

DEFINITIONS

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, serine-threonine, phenylalanine-tyrosine, lysine-arginine, alanine-valine, aspartate-glutamate, and asparagine-glutamine.

The term "synonymous nucleotide substitution" refers to a nucleotide substitution in a codon that does not result in a change in encoded amino acid.

The term "non-synonymous nucleotide substitution" refers to a nucleotide substitution in a codon that results in a change in encoded amino acid.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art.

By "purified" is meant a compound of interest has been separated from components that accompany it in nature. "Purified" can also be used to refer to a compound of interest separated from components that can accompany it during manufacture (e.g., in chemical synthesis). Typically, a compound is substantially pure when it is at least 50% to 60%, by weight, free from organic molecules with which it is naturally associated or with which it is associated during manufacture. Generally, the preparation is at least 75%, more preferably at least 90%, and most preferably at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

The term "heterologous," as used herein in the context of a subject antigenic macromolecule, where a subject antigenic macromolecule comprises a subject antigenic polypeptide and a heterologous macromolecules, refers to a macromolecule that is other than a subject polypeptide, e.g., a macromolecule that is not normally associated with a subject antigenic polypeptide. Where the heterologous macromolecule is a polypeptide, the heterologous macromolecule typically bears no significant amino acid sequence identity to the antigenic polypeptide, e.g., the heterologous macromolecule typically has less than about 50%, less than about 40%, less than about 30%, or less than about 20% amino acid sequence identity to the antigenic polypeptide.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

The term "*Chlamydia*" includes a member of the family Chlamydiaceae and includes *C. trachomatis*, *C. pneumonia*, and *C. psittaci*, and other genera and species of the family.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples.

The term "protective immunity" means that a vaccine or immunization schedule that is administered to a mammal induces an immune response that prevents, retards the development of, or reduces the severity of a disease that is caused by a pathogen (e.g., *Chlamydia*), or diminishes or altogether eliminates the symptoms of the disease.

The term "antibody" encompasses polyclonal and monoclonal antibody preparations, as well as preparations including hybrid antibodies, altered antibodies, $F(ab')_2$ fragments, F(ab) molecules, Fv fragments, single chain fragment variable displayed on phage (scFv), single domain antibodies, chimeric antibodies, humanized antibodies, and functional fragments thereof which exhibit immunological binding properties of the parent antibody molecule.

As used herein, the term "monoclonal antibody" refers to an antibody composition having a homogeneous antibody population. The term is not limited by the manner in which it is made. The term encompasses whole immunoglobulin molecules, as well as Fab molecules, $F(ab')_2$ fragments, Fv fragments, single chain fragment variable displayed on phage (scFv), and other molecules that exhibit immunological binding properties of the parent monoclonal antibody molecule. Methods of making polyclonal and monoclonal antibodies are known in the art and described more fully below.

An "antigen" is defined herein to include any substance that may be specifically bound by an antibody molecule. An "immunogen" is an antigen that is capable of initiating lymphocyte activation resulting in an antigen-specific immune response.

By "epitope" is meant a site on an antigen to which specific B cells and/or T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments the polymer that are discontinuous in the linear sequence but are continuous in the folded conformation(s). Epitopes that are composed of single segments of biopolymers or other molecules are termed continuous or linear epitopes. T cell epitopes are generally restricted to linear peptides. Antibodies that recognize the same epitope can be identified in a simple immunoassay showing the ability of one antibody to block the binding of another antibody to a target antigen.

A "*Chlamydia* serovar class B epitope" is an epitope displayed by an antigenic polypeptide that, when administered to a mammalian host, elicits an immune response to a *Chlamydia* of serovar class B. Likewise, a "*Chlamydia* serovar class C epitope," and a "*Chlamydia* serovar class I epitope," refer to an epitope displayed by an antigenic polypeptide that, when administered to a mammalian host, elicits an immune response to a *Chlamydia* of serovar class C and class I, respectively.

The terms "individual," "host," "subject," and "patient," used interchangeably herein, refer to a mammal, e.g., a human.

The term "binds specifically," in the context of antibody binding, refers to high avidity and/or high affinity binding of an antibody to a specific polypeptide i.e., epitope of a polypeptide, e.g., a subject antigenic polypeptide. For example, antibody binding to an epitope on a specific subject antigenic polypeptide or fragment thereof is stronger than binding of the same antibody to any other epitope, particularly those which may be present in molecules in association with, or in the same sample, as the specific polypeptide of interest, e.g., binds more strongly to a specific subject antigenic polypeptide epitope than to any other polypeptide epitope so that by adjusting binding conditions the antibody binds almost exclusively to the specific subject antigenic polypeptide epitope and not to any other polypeptide epitope, or to any other polypeptide which does not comprise the epitope. Antibodies that bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a subject antigenic polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an antibody" includes a plurality of such antibodies and reference to "the B-cell epitope" includes reference to one or more B-cell epitopes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a method of classifying an epitope displayed by a polypeptide, using nucleotide sequence information and available immunological reactivity data. The method is useful for classifying epitopes displayed on polypeptides that are members of a polypeptide family comprising multiple variants. Epitopes are classified based on correlation of a nucleotide character state of a variable nucleotide based on a mathematical model (computer program) and with available immunological reactivity data.

Correlation of nucleotide character states with immunological reactivity data allows determination of the presence of an epitope on a polypeptide encoded by a test nucleotide sequence, and can be used to verify the model. Thus, the present invention further provides a method of determining the presence of an epitope on a polypeptide encoded by a test nucleotide sequence. The method generally involves comparing the test nucleotide sequence encoding a test polypeptide to a plurality of reference sets of correlated nucleotide character states, which correlated nucleotide character states correlate a nucleotide character state of a variable nucleotide with immunological reactivity data, when available; and determining the best fit of the test nucleotide sequence to a reference set from among the plurality of reference sets. An identity of at least 80% to a reference set associated with a selected epitope indicates that the test polypeptide exhibits the epitope. These methods are useful for predicting whether a polypeptide encoded by a test nucleic acid will exhibit selected epitopes.

Correlation of nucleotide character states with immunological reactivity data also allows the design of a nucleotide sequence encoding an antigenic peptide with specific antigenic characteristics. Thus, the present invention provides a method of generating a nucleotide sequence encoding a polypeptide that exhibits a selected epitope. Reference sets are generated, based on correlation of nucleotide character states from the model with immunological reactivity data; and, based on the reference sets, a nucleotide sequence is generated that encodes one or more selected epitopes. These methods are useful in the design of antigenic peptides displaying selected epitopes, which in turn are useful for inducing an immune response to the polypeptides displaying such epitopes, e.g., polypeptides that are displayed on the outer membranes of pathogenic bacteria.

Immunological reactivity data that are suitable for use include, but are not limited to, immunological reactivity with serovar and/or serovar class-specific antibody; immunological reactivity with strain-specific antibody; and the like.

The present invention further provides a computer program product that includes a computer program stored thereon for carrying out a subject method. The present invention further provides a computational analysis system comprising a computer-readable medium containing a computer program for carrying out a subject method.

The present invention provides polypeptides that display selected epitope(s), e.g., antigenic polypeptides. For example, the present invention provides a polypeptide fragment of from about 5 to about 50 amino acids in length, which polypeptide displays one or more epitopes corresponding to an epitope or epitopes displayed by a bacterium, e.g., a pathogenic bacterium such as *Chlamydia*. The present invention further provides macromolecules comprising the antigenic polypeptides. The present invention further provides compositions, including immunogenic compositions, comprising the polypeptides or macromolecules. The subject antigenic polypeptides can be used in polypeptide arrays, for use in characterizing and/or classifying antibodies. The subject antigenic polypeptides can be used are also useful for generating antibodies, which antibodies are in turn useful in diagnostic devices and assays, which are also provided. The subject antigenic polypeptides are also useful for inducing an immune response to a pathogenic microorganism that displays an epitope displayed by a subject antigenic polypeptide. The present invention further provides methods of inducing an immune response to a *Chlamydia* in an individual. The method generally involves administering to the individual an effective amount of a subject immunogenic composition.

The subject methods are also useful for designing nucleic acids comprising nucleotide sequences that allow detection and/or classification of a bacterium, e.g., a pathogenic bacterium. Thus, the present invention provides a nucleic acid array for identifying *Chlamydia* serovar class or serovar, or for identifying *Chlamydia* strain or sub-strain; and for classifying a new isolate. The array comprises a plurality of member nucleic acids. A member nucleic acid comprises a nucleotide sequence comprising at least one nucleotide that is correlated with an epitope of a polypeptide encoded by the nucleotide sequence, where the polypeptide is one that contributes to serovar class, serovar, strain, or substrain.

The present invention further provides an array of antibodies, the array comprising a plurality of member antibodies, where each member antibody is specific for a different *Chlamydia* epitope. In many embodiments, the antibodies are attached to an insoluble support. Such arrays are useful for detecting and/or classifying *Chlamydia* present in a biological sample. The present invention further provides a device and a kit comprising a subject antibody array.

Methods of Classifying Epitopes

The present invention provides a method of classifying an epitope of a polypeptide. The method generally involves:

a) identifying a plurality of variable nucleotide positions in an alignment of nucleotide sequences of a plurality of variants of a polypeptide-coding sequence;

b) correlating a nucleotide character state of a plurality of variable nucleotide positions with a selected immunological reactivity, to generate a plurality of correlated nucleotide character states; and c) generating a plurality of reference sets comprising a plurality of correlated nucleotide states, wherein each correlated nucleotide state correlates with a selected immunological reactivity, and wherein the reference sets indicates an epitope classification of the encoded polypeptide.

The method is useful for classifying epitopes displayed on polypeptides that are members of a polypeptide family comprising multiple variants. Polypeptide families comprising multiple variants are known in the art, and include polypeptides associated with a pathogenic microorganism, e.g., a virus, a bacterium, a helminth, a protozoan, and the like. In some embodiments, the polypeptide is a member of a family of related polypeptides comprising members that differ from one another in amino acid sequence by from one to about 10 amino acids over a stretch of 50 contiguous amino acids.

Individual members of the family of polypeptides are distinguished from at least one other member of the family by immunological reactivity. In some embodiments, individual members of the family of polypeptides are distinguished from at least one other member of the family by antibody binding. For example, individual members of the family of polypeptides are distinguished from at least one other member of the family by differential binding to one or more antibodies, e.g., a panel of monoclonal antibodies, patient serum, polyclonal antibodies, etc. In these embodiments, the method provides a means of classifying B-cell epitopes on a polypeptide.

In other embodiments, individual members of the family of polypeptides are distinguished from at least one other member of the family by T cell binding. In these embodiments, the method provides a means of classifying T-cell epitopes on a polypeptide.

Of particular interest in many embodiments are polypeptides that are displayed on the surface of a virus, bacterium, protozoan, helminth, etc., and that are accessible to antibodies and/or T cell antigen receptors. Of particular interest in many embodiments are viral envelope proteins, viral group-specific antigen (gag) proteins, bacterial membrane proteins (e.g., bacterial outer membrane proteins), bacterial fimbriae proteins, bacterial flagellar proteins, protozoan surface antigens, and the like. Non-limiting examples of polypeptide families comprising multiple variants which are suitable for analysis using a subject method include, but are not limited to, human immunodeficiency virus (HIV) gp120 proteins, e.g., gp120 proteins of various HIV isolates (see, e.g., Rhyzova et al. (2002) *J. Virol.* 76:7903-7909); *Neisseria gonorrhoeae* outer membrane porin (Por); *Neisseria gonorrhoeae* outer membrane protein (Opa); *Neisseria gonorrhoeae* major fimbrial protein (PilE); *Neisseria meningitidis* outer membrane proteins; *Bordetella pertussis* pertactin (Prn); Influenza virus hemagglutinin; *Trypanosoma cruzi* variant surface glycoprotein (VSG); *Salmonella typhimurium* (O) antigens; *Salmonella typhimurium* flagellar (H) antigens; *Streptococcus pyogenes* M-proteins; *Chlamydia* membrane proteins; and the like.

*Chlamydia* membrane proteins include, but are not limited to, major outer membrane protein (MOMP); outer membrane complex B protein (OmcB); outer membrane complex A protein (OmcA); the nine polymorphic outer membrane proteins, e.g., polymorphic membrane protein-E, polymorphic membrane protein-H (see, e.g., Grimwood and Stephens (1999) *Microbial Comparative Genomics* 4:187-201); cytotoxin genes (Belland et al. (2001) *Proc Natl Acad Sci USA* 98:13984-13989); partial tryptophan operon proteins (TrpB/A) (Shaw et al. (2000) *Microbes Infect* 2:581-592.); Type III secretion system proteins (Hsia et al. (1997) *Mol. Microbiol.* 25:351-359), chlamydial protease- or proteasome-like activity factor (CPAF) (Zhong et al. (2001) *J Exp Med* 193:935-942); and PorB. (Kawa and Stephens (2002) *J. Immunol.* 168:5184-5191). In some embodiments of interest, the *Chlamydia* membrane protein is a *Chlamydia* major outer membrane protein (MOMP).

In general, nucleotide sequences encoding variant members of a polypeptide family are aligned; and variable nucleotide positions identified. A plurality of variable nucleotide positions are individually compared with available immunoreactivity data, e.g., serum reactivity, antibody reactivity, T-cell reactivity. A nucleotide character state of a plurality of variable nucleotide positions is correlated with a selected immunological reactivity, to generate a plurality of correlated nucleotide character states. Nucleotide character states include A (adenine); G (guanine); C (cytosine); T (thymine); Y (C or T); R (A or G); W (A or T); S (G or C); K (T or G); M (C or A); D (not C); V (not T); H (not G); and B (not A).

Once a plurality of correlated nucleotide character states is generated, a plurality of reference sets is generated. Each reference set comprises a plurality of correlated nucleotide states. Because the correlated nucleotide state correlate with a selected immunological reactivity, the reference sets classify epitopes of the encoded polypeptide. Each reference set provides nucleotide character state information on one or more epitopes.

In some embodiments, the method classifies epitopes associated with a *Chlamydia* serovar class, e.g., the reference sets classify epitopes of *Chlamydia* serovar classes B, C, and I. In some embodiments, the method classifies epitopes associated with a *Chlamydia* serovar, e.g., the reference sets classify epitopes of one or more of *Chlamydia* serovars B, Ba, D, Da, E, L1, L2, and L2a. In other embodiments, the reference sets classify epitopes of one or more of *Chlamydia* serovars A, C, H, I, Ia, J, Ja, K, and L3. In still other embodiments, the reference sets classify epitopes of one or more of *Chlamydia* serovars F, G, and Ga. In other embodiments, the reference sets classify epitopes of one or more strain or substrain.

In other embodiments, the method identifies a *Chlamydia* strain. In some embodiments, the method identifies a strain within *C. trachomatis*. For example, in some embodiments, the method distinguishes between or among *C. trachomatis* strains such as 434, A/Har-13, A/G-17/OT, B/TW-5/OT, Ba/Ap-2/OT, C/TW-3/OT, D/UW-3/Cx, Da/TW-448/Cx, D/TW-3/CX, D-/MT 157/Cx, E/UW-5/Cx, F/UW-6/Cx, G/UW-57/Cx, H/UW-4/Cx, I/UV-12/Ur, Ia/UW-202/NP, I-/MT 518/Cx, J/UW-36/Cx, K/UW-31/Cx, L1/440/Bu, L2/434/Bu, L2a/UW-396/Bu, and L3/404/Bu. In some embodiments, the method identifies a strain within *C. pneumoniae*. For example, in some embodiments, the method distinguishes between or among *C. pneumoniae* strains such as AR39, CWL029, LPConU, N16, P1, and TW-183. In some embodiments, the method identifies a strain within *C. psittaci*. For example, in some embodiments, the method distinguishes between or among *C. psittaci* strains such as Mn, 6BC, GPIC, FP, and OA. In some embodiments, the method identifies new strains and substrains of a particular species or genera of the family Chlamydiaciae.

Computer Program Product and Computational Analysis System

The present invention provides a computer program product for carrying out a subject method. The present invention also includes an algorithm for performing a subject method, where the algorithm is recorded on a computer readable medium. The present invention further provides computational analysis systems that include a subject computer program product.

One or more aspects of the above methodology may be in the form of computer readable media having programming stored thereon for implementing the subject methods. In other words, the subject methodology may be provided in the form of programming (a computer program product) or an algorithm recorded onto a computer readable medium. The computer readable media may be, for example, in the form of a computer disk or CD (compact disc), a floppy disc, a magnetic "hard card", a server, or any other computer readable media capable of containing data or the like, stored electronically, magnetically, optically or by other means. Accordingly, stored programming embodying steps for carrying-out the subject methods may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

In some embodiments, a subject computer-readable medium has recorded thereon a program (a computer program product) that: a) identifies a plurality of variable nucleotide positions in an alignment of nucleotide sequences of a plurality of variants of a polypeptide-coding sequence; b) correlates a nucleotide character state of a plurality of variable nucleotide positions with a selected immunological reactivity, to generate a plurality of correlated nucleotide character states; and c) generates a plurality of reference sets comprising a plurality of correlated nucleotide states, wherein each correlated nucleotide state correlates with a selected immunological reactivity, and wherein the reference sets classify epitopes of the encoded polypeptide.

In some embodiments, a subject computer-readable medium has recorded thereon a program (a computer program product) that: a) identifies a plurality of variable nucleotide positions in an alignment of nucleotide sequences of a plurality of variants of a polypeptide-coding sequence; b) correlates a nucleotide character state of a plurality of variable nucleotide positions with a selected immunological reactivity, to generate a plurality of correlated nucleotide character states; c) generates a plurality of reference sets comprising a plurality of correlated nucleotide states, wherein each correlated nucleotide state correlates with a selected immunological reactivity, and wherein the reference sets classify epitopes of the encoded polypeptide; and d) compares a test nucleotide sequence encoding a test polypeptide to the plurality of reference sets of correlated nucleotide character states and determining the best fit of the test nucleotide sequence to a reference set from among the plurality of reference sets, where an identity of at least 80% to a reference set associated with a selected epitope indicates that the test polypeptide exhibits the epitope.

In some embodiments, a subject computer-readable medium has recorded thereon a program (a computer program product) that: a) identifies a plurality of variable nucleotide positions in an alignment of nucleotide sequences of a plurality of variants of a polypeptide-coding sequence; b) correlates a nucleotide character state of a plurality of variable nucleotide positions with a selected immunological reactivity, to generate a plurality of correlated nucleotide character states; c) generates a plurality of reference sets comprising a plurality of correlated nucleotide states, wherein each correlated nucleotide state correlates with a selected immunological reactivity, and wherein the reference sets classify epitopes of the encoded polypeptide; and d) based on the reference sets, generates a nucleotide sequence that encodes a polypeptide that exhibits one or more selected epitopes from among the classified epitopes.

The present invention provides a computational analysis system comprising a subject computer-readable medium or a subject computer program product. In one embodiment of the subject invention, a system of the invention may include a single computer or the like with a stored algorithm capable of carrying out a subject method, i.e., a computational analysis system. In certain embodiments, the system is further characterized in that it provides a user interface, where the user interface presents to a user the option of selecting among one or more different, including multiple different, inputs, e.g., e.g., immunoreactivity data (e.g., serological data), nucleotide sequence data, and the like. Computational systems that may be readily modified to become systems of the subject invention include those described in U.S. Pat. No. 6,251,588; the disclosure of which is herein incorporated by reference.

Polypeptide Fragments and Compositions

The present invention provides antigenic polypeptide fragments, which fragments display one or more selected epitopes corresponding to epitopes displayed by one or more pathogenic microorganisms. The present invention further provides compositions, including immunogenic compositions, comprising the polypeptides. A subject antigenic polypeptide is typically isolated, and in many embodiments is synthetic.

A subject antigenic polypeptide fragment is generally from about 5 amino acids to about 60 amino acids in length, e.g., from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 40 amino acids to about 50, or from about 50 to about 60 amino acids in length.

In some embodiments, the amino acid sequence of a subject antigenic polypeptide is found in a naturally-occurring polypeptide that is associated with or produced by a pathogenic microorganism. In other embodiments, the amino acid sequence of a subject antigenic polypeptide is not found in a naturally-occurring polypeptide that is associated with or produced by a pathogenic microorganism.

Typically, a subject antigenic polypeptide is isolated, e.g., a subject antigenic polypeptide is substantially free of the materials with which it is associated in nature. By substantially free is meant at least 50%, at least 70%, at least 80%, or at least 90% free of the materials with which it is associated in nature. As used herein, an "isolated" polypeptide also refers to recombinant polypeptides, which, by virtue of origin or manipulation: (1) are not associated with all or a portion of a polypeptide with which it is associated in nature, (2) are linked to a polypeptide other than that to which it is linked in nature, or (3) does not occur in nature.

In many embodiments, a subject antigenic polypeptide is pure, e.g., a subject antigenic polypeptide is in a composition that is free of other polypeptides, e.g., a subject antigenic polypeptide is at least about 70% pure, at least about 80% pure, at least about 90% pure, at least about 95% pure, at least about 98% pure, at least about 99% pure, or greater than 99% pure.

A subject antigenic polypeptide displays one or more epitopes displayed by a pathogenic microorganism. In some embodiments, a subject antigenic polypeptide displays one or more B-cell epitopes (epitopes bound specifically by an antibody) displayed by a pathogenic microorganism. In some embodiments, a subject antigenic polypeptide displays one or more T-cell epitopes (epitopes bound specifically by a T cell antigen receptor) displayed by a pathogenic microorganism. In some embodiments, a subject antigenic polypeptide displays one or more B-cell epitopes and one or more T-cell epitopes.

In some embodiments, a subject antigenic polypeptide comprises one or more epitopes displayed on a *Chlamydia* membrane protein. In particular embodiments of interest, a subject antigenic polypeptide comprises one or more epitopes displayed on a *Chlamydia* major outer membrane protein.

In certain embodiments, a subject antigenic polypeptide is of Formula I:

```
FORMULA I
                                      (SEQ ID NO: 1)
X_aa1-X_aa2-X_aa3-X_aa4-X_aa5-X_aa6-X_aa7-X_aa8-X_aa9-X_aa10-

X_aa11-X_aa12-X_aa13-X_aa14-X_aa15-X_aa16-X_aa17-X_aa18X_aa19-

X_aa20-X_aa21-X_aa22-X_aa23-X_aa24-X_aa25-X_aa26-X_aa27,
``` wherein $X_{aa1}$ is A, V, or absent; $X_{aa2}$ is E, T, K, or absent; $X_{aa3}$ is A, T, P, or absent; $X_{aa4}$ is I, V, or absent; $X_{aa5}$ is F, L, V, or absent; $X_{aa6}$ is D or absent; $X_{aa7}$ is V, T, I, or absent; $X_{aa8}$ is T; $X_{aa9}$ is T; $X_{aa10}$ is L; $X_{aa11}$ is N; $X_{aa12}$ is P or R; $X_{aa13}$ is T; $X_{aa14}$ is T or I; $X_{aa15}$ is A or T; $X_{aa16}$ is G; $X_{aa17}$ is A, C, K, or absent; $X_{aa18}$ is G or absent; $X_{aa19}$ is S, G, T, A, E, D, or absent; $X_{aa20}$ is V or absent; $X_{aa21}$ is A, V, I, K, or absent; $X_{aa22}$ is A, G, S, T, or absent; $X_{aa23}$ is A, G, N, S, or absent; $X_{aa24}$ is G, N, or absent; $X_{aa25}$ is A, S, T, or absent; $X_{aa26}$ is D, E, or absent; and $X_{aa27}$ is G, N, or absent.

In some embodiments, a subject antigenic polypeptide is of Formula II:

```
NH_2-(X_1)_n(A/T)GT(D/E)A(X_2)_m-COOH    (SEQ ID NO: 2)
``` where $X_1$ and $X_2$ are independently any amino acid, and n and m are each independently zero, or an integer from 1 to about 44. In some embodiments, the amino-terminal (N-terminal) and/or the carboxyl-terminal (C-terminal) amino acid is a cysteine. In some embodiments, a subject antigenic polypeptide is of Formula I, and $(X_1)_n$ is LD(L/I)T. In some embodiments, a subject antigenic polypeptide is of Formula I, and $(X_1)_n$ is (L/I)T. In some embodiments, a subject antigenic polypeptide is of Formula I, and $(X_2)_m$ is TGT.

In some embodiments, a subject antigenic polypeptide comprises one of the following amino acid sequences:

| | |
|---|---|
| AGTEA; | (SEQ ID NO: 3) |
| AGTDA; | (SEQ ID NO: 4) |
| LDLTAGTDA; | (SEQ ID NO: 5) |
| LDLTAGTDAT; | (SEQ ID NO: 6) |
| DLTAGTDA; | (SEQ ID NO: 7) |
| LDITAGTEA; | (SEQ ID NO: 8) |
| LDITAGTEAT; | (SEQ ID NO: 9) |
| DITAGTEA; and | (SEQ ID NO: 10) |
| TGT(D/E)A. | (SEQ ID NO: 11) |

In some embodiments, a subject antigenic polypeptide is of Formula III:
NH$_2$—(X$_1$)$_n$TIAG(X$_2$)$_m$—COOH (SEQ ID NO:12), where X$_1$ and X$_2$ are independently any amino acid, and n and m are each independently zero, or an integer from 1 to about 56. In some embodiments, the N-terminal and/or the C-terminal amino acid is a cysteine.

In some embodiments, a subject antigenic polypeptide is of Formula IV:
NH$_2$—C—(X$_1$)$_n$TIAG(X$_2$)$_m$C—COOH (SEQ ID NO:13), where X$_1$ and X$_2$ are independently any amino acid, and n and m are each independently zero, or an integer from 1 to about 54.

In some embodiments, a subject antigenic polypeptide is of Formula V:
NH$_2$—(X$_1$)$_n$TTLNPTIAG(X$_2$)$_m$—COOH (SEQ ID NO:14), where X$_1$ and X$_2$ are independently any amino acid, and n and m are each independently zero, or an integer from 1 to about 41. In some embodiments, the N-terminal and/or the C-terminal amino acid is a cysteine.

In some embodiments, a subject antigenic polypeptide is of Formula VI:

```
NH_2-C(X_1)_nTTLNPTIAG(X_2)_m-C-COOH,   (SEQ ID NO:15)
``` where $X_1$ and $X_2$ are independently any amino acid, and n and m are each independently zero, or an integer from 1 to about 39.

In some embodiments, a subject antigenic polypeptide is of Formula III, IV, VI, or VI, and $(X_1)_n$ is AETIFDV (SEQ ID NO:16). In other embodiments, a subject antigenic polypeptide is of Formula III, IV, VI, or VI, and $(X_1)_n$ is AETILDV. In some embodiments, a subject antigenic polypeptide is of Formula III, IV, VI, or VI, and $(X_2)_m$ is (A/K)G(D/T)V(K/V)(T/S)(S/G)(A/S)(E/D)(G/N) (SEQ ID NO:17). In some embodiments, a subject antigenic polypeptide is of Formula III, IV, VI, or VI, and $(X_2)_m$ is AGDVKTSAEG (SEQ ID NO:18). In other embodiments, a subject antigenic polypeptide is of Formula III, IV, VI, or VI, and $(X_2)_m$ is AGDVKT-SAE (SEQ ID NO:19). In other embodiments, a subject antigenic polypeptide is of Formula III, IV, VI, or VI, and $(X_2)_m$ is KGTVVTSAE (SEQ ID NO:20). In other embodiments, a subject antigenic polypeptide is of Formula III, IV, VI, or VI, and $(X_2)_m$ is KGTVVSSAE (SEQ ID NO:21). In other embodiments, a subject antigenic polypeptide is of Formula III, IV, VI, or VI, and $(X_2)_m$ is KGTVV(A/S)SSAE (SEQ ID NO:22).

In some embodiments, a subject antigenic polypeptide comprises one of the following amino acid sequences:

| | |
|---|---|
| CTTLNPTIAGC; | (SEQ ID NO: 23) |
| AETIFDVTTLNPTIAG; | (SEQ ID NO: 24) |
| CAETIFDVTTLNPTIAGC; | (SEQ ID NO: 25) |
| AETIFDVTTLNPTIAGAGCVKTSAEG; | (SEQ ID NO: 26) |
| CAETIFDVTTLNPTIAGAGCVKTSAEGC; | (SEQ ID NO: 27) |
| AETILDVTTLNPTIAG; | (SEQ ID NO: 28) |
| CAETILDVTTLNPTIAGC; | (SEQ ID NO: 29) |
| TTLNPTIAGAGCVKTSAEG; | (SEQ ID NO: 30) |
| CTTLNPTIAGAGCVKTSAEGC; | (SEQ ID NO: 31) |
| TTLNPTIAGAGDVKTSAE; | (SEQ ID NO: 32) |
| CTTLNPTIAGAGDVKTSAEC; | (SEQ ID NO: 33) |
| TTLNPTIAGKGTVVTSAE; | (SEQ ID NO: 34) |
| CTTLNPTIAGKGTVVTSAEC; | (SEQ ID NO: 35) |
| TTLNPTIAGKGTVVSSAE; | (SEQ ID NO: 36) |
| CTTLNPTIAGKGTVVSSAEC; | (SEQ ID NO: 37) |
| TTLNPTIAGKGTVVASSAE; | (SEQ ID NO: 38) |
| CTTLNPTIAGKGTVVASSAEC; | (SEQ ID NO: 39) |

```
TTLNPTTLNPTIAGKGTVVASSAE;        (SEQ ID NO: 40)

CTIAGKGTVVASSAEC;                (SEQ ID NO: 41)

AETILDVTTLNPTIAGKGTVVTSAE;       (SEQ ID NO: 42)
and

CAETILDVTTLNPTIAGKGTVVTSAEC.     (SEQ ID NO: 43)
```

In some embodiments, a subject antigenic polypeptide is of Formula VII:

NH$_2$—(X$_1$)$_n$-GAKPT(T/A)(T/D)TGN(A/S)(V/T/A)AP-STLTARE-(X$_2$)$_m$—COOH (SEQ ID NO:44), where X$_1$ and X$_2$ are independently any amino acid, and n and m are each independently zero, or an integer from 1 to about 30. In some embodiments, the N-terminal and/or the C-terminal amino acid is a cysteine.

In some embodiments, a subject antigenic polypeptide is of Formula VIII:

```
                                  (SEQ ID NO: 45)
NH2-C-(X1)n-G(A/D)KPT(T/A/S)(T/D/A)TGN(A/S)(V/T/
A)AP(S/T)T(LC)TARE-(X2)m-C-COOH,
``` where X$_1$ and X$_2$ are independently any amino acid, and n and m are each independently zero, or an integer from 1 to about 28.

In some embodiments, a subject antigenic polypeptide is of Formula VII or VIII, and comprises the amino acid sequence GAKPTATTGNATAPSTLTARE (SEQ ID NO:46). In some embodiments, a subject antigenic polypeptide is of Formula VII or VIII, and comprises the amino acid sequence GAKPTTDTGNSAAPSTLTARE (SEQ ID NO:49).

In some embodiments, a subject antigenic polypeptide comprises one of the following amino acid sequences:

```
GAKPTATTGNATAPSTLTARE;           (SEQ ID NO:47)

CGAKPTATTGNATAPSTLTAREC;         (SEQ ID NO:48)

GAKPTTDTGNSAAPSTLTARE;           (SEQ ID NO:49)

CGAKPTTDTGNSAAPSTLTAREC;         (SEQ ID NO:50)

GAKPTTTTGNAVAPSTLTARE;           (SEQ ID NO:51)
and

CGAKPTTTTGNAVAPSTLTAREC.         (SEQ ID NO:52)
```

In some embodiments, a subject antigenic polypeptide is of Formula IX:

NH$_2$—(X$_1$)$_n$-TT(S/K)DVAGLQNDP-(X$_2$)$_m$—COOH (SEQ ID NO:53), where X$_1$ and X$_2$ are independently any amino acid, and n and m are each independently zero, or an integer from 1 to about 38. In some embodiments, the N-terminal and/or the C-terminal amino acid is a cysteine.

In some embodiments, a subject antigenic polypeptide is of Formula X:

NH$_2$—C—(X$_1$)$_n$-TT(S/K)DVAGLQNDP-(X$_2$)$_m$—C—COOH (SEQ ID NO:54), where X$_1$ and X$_2$ are independently any amino acid, and n and m are each independently zero, or an integer from 1 to about 36.

In some embodiments, a subject antigenic polypeptide is of Formula IX or Formula X, and —(X$_1$)$_n$— is GAAP (SEQ ID NO:55). In some embodiments, a subject antigenic polypeptide is of Formula IX or Formula X, and —(X$_2$)$_m$— is TTNVAAP (SEQ ID NO:56).

In some embodiments, a subject antigenic polypeptide comprises one of the following amino acid sequences:

```
TTSDVAGLQNDP;                    (SEQ ID NO:57)

CTTSDVAGLQNDPC;                  (SEQ ID NO:58)

GAAPTTSDVAGLQNDP;                (SEQ ID NO:59)

CGAAPTTSDVAGLQNDPC;              (SEQ ID NO:60)

TTSDVAGLQNDPTTNVAAP;             (SEQ ID NO:61)

CTTSDVAGLQNDPTTNVAAPC;           (SEQ ID NO:62)

GAAPTTSDVAGLQNDPTTNVAAP;         (SEQ ID NO:63)
and

CGAAPTTSDVAGLQNDPTTNVAAPC.       (SEQ ID NO:64)
```

In some embodiments, a subject antigenic polypeptide is of Formula XI:

NH$_2$—(X$_1$)$_n$-(S/A)EFTINKPKGYVG(K/Q/A/V)E-(X$_2$)$_m$—COOH (SEQ ID NO:65), where X$_1$ and X$_2$ are independently any amino acid, and n and m are each independently zero, or an integer from 1 to about 38. In some embodiments, the N-terminal and/or the C-terminal amino acid is a cysteine.

In some embodiments, a subject antigenic polypeptide comprises one of the following amino acid sequences:

```
SEFTINKPKGYVGKE;                 (SEQ ID NO:66)

SEFTINRPKGYVGAE;                 (SEQ ID NO:67)

SEFTINKPKGYVGVE;                 (SEQ ID NO:68)
and

AEFTINKPKGYVGQE.                 (SEQ ID NO:69)
```

In some embodiments, a subject antigenic polypeptide is of Formula XII:

NH$_2$—(X$_1$)$_n$-ILWEGFGGDPCDPCTT-(X$_2$)$_m$—COOH (SEQ ID NO:70), where X$_1$ and X$_2$ are independently any amino acid, and n and m are each independently zero, or an integer from 1 to about 34.

In some embodiments, a subject antigenic polypeptide is of Formula XIII:

NH$_2$—(X$_1$)$_n$-ALNIWDRFDV-(X$_2$)$_m$—COOH (SEQ ID NO:71), where X$_1$ and X$_2$ are independently any amino acid, and n and m are each independently zero, or an integer from 1 to about 40.

In some embodiments, a subject antigenic polypeptide is of Formula XIV:

```
                                  (SEQ ID NO:72)
NH2-(X1)n-KMKSRKSCGIAVGTTVSADKYAVT-(X2)m-COOH,
``` where X$_1$ and X$_2$ are independently any amino acid, and n and m are each independently zero, or an integer from 1 to about 26.

Subject polypeptides are useful in a variety of contexts. In some embodiments, a subject antigenic polypeptide is useful for inducing an immune response to a pathogenic microorganism such as a pathogenic *Chlamydia*, e.g., *Chlamydia trachomatis, Chlamydia pneumoniae, Chlamydia psittaci, C. suis, C. caviae, C. muridarum*, etc. Thus, the present invention provides immunogenic compositions comprising a subject antigenic polypeptide and/or a subject antigenic macromolecule (described below). In other embodiments, a subject antigenic polypeptide is useful in diagnostic applications, e.g., in the context of identification of a *Chlamydia* infection, and in classification of a *Chlamydia* bacterium found in, or isolated from, a biological sample. In other embodiments, a subject antigenic polypeptide is useful in research applications, e.g., in classification of a *Chlamydia* bacterium found in, or isolated from, a biological sample.

Antigenic Macromolecules Comprising a Subject Antigenic Polypeptide

The present invention further provides an antigenic macromolecule that comprises a subject antigenic polypeptide, as described above; and a heterologous macromolecule. Suitable heterologous macromolecules include, but are not limited to, polypeptides (including glycoproteins, lipoproteins, etc.); lipids; polysaccharides; lipopolysaccharides; nucleic acids; and other organic macromolecules. In some embodiments, the heterologous macromolecule is one that is not a ligand for a cell surface receptor.

In some embodiments, the heterologous macromolecule is a polypeptide other than the epitope-displaying subject antigenic polypeptide, e.g., the heterologous macromolecule is a polypeptide that does not contain the epitope-displaying subject antigenic polypeptide. In some embodiments, the heterologous macromolecule is a polypeptide not associated with the pathogenic microorganism that displays an epitope displayed by the epitope-displaying subject antigenic polypeptide. In some embodiments, the heterologous macromolecule is other than a translocation domain, e.g., the heterologous macromolecule does not contain a translocation domain. In some embodiments, the heterologous macromolecule is other than a receptor-binding domain, e.g., the heterologous macromolecule does not contain a receptor-binding domain.

In one embodiment, the heterologous macromolecule is a carrier, e.g., a protein, a peptide, a T cell adjuvant or any other compound capable of enhancing the immune response. The carrier may be selected from a viral protein, a bacterial protein, a parasite protein, an animal protein, a synthetic protein, a recombinant protein, and a fungal protein. In one embodiment, the carrier is albumin. Alternatively, the carrier is tetanus toxoid, diphtheria toxoid, meningococcal outer membrane protein complexes (see, e.g., U.S. Pat. No. 4,707,543; U.S. Pat. No. 6,476,201; U.S. Pat. No. 6,558,677), or a bacterial outer protein (such as recombinant *N. meningitidis* porin B). Such carriers may be obtained from biochemical or pharmaceutical supply companies or prepared by standard methodology (Cruse, J M (ed.) Conjugate Vaccines in Contributions to Microbiology and Immunology vol. 10 (1989)). Synthetic peptides containing T-cell epitopes suitable for use as a carrier may include "universal" T cell epitope (Panina-Bordignon et al 1989 Eur J Immunol 19:2237) or non-natural Pan DR Epitope peptides (PADRE) (del Guercio et al 1997 Vaccine 15:441). Other agents include other proteins which can function as carriers, which agents would be known to those of ordinary skill in the art of immunology.

In some embodiments, the heterologous macromolecule is a nucleic acid. The polypeptide can be attached to the 3'-end of the nucleic acid through solid support chemistry. For example, the nucleic acid portion can be added to a polypeptide that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the nucleic acid can be synthesized such that it is connected to a solid support through a cleavable linker extending from the 3'-end. Upon chemical cleavage of the nucleic acid from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the nucleic acid (Nelson et al. (1989) *Nucleic Acids Res.* 17:1781-1794). Conjugation of the amino-modified nucleic acid to amino groups of the peptide can be performed as described in Benoit et al. (1987) *Neuromethods* 6:43-72. Conjugation of the thiol-modified nucleic acid to carboxyl groups of the peptide can be performed as described in Sinha et al. (1991), pp. 185-210, *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The polypeptide can be attached to the 5'-end of the nucleic acid through an amine, thiol, or carboxyl group that has been incorporated into the nucleic acid during its synthesis. For example, while the nucleic acid is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the nucleic acid to a polypeptide. Benoit et al. (1987) supra; and Sinha et al. (1991) supra.

In some embodiments, a subject antigenic polypeptide is attached to a heterologous macromolecule directly. In other embodiments, a subject antigenic polypeptide is attached to a heterologous macromolecule via a linker, e.g., a linker is interposed between the subject antigenic polypeptide and the heterologous macromolecule. Suitable linkers include, but are not limited to, straight or branched-chain carbon linkers, heterocyclic carbon linkers, substituted carbon linkers, unsaturated carbon linkers, aromatic carbon linkers, peptide linkers, etc.

In embodiments where a linker is used to connect a subject antigenic polypeptide to a heterologous macromolecule, the linker can be attached to the antigenic polypeptide and/or the heterologous macromolecule by any means or method known by one of skill in the art without limitation. For example, the linker can be attached to the antigenic polypeptide and/or the heterologous macromolecule with an ether, ester, thioether, thioester, amide, imide, disulfide, or other suitable moiety. The skilled artisan can select the appropriate linker and means for attaching the linker based on the physical and chemical properties of the chosen antigenic polypeptide and the heterologous macromolecule. The linker can be attached to any suitable functional group on the receptor binding domain or the remainder of the molecule. For example, the linker can be attached to sulfhydryl (—S), carboxylic acid (COOH) or free amine (—$NH_2$) groups, which are available for reaction with a suitable functional group on a linker. These groups can also be used to connect the antigenic polypeptide to the heterologous macromolecule in the absence of a linker.

In some embodiments, e.g., where the heterologous macromolecule is a polypeptide, the linker is a peptide. The linker peptide may have any of a variety of amino acid sequences. Proteins can be joined by a spacer peptide, generally of a flexible nature, although other chemical linkages are not excluded. Suitable linker sequences will generally be peptides of between about 5 and about 50 amino acids in length, or between about 6 and about 25 amino acids in length. These linkers are generally produced by using synthetic, linker-encoding oligonucleotides to couple the proteins. Peptide linkers with a degree of flexibility will generally be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art.

Suitable linker peptides can include amino acid sequences rich in alanine and proline residues, which are known to impart flexibility to a protein structure. Exemplary linkers for use in a subject antigenic polypeptide have a combination of glycine, alanine, proline and methionine residues, such as AAAGGM (SEQ ID NO:73); AAAGGMPPAAAGGM (SEQ ID NO:74); AAAGGM (SEQ ID NO:75); and PPAAAGGM (SEQ ID NO:76). However, any flexible linker generally between about 5 and about 50 amino acids in length may be used. Linkers may have virtually any sequence that results in a generally flexible peptide, including alanine-proline rich sequences of the type exemplified above.

Polypeptide Arrays

The present invention provides polypeptide arrays, comprising a plurality of subject polypeptides. A subject polypeptide array is useful for detecting and characterizing antibodies specific for a Chlamydia polypeptide. A subject polypeptide array comprises a substrate with a surface comprising a plurality of subject polypeptides with different, known sequences bound to the surface in positionally defined locations. Typically, each of the plurality of polypeptides has a different amino acid sequence. In some embodiments, a subject polypeptide substrate comprises a plurality of member polypeptides, each having a different amino acid sequence, where each member is present on the substrate in one or more copies, and where each member, or multiple copies of each member, is present in a positionally defined location. Examples of suitable polypeptide arrays, and methods for generating same, are described in, e.g., U.S. Pat. No. 6,919,211.

A subject polypeptide is present in a subject array at a density of from about 10 to about 50, from about 50 to about 100, from about 100 to about 200, from about 200 to about 300, from about 300 to about 400, from about 400 to about 500, from about 500 to about 750, or from about 750 to about 1000 different polypeptides occupying a total area of less than 1 $cm^2$ on the substrate. In some embodiments, the substrate of a subject array comprises from about $10^2$ to about $10^3$, from about $10^3$ to about $10^4$, from about $10^4$ to about $10^5$, or from about $10^5$ to about $10^6$, or more, different polypeptides with known sequences bound to positionally defined locations of the substrate.

In many embodiments, the polypeptides are covalently attached to the surface. In some embodiments, the polypeptides are attached to the surface via a linker.

The substrate is typically a solid support. Suitable solid supports include strands, precipitates, gels, sheets, tubing, spheres, containers, membranes, capillaries, pads, slices, films, plates and slides. A solid support is of any of a variety of materials, including, but not limited to, polymers, plastics, resins, polysaccharides, silica or silica-based materials, carbon, metals, and inorganic glasses.

A subject polypeptide array is useful for detecting and/or characterizing antibody specific for a Chlamydia serovar, serovar class, strain, or substrain. Antibodies are reacted with a subject array, and specific binding of an antibody (e.g., a test antibody, e.g., a test antibody present in a biological sample) to a polypeptide within a subject polypeptide array is detected. Specific binding is readily detected by standard methods, e.g., by using a detectably labeled secondary antibody specific for the Fc portion of a test antibody. Binding of a test antibody may be compared to a reference, e.g., a positive control such as an antibody with known specificity for a subject polypeptide, detected using a detectably labeled antibody specific for the Fc portion of the positive control antibody.

Methods of Making a Subject Antigenic Polypeptide

A subject antigenic polypeptide can be generated synthetically, using standard methods of peptide synthesis; or can be generated using well-established recombinant methods, e.g., using a nucleic acid comprising a nucleotide sequence encoding the polypeptide to generate a recombinant vector, which is introduced into a suitable host cell for synthesis of the encoded polypeptide.

Any suitable expression system known by one of skill in the art for producing a peptide, polypeptide, or nucleic acid antigen can be used to produce the Chlamydia antigens of the invention. To produce recombinant peptide Chlamydia antigens, the nucleic acid sequences encoding the antigens can be inserted into a suitable expression system. In some embodiments, a recombinant construct or vector is constructed in which a nucleotide sequence encoding the selected protein, e.g., a Chlamydia antigen, is operably linked to a heterologous expression control sequence, permitting production of the protein in a host cell genetically modified with the recombinant vector. Numerous types of appropriate expression vectors are known in the art for protein expression by standard molecular biology techniques. Such vectors can be selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, e.g., Sambrook et al., 2001, *Molecular Cloning—A Laboratory Manual*, 3$^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY, and references cited therein.

Suitable host cells or cell lines for transfection by this method include bacterial cells, such as, for example, *E. coli* (e.g., HB101, MC1061, etc.) *B. subtilis*, *Pseudomonas* ssp., *Streptomyces* ssp., and the like; and mammalian cells, such as, for example, human 293 cells, Chinese hamster ovary cells (CHO), monkey COS-1 cells, and murine 3T3 cells. Indeed, any suitable host cell, method for transfection, culture, amplification, screening, production, purification, etc. known to one of skill in the art can be used to produce a Chlamydia antigen. Further, strains of yeast cells or other fungal systems known to those skilled in the art are also available as host cells for expression of the antigens of the present invention. Alternatively, insect cells such as *Spodoptera frugipedera* (Sf9) cells may be used.

Thus, the present invention provides a method for producing recombinant Chlamydia antigen that comprises transfecting, e.g., by conventional means such as electroporation, a host cell with at least one expression vector containing a polynucleotide encoding the Chlamydia antigen under the control of a transcriptional regulatory sequence. The transfected or transformed host cell can be then cultured under conditions that allow expression of the protein. The expressed protein can be recovered, isolated, and optionally purified from the cell (or from the culture medium, if expressed extracellularly) by appropriate means known to one of skill in the art.

For example, the antigens can be isolated in soluble form following cell lysis, or extracted using known techniques, e.g., in guanidine chloride. If desired, the proteins or fragments of the invention are produced as a fusion protein such as those described above. Alternatively, for example, it may be desirable to produce fusion proteins to enhance expression of the antigen in a selected host cell, to improve purification, or for use in monitoring the presence of the antigen in tissues, cells or cell extracts. Suitable fusion partners for the proteins of the invention are well known to those of skill in the art and include, among others, β-galactosidase, glutathione-S-transferase, poly-histidine and maltose binding protein.

Thus, the invention also provides a method for preparing a *Chlamydia* antigenic polypeptide of the invention by transforming a host cell using an expression vector (plasmid, cosmid, virus, etc.) comprising DNA sequences encoding the antigens of the invention, and culturing the transformed host cell and recovering the peptide in the culture medium.

The invention further provides a vector (either cloning and/or expression) and a host cell (prokaryotic or eukaryotic) transformed ("genetically modified") by the vector and comprising regulating elements allowing expression of the nucleotide sequence coding for a antigen of the invention.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region.

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast).

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters (promoters functional in a eukaryotic cell) include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A subject recombinant vector will in some embodiments include one or more selectable markers. In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Generally, recombinant expression vectors will include origins of replication and selectable markers permitting transformation of the host cell, e.g., the ampicillin resistance gene of *E. coli*, the *S. cerevisiae* TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In some embodiments, a nucleotide sequence encoding a subject antigenic polypeptide will be operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2): 327-34); and the like.

In some embodiments, a nucleotide sequence encoding a subject antigenic polypeptide will be operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

A subject recombinant vector may be introduced into a host cell utilizing a vehicle, or by various physical methods. Representative examples of such methods include transformation using calcium phosphate precipitation (Dubensky et al., PNAS, 81:7529-7533 (1984)), direct microinjection of such nucleic acid molecules into intact target cells (Acsadi et al., Nature, 352:815-818 (1991)), and electroporation whereby cells suspended in a conducting solution are subjected to an intense electric field in order to transiently polarize the membrane, allowing entry of the nucleic acids. Other procedures include the use of nucleic acid molecules linked to an inactive adenovirus (Cotton et al., PNAS, 89:6094 (1990)), lipofection (Felgner et al., Proc. Natl. Acad. Sci. USA, 84:7413-7417 (1989)), microprojectile bombardment (Williams et al., PNAS, 88:2726-2730 (1991)), polycation compounds such as polylysine, receptor specific ligands, liposomes entrapping the nucleic acid molecules, and spheroplast fusion whereby *E. coli* containing the nucleic acid molecules are stripped of their outer cell walls and fused to animal cells using polyethylene glycol.

Compositions

The present invention provides compositions, including immunogenic compositions, comprising one or more of the above-described polypeptides or macromolecules. A subject composition comprises one or more subject antigenic polypeptides or macromolecules, and may further include one or more of the following: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Compositions comprising a subject antigenic polypeptide(s) or macromolecule may include a buffer, which is selected according to the desired use of the antigenic polypeptide(s), and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995) Mack Publishing Co.

Pharmaceutical compositions can be prepared in various forms, such as granules, tablets, pills, suppositories, capsules, suspensions, sprays, suppositories, transdermal applications (e.g., patches, etc.), salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

When used as an immunogenic composition, a subject antigenic polypeptide(s) can be formulated in a variety of ways. In general, an immunogenic composition of the invention is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a subject immunogenic composition may be formulated to contain other components, including, e.g., adjuvants, stabilizers, pH adjusters, preservatives and the like. Such components are well known to those of skill in the vaccine art. Adjuvants include, but are not limited to, aluminum salt adjuvants (Nicklas (1992) *Res. Immunol.* 143:489-493); saponin adjuvants; Ribi's adjuvants (Ribi ImmunoChem Research Inc., Hamilton, Mont.); Montanide ISA adjuvants (Seppic, Paris, France); Hunter's TiterMax adjuvants (CytRx Corp., Norcross, Ga.); Gerbu adjuvants (Gerbu Biotechnik GmbH, Gaiberg, Germany); and nitrocellulose (Nilsson and Larsson (1992) *Res. Immunol.* 143:553-557). In addition, other components that may modulate an immune response may be included in the formulation, including, but not limited to, cytokines, such as interleukins; colony-stimulating factors (e.g., GM-CSF, CSF, and the like); and tumor necrosis factor.

In some embodiments, a subject antigenic polypeptide composition comprises an adjuvant. Examples of known suitable adjuvants that can be used in humans include, but are not necessarily limited to, alum, aluminum phosphate, aluminum hydroxide, MF59 (4.3% w/v squalene, 0.5% w/v Tween 80, 0.5% w/v Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g WO 00/56358; (6) combinations of 3dMPL with, for example, QS21 and/or oil-in-water emulsions e.g EP-A-0835318, EP-A-0735898, EP-A-0761231; (7) oligonucleotides comprising CpG motifs (Krieg Vaccine 2000, 19, 618-622; Krieg Curr opin Mol Ther 2001 3:15-24; Roman et al., Nat. Med., 1997, 3, 849-854; Weiner et al., PNAS USA, 1997, 94, 10833-10837; Davis et al, J. Immunol, 1998, 160, 870-876; Chu et al., J. Exp. Med, 1997, 186, 1623-1631; Lipford et al, Ear. J. Immunol., 1997, 27, 2340-2344; Moldoveanu et al., Vaccine, 1988, 16, 1216-1224, Krieg et al., Nature, 1995, 374, 546-549; Klinman et al., PNAS USA, 1996, 93, 2879-2883; Ballas et al, J. Immmunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157, 4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581] i.e. containing at least one CG dinucleotide, where the cytosine is unmethylated; (8) a polyoxyethylene ether or a polyoxyethylene ester e.g WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally+a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

A subject composition may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The concentration of a subject antigenic polypeptide in a subject composition can vary widely, e.g., from less than about 0.1%, usually at or at least about 2% to as much as 20% to 50% or more by weight, and will be selected primarily by fluid volumes, viscosities, etc., in accordance with the particular mode of administration selected.

In some embodiments, a subject antigenic polypeptide composition comprises one or more polypeptides that exhibit one or more Chlamydia serovar class B epitopes. In some embodiments, a subject antigenic polypeptide composition comprises one or more polypeptides that exhibit one or more Chlamydia serovar class B epitopes, where the epitopes are B-cell epitopes. In some of these embodiments, a subject composition comprises one or more of the following subject antigenic polypeptides from one or more of the following groups:

```
Group 1)
GAKPTATTGNATAPSTLTARE;      (SEQ ID NO:46)

CGAKPTATTGNATAPSTLTAREC;    (SEQ ID NO:48)

GAKPTTDTGNSAAPSTLTARE;      (SEQ ID NO:49)

CGAKPTTDTGNSAAPSTLTAREC;    (SEQ ID NO:50)

GAKPTTTTGNAVAPSTLTARE;      (SEQ ID NO:51)
and

CGAKPTTTTGNAVAPSTLTAREC.    (SEQ ID NO:52)

Group 2)
AGTDA;                      (SEQ ID NO:4)

LDLTAGTDA;                  (SEQ ID NO:5)

LDLTAGTDAT;                 (SEQ ID NO:6)
and

DLTAGTDA.                   (SEQ ID NO:7)

Group 3)
AETIFDVTTLNPTIAG;           (SEQ ID NO:24);

CAETIFDVTTLNPTIAGC;         (SEQ ID NO:25)

AETIFDVTTLNPTIAGAGCVKTSAEG; (SEQ ID NO:26)
``` and

CAETIFDVTTLNPTIAGAGCVKTSAEGC.    (SEQ ID NO:27)

In some embodiments, a subject antigenic polypeptide composition comprises one polypeptide from Group 1; one polypeptide from Group 2; and one polypeptide from Group 3. In some embodiments, a subject antigenic polypeptide composition comprises two polypeptides from Group 1; two polypeptides from Group 2; and two polypeptides from Group 3.

In some embodiments, a subject antigenic polypeptide composition comprises one or more polypeptides that exhibit one or more *Chlamydia* serovar class C epitopes. In some embodiments, a subject antigenic polypeptide composition comprises one or more polypeptides that exhibit one or more *Chlamydia* serovar class C epitopes, where the epitopes are B-cell epitopes. In some of these embodiments, a subject antigenic polypeptide composition comprises one or more subject antigenic polypeptides comprising amino acid sequences from one or more of the following groups:

Group 4)

TTSDVAGLQNDP; (SEQ ID NO:57)

CTTSDVAGLQNDPC; (SEQ ID NO:58)

GAAPTTSDVAGLQNDP; (SEQ ID NO:59)

CGAAPTTSDVAGLQNDPC; (SEQ ID NO:60)

TTSDVAGLQNDPTTNVAAP; (SEQ ID NO:61)

CTTSDVAGLQNDPTTNVAAPC; (SEQ ID NO:62)

GAAPTTSDVAGLQNDPTTNVAAP; (SEQ ID NO:63)
and

CGAAPTTSDVAGLQNDPTTNVAAPC. (SEQ ID NO:64)

Group 5)

AGTEA (SEQ ID NO:3)

LDITAGTEA (SEQ 1D NO:8)

LDITAGTEAT (SEQ ID NO:9)

DITAGTEA; (SEQ ID NO:10)
and

Group 6)

AETILDVTTLNPTIAG; (SEQ ID NO:28)

CAETILDVTTLNPTIAGC; (SEQ ID NO:29)

AETILDVTTLNPTIAGKGTVVTSAE; (SEQ ID NO:42)
and

CAETILDVTTLNPTIAGKGTVVTSAEC. (SEQ ID NO:43)

In some embodiments, a subject antigenic polypeptide composition comprises one polypeptide from Group 4; one polypeptide from Group 5; and one polypeptide from Group 6. In some embodiments, a subject antigenic polypeptide composition comprises two polypeptides from Group 4; two polypeptides from Group 5; and two polypeptides from Group 6.

In some embodiments, any of the above-described compositions will further comprise one or more polypeptides that exhibit one or more *Chlamydia* T-cell epitopes. Antigenic polypeptides displaying one or more *Chlamydia* T-cell epitopes do not necessarily distinguish between or among *Chlamydia* serovar classes. For example, in some embodiments, any of the above-described compositions will further comprise one or more of the following polypeptides:

SEFTINKPKGYVGKE; (SEQ ID NO:66)

SEFTINKPKGYVGAE; (SEQ ID NO:67)

SEFTINKPKGYVGVE; (SEQ ID NO:68)

AEFTINKPKGYVGQE; (SEQ ID NO:69)

ILWEGFGGDPCDPCTT; (SEQ ID NO:70)

ALNIWDRFDV; (SEQ ID NO:71)
and

KMKSRKSCGIAVGTTVSADKYAVT. (SEQ ID NO:72)

In some embodiments, a subject composition comprises the following polypeptides:

AGTDA; (SEQ ID NO:4)

CAETIFDVTTLNPTIAGAGCVKTSAEGC; (SEQ ID NO:27)
and

CGAKPTATTGNATAPSTLTAREC. (SEQ ID NO:48)

In some of these embodiments, a subject composition further comprises one or more of the following polypeptides:

SEFTINKIPKGYVGKE; (SEQ ID NO:66)

ILWEGFGGDPCDPCTT; (SEQ ID NO:70)

ALNIWDRFDV; (SEQ ID NO:71)
and

KMKSRKSCGIAVGTTVSADKYAVT. (SEQ ID NO:72)

In some embodiments, a subject composition comprises the following polypeptides:

ADTEA; (SEQ ID NO:77)
and

CTTSDVAGLQNDPC. (SEQ ID NO:58)

In some of these embodiments, a subject composition further comprises one or more of the following polypeptides:

SEFTINRPKGYVGKE; (SEQ ID NO:66)

ILWEGFGGDPCDPCTT; (SEQ ID NO:70)

ALNIWDRFDV; (SEQ ID NO:71)
and

KMKSRKSCGIAVGTTVSADKYAVT. (SEQ ID NO:72)

In some embodiments, a subject composition comprises the following polypeptides:

AGTDA; (SEQ ID NO:4)

ADTEA; (SEQ ID NO:77)

CAETIFDVTTLNPTIAGAGCVKTSAEGC; (SEQ ID NO:27)

```
CGAKPTATTGNATAPSTLTAREC;          (SEQ ID NO:48)
and

CTTSDVAGLQNDPC.                   (SEQ ID NO:58)
```

In some of these embodiments, a subject composition further comprises one or more of the following polypeptides:

```
SEFTINKPKGYVGKE;                  (SEQ ID NO:66)

ILWEGFGGDPCDPCTT;                 (SEQ ID NO:70)

ALNIWDRFDV;                       (SEQ ID NO:71)
and

KMKSRKSCGIAVGTTVSADKYAVT.         (SEQ ID NO:72)
```

Methods of Inducing an Immune Response

The present invention provides methods of inducing an immune response in an individual. The methods generally involve administering to an individual an effective amount of a subject antigenic polypeptide. In general, administration is accomplished by any suitable route, including administration of a subject composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that a subject antigenic polypeptide or a subject antigenic macromolecule described above, when administered orally, should be protected from digestion. This is typically accomplished either by complexing the polypeptide with a composition to render it resistant to acidic and enzymatic hydrolysis or by packaging in an appropriately resistant carrier such as a liposome. Means of protecting a compound of interest from digestion are well known in the art.

In order to enhance serum half-life, the antigenic preparations that are administered are in some embodiments encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the antigen preparations as a mixture or in serial fashion.

A subject composition administered to a subject that has or is at risk from acquiring a Chlamydial disease to induce an immune response to Chlamydia. A subject method is effective to prevent or at least partially arrest the development of disease and its complications. An amount adequate to accomplish this is defined as a "therapeutically effective dose" or an "immunogenically effective dose." Amounts effective for therapeutic use will depend on, e.g., the antigen composition, the manner of administration, the weight and general state of health of the patient, and the judgment of the prescribing physician. Single or multiple doses of the antigen compositions may be administered depending on the dosage and frequency required and tolerated by the patient, and route of administration.

The terms "stimulating an immune response," and "inducing an immune response," as used herein, include one or more of the following: 1) stimulating production of antibodies that bind specifically to the antigenic polypeptide in the immunogenic composition as well as a live Chlamydia bacterium that displays the epitope(s) displayed by the antigenic polypeptide; 2) stimulating a CD4 T cell response specific for the antigenic polypeptide in the immunogenic composition as well as a live Chlamydia bacterium that displays the epitope(s) displayed by the antigenic polypeptide; 3) stimulating a CD8 cytotoxic T lymphocyte (CTL) immune response specific for the antigenic polypeptide in the immunogenic composition as well as a live Chlamydia bacterium that displays the epitope(s) displayed by the antigenic polypeptide; and 4) stimulating a protective immune response following challenge (e.g., infection) with a live Chlamydia bacterium that displays the epitope(s) displayed by the antigenic polypeptide. In many embodiments, the immune response induced provides for protective immunity to Chlamydia.

In some embodiments, a subject method of inducing an immune response to a Chlamydia in an individual results in generation of a humoral (antibody) immune response. In some embodiments, a subject method of inducing an immune response to a Chlamydia in an individual results in generation of a cellular immune response, e.g., induction of CTL specific for a Chlamydia epitope(s). In some embodiments, a subject method of inducing an immune response to a Chlamydia in an individual results in generation of both a humoral and a cellular immune response. In some embodiments, a subject method of inducing an immune response to a Chlamydia in an individual results in generation of a mucosal immune response, e.g., induction of mucosal antibodies (e.g., IgA), induction of mucosal CTL, etc. A mucosal immune response refers to an immune response that occurs at a mucosal surface and/or in a mucosal tissue. Mucosal tissues include oral tissues, vaginal tissue, cervical tissue, rectal tissues, etc. In many embodiments, a subject method is effective to reduce or prevent adherence of a Chlamydia to an epithelial cell of the subject.

Whether an immune response to a Chlamydia is induced is readily determined using any of a variety of standard assay methods. Whether an antibody response to a Chlamydia antigen has been induced in an individual is readily determined using standard assays. For example, immunological assays such as enzyme-linked immunosorbent assays (ELISA), radioimmunoassay (RIA), immunoprecipitation assays, and protein blot ("Western" blot) assays; and neutralization assays (e.g., neutralization of Chlamydia infection of an epithelial cell in an in vitro or in vivo assay); can be used to detect the presence of antibody specific for a Chlamydia antigen in a bodily fluid or other biological sample.

Whether a CD4 immune response to a Chlamydia antigen has been induced in an individual is readily determined using standard assays, e.g., fluorescence-activated cell sorting (FACS) (see, e.g., Waldrop et al. (1997) J. Clin. Invest. 99:1739-1750); intracellular cytokine assays that detect production of cytokines following antigen stimulation (see, e.g., Suni et al. (1998) J. Immunol. Methods 212:89-98; Nomura et al. (2000) Cytometry 40:60-68; Ghanekar et al. (2001) Clin. Diagnostic Lab. Immunol. 8:628-631); MHC-peptide multimer staining assays, e.g., use of detectably labeled (e.g., fluorescently labeled) soluble MHC Class II/peptide multimers (see, e.g., Bill and Kotzin (2002) Arthritis Res. 4:261-265; Altman et al. (1996) Science 274:94-96; and Murali-Krishna et al. (1998) Immunity 8:177-187); enzyme-linked immunospot (ELISPOT) assays (see, e.g., Hutchings et al. (1989) J. Immunol. Methods 120:1-8; and Czerkinsky et al. (1983) J.

*Immunol. Methods* 65:109-121); and the like. As one non-limiting example of an intracellular cytokine assay, whole blood is stimulated with antigen and co-stimulating antibodies (e.g., anti-CD28, anti-CD49d) for 2 hours or more; Brefeldin A is added to inhibit cytokine secretion; and the cells are processed for FACS analysis, using fluorescently labeled antibodies to CD4 and to cytokines such as TNF-α, IFN-γ and IL-2.

Whether an antigen-specific CD8 (e.g., cytotoxic T cell; "CTL") response is induced to a *Chlamydia* can be determined using any of a number of assays known in the art, including, but not limited to, measuring specific lysis by CTL of target cells expressing an antigen of the intracellular pathogen on their surface, which target cells have incorporated a detectable label which is released from target cells upon lysis, and can be measured, using, e.g., a $^{51}$Cr-release assay; a lanthanide fluorescence-based cytolysis assay; and the like.

Immunization Regimen

In some embodiments, a single immunization will suffice to induce an immune response to *Chlamydia*. In other embodiments, a subject composition is administered serially.

In some embodiments, serial doses of a subject immunogenic composition are administered. First, an immunogenically effective dose of a subject antigenic polypeptide is administered to a subject. The first dose is generally administered in an amount effective to elicit an immune response (e.g., activation of B cells and/or T cells). Amounts for the initial immunization generally range from about 0.001 mg to about 1.0 mg per 70 kilogram patient, e.g., from about 0.001 mg to about 0.2 mg per 70 kilogram patient, or from about 0.005 mg to about 0.015 mg per 70 kilogram patient. Dosages from 0.001 mg up to about 10 mg per patient per day may be used, particularly when the polypeptide is administered to a secluded site and not into the blood stream, such as into a body cavity or into a lumen of an organ. Substantially higher dosages (e.g. 10 mg to 100 mg or more) are possible in oral, nasal, or topical administration.

After administration of the first dose of a subject antigenic polypeptide, a therapeutically effective second dose of a subject antigenic polypeptide is administered to the subject after the subject has been immunologically primed by exposure to the first dose. The booster may be administered days, weeks or months after the initial immunization, depending upon the patient's response and condition.

The existence of an immune response to the first dose may be determined by known methods (e.g. by obtaining serum from the individual before and after the initial immunization, and demonstrating a change in the individual's immune status, for example an immunoprecipitation assay, an enzyme-linked immunosorbent assay (ELISA), a bactericidal assay, a Western blot assay, a flow cytometric assay, and the like) and/or demonstrating that the magnitude of the immune response to the second dose is higher than that of control animals immunized for the first time with the composition of matter used for the second injection (e.g. immunological priming). Immunologic priming and/or the existence of an immune response to the first dose may also be assumed by waiting for a period of time after the first immunization that, based on previous experience, is a sufficient time for an immune response and/or priming to have taken place—e.g. 2 weeks, 4 weeks, 6 weeks, 10 weeks, or 14 weeks. Boosting dosages of the second dose are typically from about 0.001 mg to about 1.0 mg of antigen, depending on the nature of the immunogen and route of immunization.

The existence of priming and/or an immune response to the second dose may be determined by the same methods used to detect an immune response to the second dose. The existence of priming and/or an immune response to the second dose may also be assumed by waiting for a period of time after the second immunization that, based on previous experience, is a sufficient time for an immune response to have taken place—e.g. 2 weeks, 4 weeks, 6 weeks, 10 weeks, or 14 weeks. Boosting dosages of the second dose are typically from about 0.001 mg to about 1.0 mg of antigen, depending on the nature of the immunogen and route of immunization.

The present invention further contemplates the use of a fourth, fifth, sixth or subsequent booster immunization, using, e.g., a fourth, fifth, sixth, or subsequent dose.

In one embodiment, the antigen compositions can be administered to a mammalian subject (e.g., human) that is immunologically naïve with respect to *Chlamydia* (e.g., *C. trachomatis*). In a particular embodiment, the mammal is a human pre-pubescent female, a human adolescent female, or an adult human female, and the antigen compositions are administered at any one or more of the following times: at 9 years, 10 years, 11 years, 12 years, 13 years, 14 years, 15 years, 16 years, 17 years, 18 years, 19 years, or 20 years of age. Administration of a subject composition to a human female under the age of 9 years, or older than the age of 20 years, is also contemplated. In another particular embodiment, the mammal is a human male. In another particular embodiment, the mammal is a human neonate, e.g., where the mother of the neonate has been diagnosed as having a *Chlamydia* infection. For example, in a particular embodiment, the human neonate is one day, from about two days to about 10 days, or from about 10 days to about 14 days old. In a particular embodiment, the mammal is a human child about ten years or younger, e.g., about five years old or younger, and the antigen compositions are administered at any one or more of the following times: two weeks, one month, 2 months, 3 months, 4 months, 5 months, 6 months, 7 months, 8 months, 9 months, 10 months, 11 months, 12 months, 15 months, 18 months, or 21 months after birth, or at 2 years, 3 years, 4 years, 5 years, 6 years, 7 years, 8 years, 9 years, or 10 years of age. In some embodiments, a subject immunogenic composition is administered to an individual in the age range of from about 6 months to about 6 years, where the individual receives a first dose at about 6 months of age, and subsequent booster doses, e.g., 2-3 subsequent booster doses, at, e.g., 2 years of age, 4 years of age, and 6 years of age. In some embodiments, a subject immunogenic composition is administered to a pre-sexual human subject. In some embodiments, a subject immunogenic composition is administered to a pregnant human female who has been diagnosed as having a *Chlamydia* infection. In some embodiments, a subject immunogenic composition is administered to a sexually active individual, e.g., a sexually active female human, a sexually active male human.

In some embodiments, a subject composition is administered to an individual shortly after contact (e.g., sexual contact; contact via a birth canal) with an individual who is known to have or suspected to have a *Chlamydia* infection. For example, in some embodiments, a subject composition is administered to an individual within about 1 hour, within about 2 hours, within about 5 hours, within about 8 hours, within about 12 hours, within about 18 hours, within about 24 hours, within about 2 days, within about 4 days, within about 7 days, within about 2 weeks, or within about one month after contact (e.g., sexual contact; contact via a birth canal) with an individual who is known to have or suspected to have a *Chlamydia* infection.

Nucleic Acid Arrays

The present invention provides nucleic acids that are useful for detecting and classifying *Chlamydia*. The present invention also provides nucleic acid arrays that are useful for detecting and classifying *Chlamydia*.

A subject nucleic acid array comprises an array of probe nucleic acids immobilized on a solid support surface. Nucleic acid probes are generally oligonucleotides, e.g. oligonucleotides of at least about 12 nucleotides (nt), at least about 15 nt, at least about 18 nt, at least about 20 nt, at least about 25 nt, at least about 30 nt, at least about 40 nt, at least about 50 at least about, at least about 60 nt, or longer. Such an array may comprise a series of oligonucleotides, each of which can specifically hybridize to a different *Chlamydia* outer membrane protein-encoding nucleic acid, each representing a different *Chlamydia* serovar class or *Chlamydia* serovar, strain, substrain, or other genera or species of the family Chlamydiaceae.

In some embodiments, a subject nucleic acid array is an array of probe nucleic acids in which the three serovar classes of *Chlamydia* are represented.

Oligonucleotide probes that identify *Chlamydia* serovar class C include nucleotide positions that distinguish *Chlamydia* serovar class C from *Chlamydia* serovar class B and I. Oligonucleotide probes that identify *Chlamydia* serovar class C include, but are not limited to:

5'-$(N)_x$-CCTACT(A/G)(C/T)CA(G/A)(C/A)GAT(A/G)(C/T)AG(C/A)GGGCTTA(T/C)(C/A)AAAC GATCCAACAACAAATGTTGCTCGTCCA-$N)_y$-3' (SEQ ID NO:78), corresponding to nucleotides in VS1, where residues in bold are correlated with serovar class C, and where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class C comprises one or more of the following:

(SEQ ID NO:79)
5'-$(N)_x$-CCTACTACCAGCGATACAGCGGGCTTATCAAACGATCCAACAACAAATGTTGCTCGTCCA-$(N)_y$-3';

(SEQ ID NO:80)
5'-$(N)_x$-CCTACTGTCAGCGATACAGCGGGCTTATCAAACGATCCAACAACAAATGTTGCTCGTCCA-$(N)_y$-3', (SEQ ID NO:81)
5'$(N)_x$-CCTACTACCAAGGATACAGCGGGCTTATCAAACGATCCAACAACAAATGTTGCTCGTCCA-$(N)_y$-3';

(SEQ ID NO:82)
5'-$(N)_x$-CCTACTACCAACGATACAGCGGGCTTATCAAACGATCCAACAACAAATGTTGCTCGTCCA-$(N)_y$-3';

(SEQ ID NO:83)
5'-$(N)_x$-CCTACTACCAGAGATACAGCGGGCTTATCAAACGATCCAACAACAAATGTTGCTCGTCCA-$(N)_y$-3';

(SEQ ID NO:84)
5'-$(N)_x$-CCTACTACCAGCGATGTAGCGGGCTTATCAAACGATCCAACAACAAATGTTGCTCGTCCA-$(N)_y$-3';

(SEQ ID NO:85)
5'-$(N)_x$-CCTACTACCAGCGATGTAGAGGGCTTATCAAACGATCCAACAACAAATGTTGCTCGTCCA-$(N)_y$-3';

-continued (SEQ ID NO:86)
5'-$(N)_x$-GCGATACAGCGGGCTTATCAAACGATCCAACAACAAATGTTGCTCGTCCA-$(N)_y$-3';

(SEQ ID NO:87)
5'-$(N)_x$-GGGCTTATCAAACGATCCAACAACAAATGTTGCTCGTCCA-$(N)_y$-3';

(SEQ ID NO:88)
5'-$(N)_x$-AACGATCCAACAACAAATGTTGCTCGTCCA-$(N)_y$-3';

(SEQ ID NO:89)
5'-$(N)_x$-CAACAAATGTTGCTCGTCCA-$(N)_y$-3'.

Oligonucleotide probes that identify *Chlamydia* serovar class C also include:

5'-$(N)_x$-ACATTGGGAGCAACTACCGGTTATTTAAAAGGAAACTCCGCT-$(N)_y$-3' (SEQ ID NO:90), corresponding to residues in a region between VS1 and VS2, where residues in bold are correlated with serovar class C, and where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class C comprises one or more of the following:

(SEQ ID NO:91)
5-$(N)_x$-ACATTGGGAGCAACTACCGGTTATTTAAAA-$(N)_y$-3';
and (SEQ ID NO:92)
5'-$(N)_x$-TGTACATTGGGAGCAACTACCGGTTATTTAAAA-$(N)_y$-3'.

Oligonucleotide probes that identify *Chlamydia* serovar class C also include:

5'-$(N)_x$-AAGCCGAAAGGATATGTTGGGG(C/T)GGAATTTCCACTTGATATTACCGCAGGAACAGAAGCT-$(N)_y$-3' (SEQ ID NO:93) corresponding to residues in VS3, where residues in bold are correlated with serovar class C, and where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class C comprises one or more of the following:

(SEQ ID NO:94)
5'-AAGCCGAAAGGATATGTTGGGGCGGAATTTCCACTTGATAT-3';

(SEQ ID NO:95)
5'-AAGCCGAAAGGATATGTTGGGGTGGAATTTCCACTTGATAT-3';

(SEQ ID NO:96)
5'-GTTGGGGCGGAATTTCCACTTGATATTACCGCAGGAACAGAAGCT-3';
and (SEQ ID NO:97)
5'-GTTGGGGTGGAATTTCCACTTGATATTACCGCAGGAACAGAAGCT-3'.

Oligonucleotide probes that identify *Chlamydia* serovar class C also include:

5'-$(N)_x$-GCTGGTAAAGGA(A/G)(G/C)TGTGGTC(G/T)CTTCC(G/T)(G/C)(C/A)AGCGA(A/T)AA CGA(A/C)CTGGCT-$(N)_y$-3' (SEQ ID NO:98) corresponding to residues in VS4, where residues in bold are correlated with serovar class C, and where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class C comprises one or more of the following:

5'-GCTGGTAAAGGAAGTGTGGTCGCTTCCGGCAGCGAAAACGAACTGGCT-3'; (SEQ ID NO:99)
and

5'-GCTGGTAAAGGAGCTGTGGTCTCTTCCGGAAGCGATAACGAACTGGCT-3'; (SEQ ID NO:100)

Oligonucleotide probes that identify *Chlamydia* serovar class B include nucleotide positions that distinguish *Chlamydia* serovar class B from *Chlamydia* serovar class C and I. Oligonucleotide probes that identify *Chlamydia* serovar class B include, but are not limited to:

5'-(N)$_x$-ACA(A/G)(C/G)T(A/G)(C/A)TACAGGCAAT(G/A)(C/G)T(G/A)(T/C)AGCTCCATCCACT (C/T)(T/G)TACAGCAAGAGAG-(N)$_y$-3' (SEQ ID NO:101) corresponding to residues in VS1, where residues in bold are correlated with serovar class B (and not with serovar class C or serovar class I), and where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class B comprises one or more of the following:

5'-ACAACTACTACAGGCAATGCTGTAGCTCCATCCACTCTTACAGCAAGAGAG-3'; (SEQ ID NO:102)

5'-ACAGCTACTACAGGCAATGCTACAGCTCCATCCACTCTTACAGCAAGAGAG-3'; (SEQ ID NO:103)

5'-ACAACTGATACAGGCAATAGTGCAGCTCCATCCACTCTTACAGCAAGAGAG-3'; (SEQ ID NO:104)
and

5'-ACAACTGCTACAGGCAATGCTGCAGCTCCATCCACTTGTACAGCAAGAGAG-3'. (SEQ ID NO:105)

Oligonucleotide probes that identify *Chlamydia* serovar class B also include:

5'-(N)$_x$-GGAGCTGGCGA(T/G)GTGAAA(A/G)CT(A/G)(G/A)C(G/A)CAGAGGGTCAGCTCGGA GAC-(N)$_y$-3' (SEQ ID NO:106) corresponding to residues in VS4, where residues in bold are correlated with serovar class B (and not with serovar class C or serovar class I), and where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class B comprises one or more of the following:

5'-GGAGCTGGCGATGTGAAAACTAGCGCAGAGGGTCAGCTCGGAGAC-3'; (SEQ ID NO:107)

5'-GGAGCTGGCGAGGTGAAAGCTAACGCAGAGGGTCAGCTCGGAGAC-3'; (SEQ ID NO:108)

5'-GGAGCTGGCGATGTGAAAACTGGCAGAGAGGGTCAGCTCGGAGAC-3'; (SEQ ID NO:109)
and

5'-GGAGCTGGCGATGTGAAAGTAGCGCAGAGGGTCAGCTCGGAGAC-3'. (SEQ ID NO:110)

Oligonucleotide probes that identify *Chlamydia* serovar class I include nucleotide residues that distinguish *Chlamydia* serovar class I from *Chlamydia* serovar class B and *Chlamydia* serovar class C. Oligonucleotide probes that identify *Chlamydia* serovar class I include, but are not limited to:

5'-(N)$_x$-ATGGGCGAGGCTTTAGCCGGAGCTTCTGGGAATACGACCTCTACTCTTTCAAAAT TGGTAGAACGAACGAACCCT-(N)$_y$-3' (SEQ ID NO:111) where x and y are each independently zero, or an integer from 1 to about 20, e.g., from about 1 to about 5, from about 5 to about 10, from about 10 to about 15, or from about 15 to about 20.

In particular embodiments, oligonucleotide probes that identify *Chlamydia* serovar class I comprises one or more of the following:

5'-GGCGAGGCTTTAGCCGGAGCTTCTGGGAATACGACCTCTACTCTTTCAAAATTGGTAGAACGAACGAAC-3'; (SEQ ID NO:112)

5'-AATACGACCTCTACTCTTTCAAAATTGGTAGAACGAACGAAC-3'; (SEQ ID NO:113)
and

5'-ATGGGCGAGGCTTTAGCCGGAGCTTCTGGG-3'. (SEQ ID NO:114)

In some embodiments, a subject nucleic acid array includes: one or more nucleic acids that distinguish *Chlamydia* serovar class C from *Chlamydia* serovar class B and *Chlamydia* serovar class I; one or more nucleic acids that distinguish *Chlamydia* serovar class B from *Chlamydia* serovar class C and *Chlamydia* serovar class I; and one or more nucleic acids that distinguish *Chlamydia* serovar class I from *Chlamydia* serovar class B and *Chlamydia* serovar class C.

In some embodiments, a subject nucleic acid array includes: one or more nucleic acids that distinguish between or among *Chlamydia* serovars.

Oligonucleotide probes that identify *Chlamydia* serovar E include nucleotide positions that distinguish *Chlamydia* serovar E from one or more of *Chlamydia* serovars B, Ba, D, Da, E, L1, L2, and L2a. Oligonucleotide probes that identify *Chlamydia* serovar E include, but are not limited to:

5'-(N)$_x$-ATGGGTGACAAGCCTACAAGTACT-(N)$_y$-3' (SEQ ID NO:115), where x and y are each independently zero, or an integer from 1 to about 20, e.g., from about 1 to about 5, from about 5 to about 10, from about 10 to about 15, or from about 15 to about 20;

5'-(N)$_x$-GTCAAAACGAATTCTGTACCA-(N)$_y$-3' (SEQ ID NO:116), where x and y are each independently zero, or an integer from 1 to about 20, e.g., from about 1 to about 5, from about 5 to about 10, from about 10 to about 15, or from about 15 to about 20; and 5'-(N)$_x$-GCACTCATAGCAGGAACT-(N)$_y$-3' (SEQ ID NO:117), where x and y are each independently zero, or an integer from 1 to about 20, e.g., from about 1 to about 5, from about 5 to about 10, from about 10 to about 15, or from about 15 to about 20.

Oligonucleotide probes that identify *Chlamydia* serovar B include nucleotide positions that distinguish *Chlamydia* serovar B from one or more of *Chlamydia* serovars Ba, D, Da, E, L1, L2, and L2a. Oligonucleotide probes that identify *Chlamydia* serovar B include, but are not limited to:

5'-$(N)_x$-CTTACAGCAGGAACA-$(N)_y$-3' (SEQ ID NO:118), where x and y are each independently zero, or an integer from 1 to about 20, e.g., from about 1 to about 5, from about 5 to about 10, from about 10 to about 15, or from about 15 to about 20.

Oligonucleotide probes that identify *Chlamydia* serovar Ba include nucleotide positions that distinguish *Chlamydia* serovar B from one or more of *Chlamydia* serovars B, D, Da, E, L1, L2, and L2a. Oligonucleotide probes that identify *Chlamydia* serovar Ba include, but are not limited to:

5'-$(N)_x$-CTTACATCAGGAACA-$(N)_y$-3' (SEQ ID NO:119), where x and y are each independently zero, or an integer from 1 to about 20, e.g., from about 1 to about 5, from about 5 to about 10, from about 10 to about 15, or from about 15 to about 20.

Oligonucleotide probes that identify *Chlamydia* serovar L1 include nucleotide positions that distinguish *Chlamydia* serovar L1 from *Chlamydia* serovars B, Ba, D, Da, E, L2, and L2a. Oligonucleotide probes that identify *Chlamydia* serovar L1 include, but are not limited to:

5'-$(N)_x$-GTCAAAAAGGATGCTGTA-$(N)_y$-3' (SEQ ID NO:120), where x and y are each independently zero, or an integer from 1 to about 20, e.g., from about 1 to about 5, from about 5 to about 10, from about 10 to about 15, or from about 15 to about 20; and 5'-$(N)_x$-GGCGAGGTGAAAGCTAACGCA-$(N)_y$-3' (SEQ ID NO:121), where x and y are each independently zero, or an integer from 1 to about 20, e.g., from about 1 to about 5, from about 5 to about 10, from about 10 to about 15, or from about 15 to about 20.

Oligonucleotide probes that identify *Chlamydia* serovar A include nucleotide positions that distinguish *Chlamydia* serovar A from one or more of *Chlamydia* serovars C, H, I, Ia, J, Ja, K, and L3. Oligonucleotide probes that identify *Chlamydia* serovar A include, but are not limited to:

5'-$(N)_x$-CCAGTAGTAAATGTTGCT-$(N)_y$-3' (SEQ ID NO:122), where x and y are each independently zero, or an integer from 1 to about 20, e.g., from about 1 to about 5, from about 5 to about 10, from about 10 to about 15, or from about 15 to about 20; and 5'-$(N)_x$-TCTGGCTTTGATACA-$(N)_y$-3' (SEQ ID NO:123), where x and y are each independently zero, or an integer from 1 to about 20, e.g., from about 1 to about 5, from about 5 to about 10, from about 10 to about 15, or from about 15 to about 20.

Oligonucleotide probes that identify *Chlamydia* serovar C include nucleotide positions that distinguish *Chlamydia* serovar A from one or more of *Chlamydia* serovars A, H, I, IA, J, Ja, K, and L3. Oligonucleotide probes that identify *Chlamydia* serovar A include, but are not limited to:

5'-$(N)_x$-CCAACAATAAACGTTGCT-$(N)_y$-3' (SEQ ID NO:124), where x and y are each independently zero, or an integer from 1 to about 20, e.g., from about 1 to about 5, from about 5 to about 10, from about 10 to about 15, or from about 15 to about 20; and 5'-$(N)_x$-TCTGCCGGAACCGAT-$(N)_y$-3' (SEQ ID NO:125), where x and y are each independently zero, or an integer from 1 to about 20, e.g., from about 1 to about 5, from about 5 to about 10, from about 10 to about 15, or from about 15 to about 20.

Oligonucleotide probes that identify *Chlamydia* serovar L3 include nucleotide positions that distinguish *Chlamydia* serovar L3 from one or more of *Chlamydia* serovars C, A, H, I, IA, J, Ja, and K.

Other oligonucleotides that distinguish between or among *Chlamydia* serovars are apparent from the data presented in FIGS. 9 and 10.

A variety of different array formats are known in the art, with a wide variety of different probe structures, substrate compositions and attachment technologies. Representative array structures of interest include those described in U.S. Pat. Nos. 6,919,211, 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

Essentially, any conceivable substrate for a subject nucleic acid may be employed. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is typically flat but may take on a variety of alternative surface configurations. For example, the substrate may contain raised or depressed regions on which the synthesis takes place. The substrate and its surface in many embodiments form a rigid support on which to carry out the hybridization reactions described herein. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In an exemplary embodiment, the substrate is flat glass or single-crystal silicon with surface relief features of less than 10 μm.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, or the like.

Surfaces on the solid substrate will in many embodiments be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. In many embodiments, the surface will contain reactive groups, which could be carboxyl, amino, hydroxyl, or the like. In many embodiments, the surface will be optically transparent and will have surface Si—OH functionalities, such as are found on silica surfaces.

A number of methods are available for creating microarrays of nucleic acids to be used in DNA hybridization assays. Exemplary are PCT Application Serial No. WO95/35505, published Dec. 28, 1995; U.S. Pat. No. 5,445,934, issued Aug. 29, 1995; and Drmanac et al. (1993) *Science* 260:1649-1652. Yershov et al. (1996) *Genetics* 93:4913-4918 describe an alternative construction of an oligonucleotide array. The construction and use of oligonucleotide arrays is reviewed by Ramsay (1998) supra. Methods of using high density oligonucleotide arrays are known in the art. For example, Milosavljevic et al. (1996) *Genomics* 37:77-86 describe DNA sequence recognition by hybridization to short oligomers.

The systems and kits of the subject invention may include the above-described arrays. The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In some embodiments, a subject nucleic acid array provides for detection of *Chlamydia* in a biological sample. In these embodiments, a subject nucleic acid array comprises one or more nucleic acid probes that detect *Chlamydia* serovar class B; one or more nucleic acid probes that detect *Chlamydia* serovar class C; and one or more nucleic acid probes that detect *Chlamydia* serovar class I. In some embodiments, a subject nucleic acid array comprises one or more nucleic acid probes that detect two or more *Chlamydia* strains and/or one or more nucleic acid probes that detect two or more *Chlamydia* substrains.

Methods for Detecting/Characterizing *Chlamydia*

The present invention provides methods for detecting *Chlamydia* in a biological sample; and methods of characterizing any detected *Chlamydia*, e.g., characterizing detected *Chlamydia* by serovar class and/or serovar and/or strain and/or substrain. The methods generally involve contacting a biological sample with a subject nucleic acid array; and detecting hybridization of nucleic acid present in the biological sample with a nucleic acid in the array. In practicing the subject diagnostic methods, the sample obtained from a subject is assayed to determine the presence of *Chlamydia* and/or to identify the serovar class and/or the serovar of any *Chlamydia* detected in the sample and/or to identify the strain or substrain of any *Chlamydia* detected in the sample.

Any convenient protocol for assaying a sample for the presence of a nucleic acid that hybridizes with a nucleic acid in a subject array may be employed in the subject methods. For example, a polynucleotide sample derived from (e.g., obtained from) an individual is employed. Any biological sample that comprises a polynucleotide from the individual is suitable for use in the methods of the invention. The biological sample may be processed so as to isolate the polynucleotide. Alternatively, whole cells or other biological samples may be used without isolation of the polynucleotides contained therein. A test nucleic acid sample can be amplified with primers which amplify a region known to comprise the target nucleic acid, e.g., primers that amplify a nucleic acid encoding a *Chlamydia* major outer membrane protein. Genomic DNA or mRNA can be used directly. The target nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfand, and Sninsky, eds., Academic Press.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Detection of hybridization between a nucleic acid in a subject array and a nucleic acid in the biological sample derived from an individual can be accomplished by any means known in the art. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Detection of a *Chlamydia* nucleic acid in a nucleic acid sample can be performed by hybridizing a sample and control nucleic acids to a subject nucleic acid array. Cronin et al. (1996) *Human Mutation* 7:244-255; and Kozal et al. (1996) *Nature Med.* 2:753-759.

In some embodiments, a subject method is a hybridization assay in which a subject nucleic acid array that displays "probe" nucleic acids for *Chlamydia* serovar class and/or serovar to be assayed/profiled in the profile to be generated is employed. In these assays, a sample of target nucleic acids (*Chlamydia* MOMP-encoding nucleic acid) is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the information (e.g., information regarding the presence of (or absence from) *Chlamydia* in a sample; and/or the serovar class of any *Chlamydia* detected in the sample; and/or the serovar of any *Chlamydia* detected in the sample; and/or the strain or substrain of any *Chlamydia* detected in the sample) includes the technology described in U.S. Pat. Nos. 5,143, 854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. Contact between a probe and a target nucleic acid is carried out under hybridization conditions, e.g., stringent hybridization conditions, and unbound nucleic acid is then removed.

Antibodies

The present invention provides antibodies specific for one or more *Chlamydia* epitopes. The present invention provides an array of antibodies, each specific for a different *Chlamydia* epitope. In some embodiments, the antibodies are polyclonal antibodies. In many embodiments, the antibodies are monoclonal antibodies. In many embodiments, the antibodies are attached to an insoluble support, e.g., in a subject antibody diagnostic device, as described in more detail below.

In some embodiments, a subject antibody array provides for detection of *Chlamydia* of any serovar class, e.g., a subject antibody array provides for detection of *Chlamydia* of serovar class B, class C, and class I. In these embodiments, a subject antibody array includes one or more antibodies specific for an epitope that identifies *Chlamydia* serovar class B; one or more antibodies specific for an epitope that identifies *Chlamydia* serovar class C, and one or more antibodies specific for an epitope that identifies *Chlamydia* serovar class I.

In some embodiments, a subject antibody array provides for detection of *Chlamydia* of one or more of the 19 serovars. In some embodiments, a subject antibody array provides for detection of a *Chlamydia* strain(s) and/or substrain(s).

Antibodies may be attached, directly or indirectly (e.g., via a linker molecule) to a solid support for use in a diagnostic assay to detect a *Chlamydia* polypeptide in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an ELISA or radioimmunoassay (RIA), and the like); sheets, e.g., nylon, nitrocellulose, and the like; and chips, e.g., $SiO_2$ chips such as those used in microarrays. Accordingly, the invention further provides assay devices comprising antibodies attached to a solid support.

Methods of Generating an Antibody

Suitable antibodies are obtained by immunizing a host animal with peptides comprising all or a portion of the target protein. Suitable host animals include mouse, rat sheep, goat, hamster, rabbit, etc. A subject antigenic polypeptide is used to immunize a host.

For preparation of polyclonal antibodies, the first step is immunization of the host animal with the target protein (e.g., a subject antigenic polypeptide), where the target protein will usually be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil-and-water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal (e.g., a rodent, such as a mouse) provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the antigenic protein include mouse, rat, hamster, etc. To raise antibodies against the antigenic protein, the animal will generally be a mouse, rat, hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *Proc. Natl. Acad. Sci. USA.* 84:3439 and (1987) *J. Immunol.* 139: 3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies which are identical to human antibodies may be employed. By xenogenic human antibodies is meant antibodies that are the same has human antibodies, i.e. they are fully human antibodies, with exception that they are produced using a non-human host which has been genetically engineered to express human antibodies. See e.g. WO 98/50433; WO 98,24893 and WO 99/53049, the disclosures of which are herein incorporated by reference.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Antibody Diagnostic Devices

The present invention provides diagnostic devices comprising one or more antibodies specific for a *Chlamydia* epitope, e.g., an epitope displayed on one or more subject antigenic polypeptides. The diagnostic devices will in some embodiments provide information as to whether a biological sample obtained from an individual contains *Chlamydia* or a polypeptide or polypeptide fragment derived from *Chlamydia*, and thus provides information as to whether the individual has a *Chlamydia* infection. The diagnostic devices will in some embodiments provide information as to the *Chlamydia* serovar class or *Chlamydia* serovar or *Chlamydia* strain or substrain with which the individual is infected.

Suitable immunodiagnostic techniques include, but are not necessarily limited to, assays such as competition, direct reaction, or sandwich type assays. Such assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include revealing labels such as fluorescent, chemiluminescent, radioactive, enzymatic labels or dye molecules, or other methods for detecting the formation of a complex between a *Chlamydia* polypeptide in the sample and the antibody or antibodies reacted therewith.

The aforementioned assays generally involve separation of unbound antibody in a liquid phase from a solid phase support to which *Chlamydia* polypeptide-antibody complexes are bound. Solid supports which can be used in a subject device include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., an anti-*Chlamydia* polypeptide antibody) under suitable binding conditions such that the component is sufficiently immobilized to the support. Sometimes, immobilization to the support can be enhanced by first coupling the antibody to a protein with better binding properties, or that provides for immobilization of the antibody on the support without significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like. Such molecules, and methods of coupling these molecules to the antibody, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing ligand moieties (e.g., a *Chlamydia* polypeptide) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

In some embodiments, a subject device suitable for an ELISA. For example, the wells of a microtiter plate are coated with anti-*Chlamydia* polypeptide antibody according to the present invention. A biological sample containing or suspected of containing *Chlamydia* polypeptide, is then added to the coated wells. After a period of incubation sufficient to allow antibody binding, the plate(s) can be washed to remove unbound *Chlamydia* polypeptide and a detectably labeled secondary binding molecule added. The secondary binding molecule is allowed to react with any captured antigen, the plate washed and the presence of the secondary binding molecule detected using methods well known in the art. In other related embodiments, competitive-type ELISA techniques can be practiced using methods known to those skilled in the art.

The presence of bound *Chlamydia* polypeptide from a biological sample can be readily detected using a secondary binder comprising an antibody directed against the *Chlamydia* polypeptide. In general, the *Chlamydia* polypeptide antibody will be detectably labeled, either directly or indirectly. Direct labels include radioisotopes; enzymes whose products are detectable (e.g., luciferase, β-galactosidase, horse radish peroxidase, alkaline phosphatase, and the like); proteins that provide a detectable signal (e.g., a fluorescent protein, such as a green fluorescent protein (GFP) derived from *Aequoria victoria* or a derivative thereof; a GFP from another species such as *Renilla reniformis*, *Renilla mulleri*, or *Ptilosarcus*

*guernyi*, as described in, e.g., WO 99/49019 and Peelle et al. (2001) J. Protein Chem. 20:507-519; any of a variety of fluorescent and colored proteins from Anthozoan species, as described in, e.g., Matz et al. (1999) Nature Biotechnol. 17:969-973; and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; and the like.

Assays can also be conducted in solution, such that the antibodies and *Chlamydia* polypeptide form complexes under precipitating conditions. In one particular embodiment, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing *Chlamydia* polypeptide to provide for formation of particle-antibody-*Chlamydia* polypeptide complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In some embodiments, a subject diagnostic device comprises at least a sample application region and a *Chlamydia* polypeptide detection zone; and will be composed of a membrane capable of conducting fluid flow, such as a nitrocellulose membrane strip. Optionally, the membrane may be provided on a rigid or semi-rigid supporting surface, such as a polyethylene strip. In some embodiments, a preabsorption zone will be interposed between the sample application region and the *Chlamydia* polypeptide detection zone, where the preabsorption zone includes antibodies specific for polypeptides that cross-react with a *Chlamydia* polypeptide, which cross-reactive polypeptides are not derived from or associated with *Chlamydia*. The location of the zones will be such that lateral flow of fluid along the membrane causes all the components of the sample to come into contact with the detection zone. Where a subject device comprises a preabsorption zone the location of the zones will be such that lateral flow of fluid along the membrane causes all the components of the sample to come into contact with the preabsorption zone first, then the detection zone. Fluid flow along the membrane from the sample application region towards the detection zone is facilitated by capillary action across the membrane. Exemplary lateral flow assay devices and detection methods employing the lateral flow assay devices are provided in, for example, U.S. Pat. No. 6,146,589, the disclosure of which is incorporated herein by reference.

In one representative embodiment, the detection zone has immobilized thereon an antibody specific one or more *Chlamydia* epitopes. Detection of the presence or absence of *Chlamydia* polypeptides in the biological sample is carried out by first adding the sample to the sample application region and allowing the sample to migrate by capillary action across the membrane strip. As the sample migrates across the membrane strip, the sample migrates to the detection zone, where it comes into contact with immobilized *Chlamydia* epitope-specific antibody. The presence or absence of *Chlamydia* polypeptides bound to the immobilized *Chlamydia* epitope-specific antibody is then detected using a detectably labeled secondary binding molecule as described above. The secondary binding molecule is allowed to react with any captured *Chlamydia* polypeptide(s) (e.g., *Chlamydia* polypeptides bound to *Chlamydia* epitope-specific antibody immobilized on the membrane), and the presence of the secondary binding molecule detected using methods described above and well known in the art.

Figure 11:
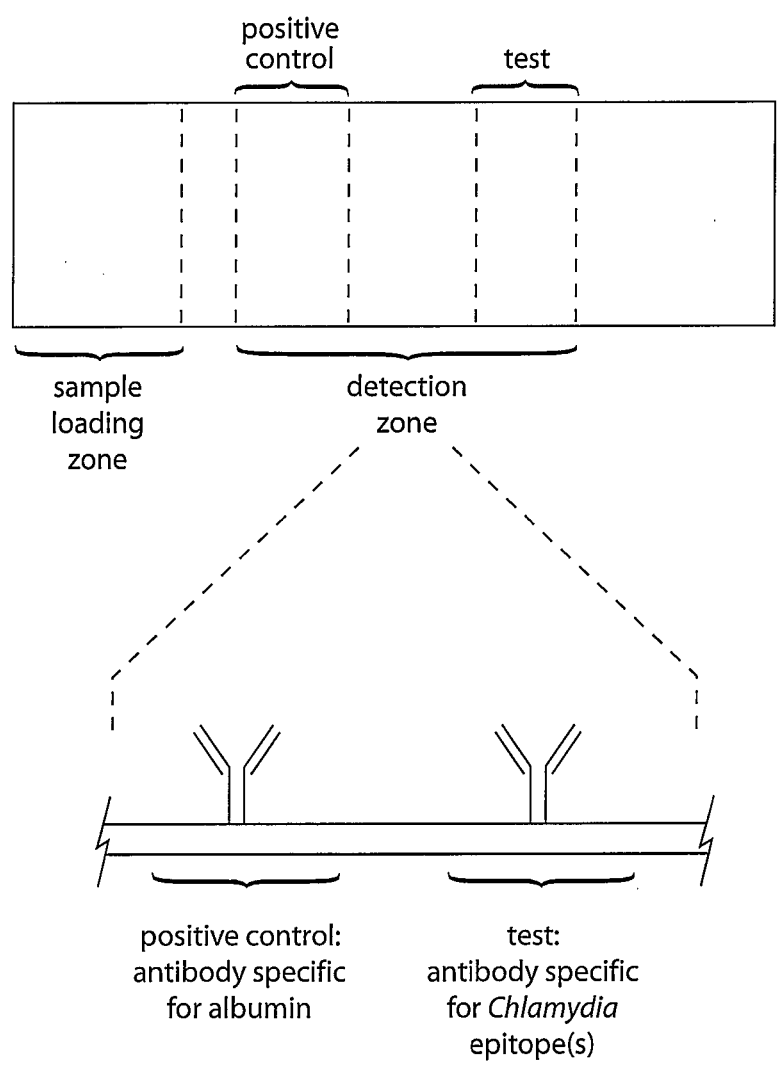

In another representative embodiment, depicted schematically in FIG. 11, the detection zone comprises a first detection zone (a "positive control zone" or "internal control zone") which has immobilized thereon an antibody specific for a "positive control" protein, e.g., a protein that would be expected to be present in the biological sample; and a second detection zone (a "test zone") that has immobilized thereon an antibody specific for one or more *Chlamydia* epitopes. Detection of the presence or absence of *Chlamydia* polypeptides in the biological sample is carried out by first adding the sample to the sample application region and allowing the sample to migrate by capillary action across the membrane strip. As the sample migrates across the membrane strip, the sample first migrates to the first detection zone, where it comes into contact with the immobilized antibody specific for the positive control protein. The sample then further migrates to the second detection zone where it comes into contact with immobilized *Chlamydia* epitope-specific antibody. The presence or absence of *Chlamydia* polypeptides bound to the immobilized *Chlamydia* epitope-specific antibody is then detected using a detectably labeled secondary binding molecule as described above. The secondary binding molecule is allowed to react with any captured *Chlamydia* polypeptide(s) (e.g., *Chlamydia* polypeptides bound to *Chlamydia* epitope-specific antibody immobilized on the membrane), and the presence of the secondary binding molecule detected using methods described above and well known in the art. The presence of the positive control protein is similarly detected using a secondary binding molecule that specifically binds to the positive control protein captured by the immobilized antibody specific for the positive control protein. The nature of the positive control protein will depend in part on the biological sample being assayed. Suitable positive control proteins include, but are not limited to, albumin, transferrin, IgG, and the like.

Suitable biological samples include, but are not limited to, a cervical swab, vaginal discharge, penile discharge, an anal swab, a conjunctival swab, and the like. A suitable biological sample includes any of the foregoing samples, manipulated in any way after their procurement, such as by treatment with reagents, solubilization, dilution with buffer, and the like.

Kits

Also provided are kits comprising a subject test device. A subject kit is useful for assaying a sample derived from a human subject for the presence or absence of a *Chlamydia* polypeptide. In addition to a subject device (e.g., a test strip having immobilized thereon an antibody specific for *Chlamydia* polypeptide(s)), a subject kit will in some embodiments comprise one or more of a wash buffer, a solution suitable for diluting a biological sample, a detection reagent, instructions for use of the kit, and the like.

In general, a solution suitable for diluting a biological sample will generally include a buffer, such as phosphate buffered saline (PBS), and may include additional components, such as for example, a non-specific blocking agent, such as bovine serum albumin (BSA), a detergent, e.g., a non-ionic detergent such as Triton-X-100, and the like.

The kits may further include one or more reagents that may be used in preparation of the patient-derived sample, such as heparin, Ficoll-Hypaque, lysing buffer, protease inhibitor, and the like, etc. In addition, the subject kits may further include one or more components employed in fractionation of the sample, such as an electrophoretic medium or precursors thereof, e.g. dried precursors of polyacrylamide gels, one or more buffer mediums or components thereof, and the like.

In certain embodiments, a subject kit further includes at least an information storage and presentation medium that contains reference data with which assay results may be compared in order to diagnose *Chlamydia* infection, i.e., reference data that that positively or negatively correlate to the presence of *Chlamydia* polypeptides. The information storage and presentation medium may be in any convenient form, such as printed information on a package insert, an electronic file present on an electronic storage medium, e.g. a magnetic disk, compact disc, and the like. In yet other embodiments, the kits may include alternative means for obtaining reference data, e.g. a website for obtaining the reference data "on-line."

In some embodiments, e.g., where the subject device is for private (e.g., in-home) use by a patient, a subject kit will include instructions to the patient for using the kit.

The kit components may be present in separate containers, or one or more of the components may be present in the same container, where the containers may be storage containers and/or containers that are employed during the assay for which the kit is designed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Rational Design of Antigenic Peptides

Materials and Methods
Source of *Chlamydia trachomatis* ompA DNA Sequences

Two different groups of ompA DNA sequences representing the 19 currently recognized reference serovars of *C. trachomatis* were used for the analyses in this study. The first group consisted of 121 strains with known serovar data derived from: 1) Genbank (n=22); 2) a published study comparing endometrial and cervical sequences (n=40) (Dean et al. (1995) *J. Infect. Dis.* 172:1013-1022); and 3) two unpublished studies from this laboratory, one comparing cervical and urethral sequences (n=39), and the other comparing sequences among sexual partners (n=20). For sources 2 and 3, urogenital specimens were obtained from consented individuals seen at family planning, adolescent, and STD clinics in the San Francisco Bay Area. Relevant clinical characteristics, GenBank accession numbers, and references for the 121 strains in the first group are presented in Table 1.

TABLE 1

*Chlamydia trachomatis* strains (n = 121) used in this study as the training set and as the test set.

| Serotype | Strain | Source | GenBank Accession No. Training Set | Date of Isolation | Reference |
|---|---|---|---|---|---|
| A | A/Har-13 | S1 | J03813 | 1958 | Baehr et al. 1988 |
| B | B/TW-5 | S1 | NA | 1959 | Dean&Millman 1997 |
| Ba | Ba/Apache | S1 | AF063194 | 1960 | Stothard, et al1998 |
| C | C/TW-3 | S1 | NA | 1959 | Dean&Millman 1997 |
| D | D/B120 | S1 | X62918 | 1983? | Sayada, & Elion1992 |
|   | D/IC-Cal-8 | S1 | X62920 | 1991? | Sayada, Elion 1992 |
|   | D/5EN | S2 | NA | 1991-4 | Dean et al. 1995 |
|   | D/32EN | S2 | NA | 1991-4 | Dean et al. 1995 |
|   | D/10EN | S2 | NA | 1991-4 | Dean et al. 1995 |
|   | D/ENC | S3 |  | 1993-4 | this study |
|   | D/RM2C | S3 |  | 1993-4 | this study |
|   | D/333C | S4 |  |  | this study |
|   | D/361C | S4 |  |  | this study |
|   | D/027C | S4 |  |  | this study |
|   | D/310C | S4 |  |  | this study |
| Da | Da/TW-448 | S1 | X62921 | 1985? | Sayada Elion 1992 |
| E | E/Bour | S1 | X52557 | 1959? | Peterson, delaMaza1990 |
|   | E/9EN | S2 | NA | 1991-4 | Dean et al. 1995 |
|   | E/13EN | S2 | NA | 1991-4 | Dean et al. 1995 |
|   | E/15EN | S2 | NA | 1991-4 | Dean et al. 1995 |
|   | E/16EN | S2 | NA | 1991-4 | Dean et al. 1995 |
|   | E/23EN | S2 | NA | 1991-4 | Dean et al. 1995 |
|   | E/14C | S2 | NA | 1991-4 | Dean et al. 1995 |
|   | E/22C | S2 | NA | 1991-4 | Dean et al. 1995 |
|   | E/24C | S2 | NA | 1991-4 | Dean et al. 1995 |
|   | E/33C | S2 | NA | 1991-4 | Dean et al. 1995 |
|   | E/25EN | S2 | NA | 1991-4 | Dean et al. 1995 |
|   | E/IBC | S3 |  | 1993-4 | this study |
|   | E/MCC | S3 |  | 1993-4 | this study |
|   | E/DCC | S3 |  | 1993-4 | this study |
|   | E/RCC | S3 |  | 1993-4 | this study |

TABLE 1-continued

*Chlamydia trachomatis* strains (n = 121) used in this study as the training set and as the test set.

| Serotype | Strain | Source | GenBank Accession No. Training Set | Date of Isolation | Reference |
|---|---|---|---|---|---|
| | E/DC2C | S3 | | 1993-4 | this study |
| | E/LHC | S3 | | 1993-4 | this study |
| | E/ALC | S3 | | 1993-4 | this study |
| | E/TLC | S3 | | 1993-4 | this study |
| | E/RMC | S3 | | 1993-4 | this study |
| | E/AMC | S3 | | 1993-4 | this study |
| | E/ATC | S3 | | 1993-4 | this study |
| | E/JWC | S3 | | 1993-4 | this study |
| | E/15C | S4 | | | this study |
| | E/235U | S4 | | | this study |
| | E/238U | S4 | | | this study |
| | E/240U | S4 | | | this study |
| F | F/IC-Cal3 | S1 | X52080 | 1960? | Zhang Caldwell 1990 |
| | F/17EN | S2 | NA | 1991-4 | Dean et al. 1995 |
| | F/20EN | S2 | NA | 1991-4 | Dean et al. 1995 |
| | F/20C | S2 | NA | 1991-4 | Dean et al. 1995 |
| | F/21C | S2 | NA | 1991-4 | Dean et al. 1995 |
| | F/28C | S2 | NA | 1991-4 | Dean et al. 1995 |
| | F/19C | S2 | NA | 1991-4 | Dean et al. 1995 |
| | F/13EN | S2 | NA | 1991-4 | Dean et al. 1995 |
| | F/7EN | S2 | NA | 1991-4 | Dean et al. 1995 |
| | F/12EN | S2 | NA | 1991-4 | Dean et al. 1995 |
| | F/2EN | S2 | NA | 1991-4 | Dean et al. 1995 |
| | F/8EN | S2 | NA | 1991-4 | Dean et al. 1995 |
| | F/MBC | S3 | | 1993-4 | this study |
| | F/RFC | S3 | | 1993-4 | this study |
| | F/SGC | S3 | | 1993-4 | this study |
| | F/KPC | S3 | | 1993-4 | this study |
| | F/RBC | S3 | | 1993-4 | this study |
| | F/MKC | S3 | | 1993-4 | this study |
| | F/NMC | S3 | | 1993-4 | this study |
| | F/CTC | S3 | | 1993-4 | this study |
| | F/205U | S4 | | | this study |
| | F/213U | S4 | | | this study |
| G | G/UW-57 | S1 | AF063199 | 1971 | Stothard, Jones 1998 |
| | G/GRC | S3 | | 1993-4 | this study |
| | G/279U | S4 | | | this study |
| H | H/UW-4 | S1 | NA | 1965 | Dean Millman 1997 |
| | H/28EN | S2 | NA | 1991-4 | Dean et al. 1995 |
| I | I/UW-12 | S1 | AF063200 | 1966 | Stothard, Jones 1998 |
| | I/3CX | S2 | NA | 1991-4 | Dean et al. 1995 |
| | I/4CX | S2 | NA | 1991-4 | Dean et al. 1995 |
| | I/LFC | S3 | | 1993-4 | this study |
| | I/LDC | S3 | | 1993-4 | this study |
| | I/CDC | S3 | | 1993-4 | this study |
| | I/CFC | S3 | | 1993-4 | this study |
| | I/063C | S4 | | | this study |
| | I/249U | S4 | | | this study |
| | I/216U | S4 | | | this study |
| Ia | Ia/IU-4168 | S1 | AF063201 | 1987 | Stothard, Jones 1998 |
| J | J/UW-36 | S1 | AF063202 | 1971 | Dean, Millman 1997 |
| | J/NCC | S3 | | 1993-4 | this study |
| | J/CRC | S3 | | 1993-4 | this study |
| | J/140535U | S4 | | | this study |
| Ja | Ja/IU-37538 | S1 | AF063203 | 1985 | Stothard, Jones 1998 |
| K | K/UW-31 | S1 | AF056204 | 1973 | Stothard, Jones 1998 |
| | K/30EN | S2 | NA | 1991-4 | Dean et al. 1995 |
| L1 | L1/440 | S1 | M36533 | 1968 | Pickett, Clarke 1987 |
| L2 | L2/434 | S1 | M14738 | 1968 | Stephens et al. 1986 |
| L2a | L2a/UW-396 | S1 | NA | 1985 | Dean, Millman 1997 |
| L3 | L3/404 | S1 | X55700 | 1967 | Fielder, de la Maza 1991 |
| A | A/Sa-1 | S1 | M58938 | 1957 | Hayes and Clarke 1990 |
| B | B/Jali20 | S1 | M33636 | 1985 | Herring et al. 1989 |
| D | D/AQC | S3 | | 1993-4 | this study |
| | D/31EN | S2 | NA | 1991-4 | Dean et al. 1995 |
| | D/067C | S4 | | | this study |
| | D/226U | S4 | | | this study |
| E | E/32EN | S2 | NA | 1991-4 | Dean et al. 1995 |
| | E/12CX | S2 | NA | 1991-4 | Dean et al. 1995 |
| | E/JAC | S3 | | 1993-4 | this study |
| | E/TBC | S3 | | 1993-4 | this study |
| | E/CBC | S3 | | 1993-4 | this study |

TABLE 1-continued

*Chlamydia trachomatis* strains (n = 121) used in this study as the training set and as the test set.

| Serotype | Strain | Source | GenBank Accession No. Training Set | Date of Isolation | Reference |
|---|---|---|---|---|---|
| | E/BOC | S3 | | 1993-4 | this study |
| | E/MSC | S3 | | 1993-4 | this study |
| F | F/21EN | S2 | NA | 1991-4 | Dean et al. 1995 |
| | F/18CX | S2 | NA | 1991-4 | Dean et al. 1995 |
| | F/1EN | S2 | NA | 1991-4 | Dean et al. 1995 |
| | F/6CX | S2 | NA | 1991-4 | Dean et al. 1995 |
| | F/JSC | S3 | | 1993-4 | this study |
| | F/TRC | S3 | | 1993-4 | this study |
| G | G/29CX | S2 | NA | 1991-4 | Dean et al. 1995 |
| H | H/11EN | S2 | NA | 1991-4 | Dean et al. 1995 |
| I | I/26EN | S2 | NA | 1991-4 | Dean et al. 1995 |
| | I/27EN | S2 | NA | 1991-4 | Dean et al. 1995 |
| | I/32EN | S2 | NA | 1991-4 | Dean et al. 1995 |
| | I/EMC | S3 | | 1993-4 | this study |
| J | J/LCC | S3 | | 1993-4 | this study |
| | J/417U | S4 | | | this study |
| K | K/208U | S4 | | | this study |
| | K/354C | S4 | | | this study |

Code for sources: S1 - GenBank; S2 - Study comparing cervical and endometrial genotypes; S3 - Study comparing cervical and urethral genotypes; S4 - Study comparing genotypes from sexual partners.
NOTE:
CX, cervix; EN, endometrium; U, urine.

The second group consisted of 507 strains with estimated serovar data derived from a recently published population based study in which ompA genotypes in the United States were evaluated (Millman et al. (2004) *J. Bacteriol.* 186:2457-2465).

ompA Genotyping ompA sequences for the patient populations from unpublished studies were generated using previously described techniques. Dean and Millman (1997) *J. Clin. Ivest.* 99:475-483; and Dean et al. (2000) *J. Infect. Dis.* 172:1013-1022. Briefly, pre-cultured cervical and urethral remnant samples were used for DNA extraction, polymerase chain reaction (PCR), and sequencing as previously described (Dean and Millman (1997) supra; and Dean et al. (2000) supra) except that different primer pairs were used to generate the PCR product and a high fidelity proof reading polymerase (Pfu-Turbo, Stratagene, La Jolla, Calif.) was used for each PCR. Approximately 500 µl of remnant sample was used for DNA purification. PCR was performed with primers that flank ompA (F200-5' TGAAAAAACTCTTGAAATCGGTATT 3' (SEQ ID NO:126)/MZ2-5' TACGGTACCTTA-GAAGCG-GAATTGTGCATTTAC 3' (SEQ ID NO:127)). Once the entire gene was amplified, nested and hemi-nested reactions were used to re-amplify the upstream and downstream halves of the gene. The primer pair MF100/VB3 was used to amplify the upstream half, as it flanks the start of the gene and VS3 (MF100-5' TGTAAAACGACGGCCAGTGCCGTATT-AGTGTTTGCCGC-TTTGAGT 3' (SEQ ID NO:128)/VB3-5'CATC-GTAGTCAATAGAGGCAT 3' (SEQ ID NO:129)). The pair MVF3/MZ2 was used to amplify the downstream half from VS3 through VS4 to the end of ompA (MVF3) (Dean and Millman (1997) supra. All samples were sequenced by big dye terminators and capillary automation using an ABI 377 (ABI) according to the manufacturer's instructions. Any sequence with ambiguous nucleotide data was verified by amplifying and sequencing DNA extracted a second time from the original sample using the same techniques as above.

Serovar Determination:

Cervical and urethral samples were propagated in McCoy cell monolayers in shell vials as previously described. Dean et al. (2001) *J. Infect. Dis.* 184:1632-1633. Briefly, isolates with ≧500 inclusions per vial were transferred to 96 well microtiter plates. Those with <500 inclusions were passaged until the threshold density was attained and then were transferred. Seventeen MAbs (Washington Research Foundation, Seattle, Wash.) were used to determine the serovar. The plates were read under fluorescent microscopy and the results were compared against prototype serovar reactivity patterns to identify the respective serovar.

Serovar was determined by reactivity to MAb for all strains except for the 507 clinical strains derived from a recently published population-based study. For these strains, serovar was estimated as previously described. Millman et al. (2004) *J. Bacteriol.* 186:2457-2465. Briefly, the similarity of the aligned clinical strain to each of the prototype serovar sequences was computed by dividing the number of like nucleotides by the total number of nucleotides under comparison. The estimate was the serovar of the prototype sequence with highest similarity to the clinical strain. In all analyses, positions with gaps were omitted.

Statistical Analyses:

Using supervised learning, a model was developed to predict the two response variables: serovar class and serovar. The 121 GenBank strains from the first group of sequences were randomly subdivided into a training set (92 sequences) and a test set (29 sequences). The training set was used to develop the model. Its accuracy was assessed by comparing predictions to known data for two test sets (29 from first group and 507 from the population-based group where serovar was estimated).

The model was developed by first identifying all variable ompA nucleotide positions that were perfectly correlated with the two response variables. The response variables had categories as follows: 1) Serovar class: a) B class; b) C class and c) Intermediate class; and 2) Serovar: a) A; b) B; c) Ba; d) C; e) D; f) Da; g) E; h) F; i) G; j) H; k) I; 1) Ia; m) J; n) Ja; o) K; p) L1; q) L2; r) L2a; and s) L3. The nucleotide positions that were correlated with the response variables were identified in the following manner. For each variable ompA position, an nx4 matrix was constructed with the n rows representing the categories of the response variable (B, C and I classes in this example) and the 4 columns representing the four nucleotide character states: A, C, G, and T. For each cell, the number of sequences with the corresponding nucleotide character state and the category of response variable were tabulated. Positions that differentiated a category from another or from multiple others were defined as having the following attribute: any non-zero cell(s) for that category and nucleotide character state would have a zero in the corresponding cell(s) for any or all categories under comparison. This algorithm is illustrated in Table 2.

TABLE 2

|         | A  | C  | G | T  |
|---------|----|----|---|----|
| B class | 0  | 0  | 0 | 44 |
| C class | 22 | 0  | 0 | 1  |
| I class | 0  | 25 | 0 | 0  |

A 3×4 matrix was constructed to test whether the variable ompA position was correlated with serovar class. For class I, there is only one non-zero nucleotide character state, C, and the corresponding cells for the B and C classes are zero. Thus, the criterion is satisfied for I compared to B and C. For class C, there are two non-zero character states, A and T. The criterion is satisfied for A but not for T. For class B, the criterion is not met for T. Thus, this position differentiates I from B and C; B from I; and C from I. It does not differentiate B from C and I; C from B and I; or B from C.

For each response variable, there were n−1 levels of differentiation analyzed. The first and highest level identified any nucleotide positions that differentiated one category from all other categories (all combinations of one category compared to n−1 categories). In the case of class, the highest level was composed of groups that differentiated B from C and I; I from C and B; and C from B and I. Each succeeding level identified positions that differentiated one category from all others minus 1, until the last level differentiated one category from just one other category. In the case of class, the second differentiation level was the final level as it differentiated all pairs: B from C; B from I; and C from I. Only the highest differentiation level at that position was reported, as lower differentiation levels were redundant.

After all variable ompA nucleotide positions perfectly correlated with the response variables were identified, the model was constructed so that the categories of the response variable were partitioned into a series of n−1 binary splits. First, the correlated nucleotide positions were classified into groups by their ability to differentiate the categories from one another in different ways as illustrated above. The group with the greatest number of correlated nucleotide positions and the highest differentiation level was chosen for the first partition. For example, if the group chosen differentiated I from B and C, the first partition would separate I from not I (B and C). For each arm of the partition (I and not I), a pattern was constructed of concatenated nucleotide character states for all sequences of that arm at that position, for all positions in the group. This procedure was continued for each succeeding binary split until all categories were partitioned.

The model was then used to predict the response variables for each of the two test sets. For each pattern, test-set nucleotide character states were compared to model nucleotide character states. The proportion of matched character states was compared in the two arms and the arm with the highest proportion was assigned. This was repeated until all partitions were assigned and the response variable was predicted. These predictions were compared to the known response variables and accuracy was estimated as the percent of correctly predicted response variables of those attempted. Finally, this algorithm was used to determine the most likely candidates for inclusion in a vaccine construct.

Results

For all the available sequences, 810 base pairs (bp) encompassing VS1 through VS4 (nt 244 to 1053) of the complete 1215 bp *C. trachomatis* ompA gene were aligned and analyzed. FIGS. 1A-T were generated to provide a comprehensive updated alignment of all 19 prototype serovar sequences from that of the 1989 alignment published by Yuan et al. ((1989) *Infect. Immun.* 57:1040-1049) the latter of which did not contain complete CR sequences. As illustrated for all prototype *C. trachomatis* sequences in FIGS. 1A-T, the locations of the aligned VSs as defined by Yuan et al. ((1989), supra) were as follows: VS1 from 256-324; VS2 from 490-567; VS3 from 757-798 and VS4 from 949-1053.

FIGS. 1A-1T.

Alignment of the ompA gene of *Chlamydia trachomatis* for the 19 prototype serovar sequences illustrating the nucleic acid numbering system used in this study. Nucleotide sequence of B/TW-5 shown on the top line as reference; periods represent conserved nucleotides; dashes represent gaps inserted to preserve the alignment. Nucleotide positions are shown as numbers above the sequence and are with respect to the ompA start site. Strains used as prototypes are as follows: B/TW-5; Ba/Apache; D/B120; Da/TW-448; E/Bour; L1/440; L2/434; L2a/UW-396; F/IC-Ca13; G/UW-57; C/TW-3; A/Har13; H/UW-4; I/UW-12; Ia/IU-4168; J/UW-36; Ja/IU-37538; K UW-31; L3/404.

Figure 2:
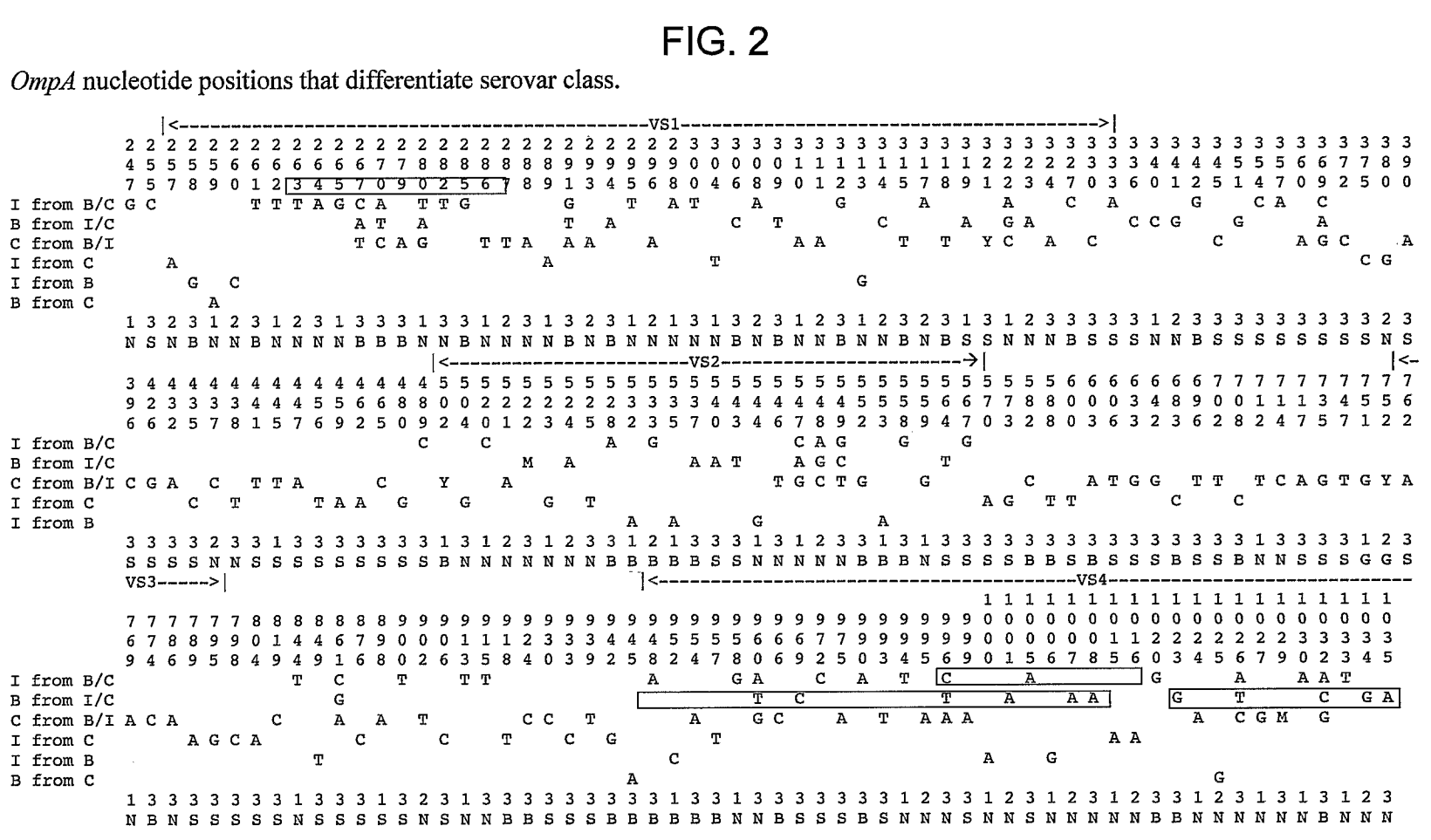

One hundred eighty five variable ompA positions that were perfectly correlated with serovar class were identified (FIG. 2). N: differentiating nucleotide encodes nonsynonymous changes only; S: Differentiating nucleotide encodes synonymous changes only; B: Differentiating nucleotide encodes both nonsynonymous and synonymous changes; G: Unable to evaluate changes due to presence of gap within codon. Nucleotide ambiguity code: C/T=Y; A/G=R; A/T=W; G/C=S; T/G=K; C/A=M; NOT C=D; NOT T=V; NOT G=H; NOT A=B.

Figure 3B:
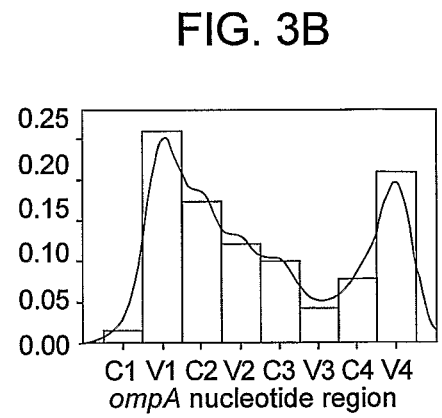
Figure 3C:
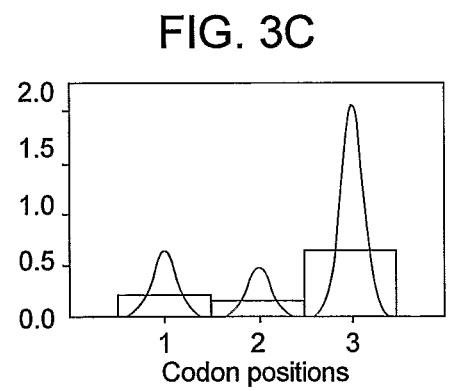
Figure 3D:
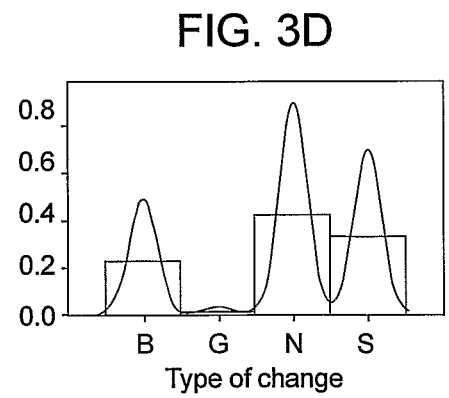

FIG. 3a shows the distribution of serovar class differentiation group by nucleotide position for the following groups: B class from I and C (B); I class from C and B (I); C class from B and I (C) and all classes from one another (A). FIGS. 3b-d show the density of correlated positions found as it varies by ompA region (FIG. 3b), by position within the codon (FIG. 3c), and by the type of nucleotide change produced (nonsynonymous vs. synonymous vs. both vs. gap; FIG. 3d). For serovar class, the group that differentiated C from B and I contained the greatest number of positions (n=77) followed by I from B and C (n=53); B from 1 and C (n=37) and all classes from one another (n=14). Interestingly, the group that differentiated C from B and I was composed of positions that were interspersed over the entire gene analyzed, while the other three differentiation groups had only two positions in C3 and no positions in V3 (FIG. 3a). Overall, the most informative regions that differentiated classes were V1 and V4 followed by C2, V2, C3, C4, V3 and C1 (FIG. 3b). Most correlated positions were in the third position of the codon (FIG. 3c). Positions with nonsynonymous changes were identified slightly more often than those with synonymous changes and occurred nearly twice as frequently as positions that had both types of changes (FIG. 3d).

Figure 4:
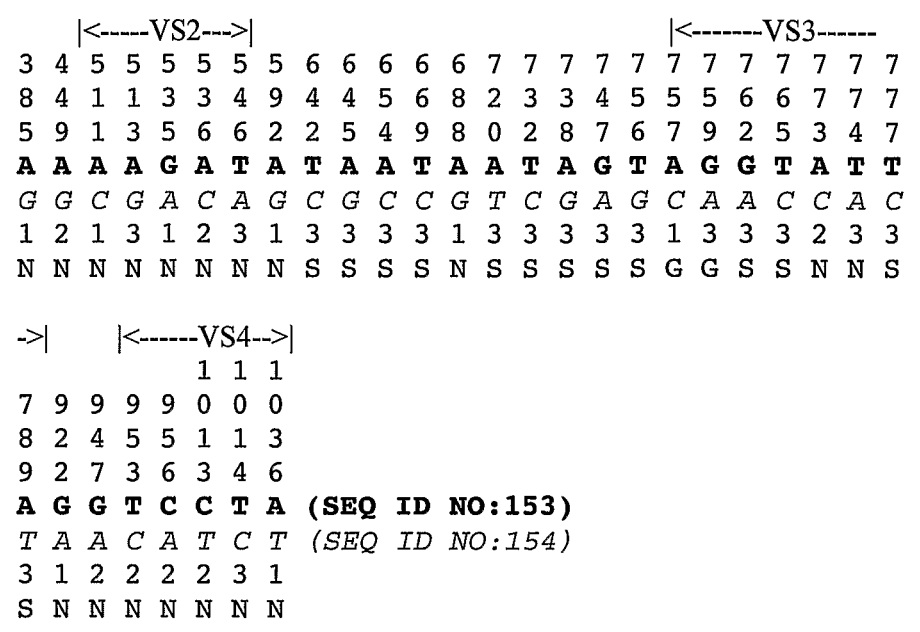

Within each of the three respective classes, 33 (Intermediate class; FIG. 4); 64 (B class; FIG. 5); and 74 (C class; FIGS. 6A and 6B) variable ompA positions differentiated the serovars.

Key to FIG. 4: nucleotides in bold type are nucleotides in F immunotype class sequences; nucleotides in italics are nucleotides in G immunotype class sequences; N: differentiating nucleotide encodes nonsynonymous changes only; S: Differentiating nucleotide encodes synonymous changes only; B: Differentiating nucleotide encodes both nonsynonymous and synonymous changes; G: Unable to evaluate changes due to presence of gap within codon. Nucleotide ambiguity code: C/T=Y; A/G=R; A/T=W; G/C=S; T/G K; C/A=M; NOT C=D; NOT T=V; NOT G=H; NOT A=B.

Figure 7:
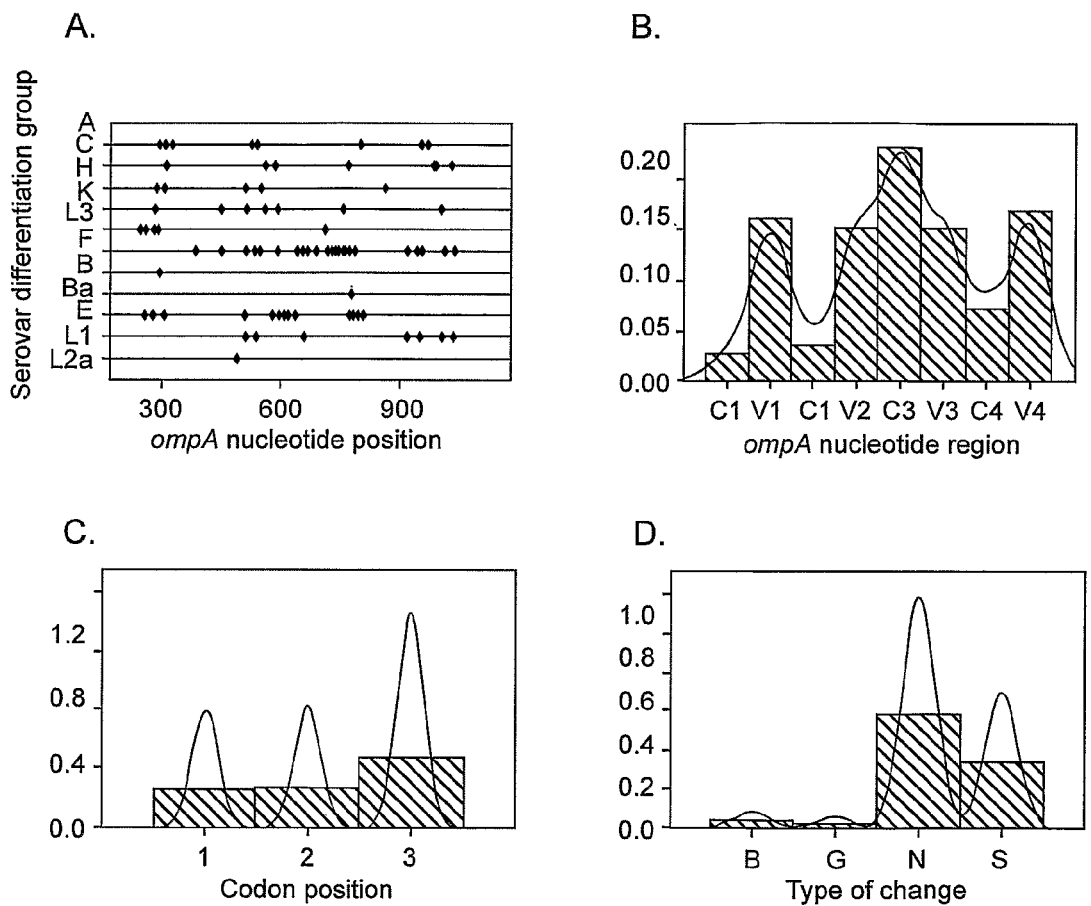

The distribution of serovar differentiation group by ompA nucleotide position, as well as the density of correlated positions identified as it varies by ompA region, by position within the codon, and by the type of nucleotide change produced are similarly shown in FIG. 7a-d. For serovars, the greatest number of correlated positions identified were able to differentiate F from G (33); E from others in the B class (26); A from others in the C class (12); C from others in the C class (11); L3 from others in the C class (9); K from others in the C class (7); L1 from others in the B class (7); H from others in the C class (5); and B, Ba and L2a from others (1;1;1 respectively) (FIG. 7a).

The distribution of information that differentiated serovar was quite different from that of class. While there was a relative paucity of positions within C3 and V3 for serovar class, these regions were very informative with respect to differentiation of serovar (FIG. 7b). The most informative regions for serovar were C3, V4, V1, V2 and V3 followed by C4, C2 and C1. As was seen for serovar class, most correlated positions found were observed in the third position of the codon (FIG. 7c). However, there was a greater proportion of second and first position codon differences represented for serovar than for serovar class. In contrast to that for serovar class, positions that produced nonsynonymous changes were found nearly twice as often as those that produced synonymous changes (FIG. 7d).

The ultimate goal was to construct four models that would predict serovar class and serovar from the genetic sequence data. Patterns of nucleotides were constructed from the concatenated positions that corresponded to the appropriate arm of the partition. The nucleotides of the two patterns on each arm of the binary split were compared to that of the sequence under analysis and assigned the category to which the proportion of matches was highest. This was continued until the category of the response variable was predicted. Using a model derived from 130 of the 185 possible positions available, each of the three classes were successfully partitioned (FIG. 8). The three models used to predict serovar within each class were composed of 33/33 (Intermediate class), 54/64 (B class) and 44/74 (C class) possible nucleotide positions. For each of the three models, serovar was successfully partitioned except for D, which could not be differentiated from Da within the B class (FIG. 9), and I, Ia, J and Ja could not be differentiated from each other within the C class (FIG. 10).

Using the model constructed from the concatenated positions, serovar class was correctly predicted 100% of the time for both test sets (29/29 for the first test set and 507/507 for the second larger population based test set). Serovar was correctly predicted 100% of the time for the Intermediate class serovars (7/7 and 119/119 for the respective test sets); 99.6% of the time for the B class serovars (12/12 and 226/227 for the respective test sets) and 99.4% of the time for the C class serovars (10/10 and 160/161 for the respective test sets). Within the B class, the only difficulty in predicting serovar was for a Ba/D recombinant in the population-based test set. This can be attributed to the fact that all positions that differentiated the B/Ba group from the D/Da group were at or downstream of nucleotide 477, which, curiously, was the putative cut-off point for this recombinant. In addition, downstream of nucleotide 477, this mosaic was most similar to serovar D. Within the C class, one erroneous assignment of a K strain to I/J was the only difficulty the model had in predicting serovar.

Finally, this model was used further to similarly predict nucleotide (and the encoded amino acid sequences) that would elicit a B cell (Table 3) and T cell responses (Table 4) for use as a vaccine construct.

TABLE 3

Proposed amino acid segments for use as vaccine constructs

| Amino Acid Sequence | Domain | Refs. | Designation |
|---|---|---|---|
| $^{231}$AGTEA$^{236}$A (SEQ ID NO:130) | VS3 | 42 | 3a |
| $^{231}$AGTDA$^{236}$A (SEQ ID NO:131) | VS3 | 42 | 3b |
| C$^{289}$AETIFDVTTLNPTIAGAGDVKTSAE$^{314}$GC (SEQ ID NO:132) | VS4 | 46, 47 | 4a |
| C$^{293}$AETILDVTLLNPTIAGKGTVVTSAE$^{309}$C (SEQ ID NO:43) | VS4 | 42 | 4b |
| C$^{298}$TTLNPTIAG$^{306}$C (SEQ ID NO:23) | VS4 | 47 | 4c |
| C$^{63}$GAKPTATTGNATAPSTLTAR$^{83}$EC (SEQ ID NO:48) | VS1 | 48, 49 | 1a |
| C$^{69}$TTSDVAGLQNDP$^{77}$C (SEQ ID NO:58) | VS1 | 45 | 1b |

Numbering of amino acids based on serovar A MOMP sequence homology; cysteine residues frame sequences introduced into the Ib position.

TABLE 4

T Helper Sequences

| T-cell Epitope Sequence | MOMP domain | Refs. |
|---|---|---|
| $^{214}$SEFTINKPKGYVGK$^{227}$E (SEQ ID NO:66) | Adjacent to VS3 | 50 |
| $^{17}$ILWEGFGGDPCDPCT$^{33}$T (SEQ ID NO:70) | N-terminal domain | 51 |
| $^{106}$ALNIWDRFD$^{116}$V (SEQ ID NO:71) | Between VS2 and VS3 | 51 |
| $^{331}$KMKSRKSCGIAVGTTVVSADKYAV$^{355}$T (SEQ ID NO:133) | C-terminal domain | 51 |

Amino acids numbering based upon serovar A MOMP sequence homology; cysteine residues replaced by serine residues to protect from unwanted disulfide coupling.

REFERENCES

1. Morrison R P, Su H, Lyng K and Yuan Y, 1990. The *Chlamydia trachomatis* hyp operon is homologous to the groE stress response operon of *Escherichia coli*. *Infect Immun* 58:2701-2705.
2. Allen J E, Locksley R M and Stephens R S, 1991. A single peptide from the major outer membrane protein of *Chlamydia trachomatis* elicits T cell help for the production of antibodies to protective determinants. *J. Immunol.* 147:674-679.
3. Su H, Morrison R P, Watkins N G and Caldwell H D, 1990. Identification and characterization of T helper cell epitopes of the major outer membrane protein of *Chlamydia trachomatis*. *J Exp Med* 172:203-212.
4. Peeling R W and Brunham R C, 1991. Neutralization of *Chlamydia trachomatis*: kinetics and stoichiometry. *Infect Immun* 59:2624-2630.
5. Baehr W, Zhang Y X, Joseph T, Su H, Nano F E, Everett K D and Caldwell H D, 1988. Mapping antigenic domains expressed by *Chlamydia trachomatis* major outer membrane protein genes. *Proc. Natl. Acad. Sci. USA* 85:4000-4004.
6. Batteiger B E, 1996. The major outer membrane protein of a single *Chlamydia trachomatis* serovar can possess more than one serovar-specific epitope. *Infect. Immun.* 64:542-547.
7. Batteiger B E, Lin P M, Jones R B and Van Der Pol B J, 1996. Species-, serogroup-, and serovar-specific epitopes are juxtaposed in variable sequence region 4 of the major outer membrane proteins of some *Chlamydia trachomatis* serovars. *Infect Immun* 64:2839-2841.
8. Zhang Y X, Stewart S, Joseph T, Taylor H R and Caldwell H D, 1987. Protective monoclonal antibodies recognize epitopes located on the major outer membrane protein of *Chlamydia trachomatis*. *J. Immunol.* 138:575-581.
9. Zhang Y X, Stewart S J and Caldwell H D, 1989. Protective monoclonal antibodies to *Chlamydia trachomatis* serovar- and serogroup-specific major outer membrane protein determinants. *Infect Immun* 57:636-638.
10. Stephens R S, Wagar E A and Schoolnik G K, 1988. High-resolution mapping of serovar-specific and common antigenic determinants of the major outer membrane protein for *Chlamydia trachomatis*. *J. Exp. Med.* 167:817-831.
11. Stagg A J, Elsley W A, Pickett M A, Ward M E and Knight S C, 1993. Primary human T-cell responses to the major outer membrane protein of *Chlamydia trachomatis*. *Immunology* 79:1-9.
12. Ortiz L, Angevine M, Kim S-K, Watkins D and DeMars R, 2000. T-cell epitopes in variable segments of *Chlamydia trachomatis* major outer membrane protein elicit serovar-specific immune responses in infected humans. *Infection and Immunity* 68:1719-1723.
13. Su H and Caldwell H D, 1992. Immunogenicity of a chimeric peptide corresponding to T helper and B cell epitopes of the *Chlamydia trachomatis* major outer membrane protein. *J Exp Med* 175:227-235.
14. Ishizaki M, Allen J E, Beatty P R and Stephens R S, 1992. Immune specificity of murine T-cell lines to the major outer membrane protein of *Chlamydia trachomatis*. *Infect Immun* 60:3714-3718.
15. Su H and Caldwell H D, 1993. Immunogenicity of a synthetic oligopeptide corresponding to antigenically common T-helper and B-cell neutralizing epitopes of the major outer membrane protein of *Chlamydia trachomatis*. *Vaccine* 11:1159-1166.
16. Hayes L J, Conlan J W, Everson J S, Ward M E and Clarke I N, 1991. *Chlamydia trachomatis* major outer membrane protein epitopes expressed as fusions with LamB in an attenuated aro A strain of *Salmonella typhimurium*; their application as potential immunogens. *J Gen Microbiol* 137:1557-1564.
17. Kim S K, Devine L, Angevine M, DeMars R and Kavathas P B, 2000. Direct detection and magnetic isolation of *Chlamydia trachomatis* major outer membrane protein-specific CD8+ CTLs with HLA class I tetramers. *J Immunol* 165:7285-7292.
18. Ortiz L, Demick K P, Petersen J W, Polka M, Rudersdorf R A, Van der Pol B, Jones R, Angevine M and DeMars R, 1996. *Chlamydia trachomatis* major outer membrane protein (MOMP) epitopes that activate HLA class II-restricted T cells from infected humans. *J Immunol* 157:4554-4567.
19. Kim S K, Angevine M, Demick K, Ortiz L, Rudersdorf R, Watkins D and DeMars R, 1999. Induction of HLA class I-restricted CD8+ CTLs specific for the major outer membrane protein of *Chlamydia trachomatis* in human genital tract infections. *J Immunol* 162:6855-6866.
20. Lampe M F, Kuehl L M, Wong K G and Stamm W E, 1994. *Chlamydia trachomatis* major outer membrane protein variants escape neutralization by polyclonal human immune sera. *Chlamydial Infections* 91-94.
21. Vretou E, Mentis A, Psarrou E, Tsoumaris L, Conidou G and Spiliopoulou D, 1992. Unusual prevalence of the rare serovar Da of *Chlamydia trachomatis* in Greece detected by monoclonal antibodies. *Sex Transm Dis* 19:78-83.
22. Batteiger B E, Newhall W Jt, Terho P, Wilde C E, 3rd and Jones R B, 1986. Antigenic analysis of the major outer membrane protein of *Chlamydia trachomatis* with murine monoclonal antibodies. *Infect Immun* 53:530-533.
23. Pal S, Cheng X, Peterson E M and de la Maza L M, 1993. Mapping of a surface-exposed B-cell epitope to the variable sequent 3 of the major outer-membrane protein of *Chlamydia trachomatis*. *J Gen Microbiol* 139:1565-1570.
24. Conlan J W, Clarke I N and Ward M E, 1988. Epitope mapping with solid-phase peptides: identification of type-, subspecies-, species- and genus-reactive antibody binding domains on the major outer membrane protein of *Chlamydia trachomatis*. *Mol. Microbiol.* 2:673-679.
25. Peterson E M, Cheng X, Markoff B A, Fielder T J and de la Maza L M, 1991. Functional and structural mapping of *Chlamydia trachomatis* species-specific major outer membrane protein epitopes by use of neutralizing monoclonal antibodies. *Infect Immun* 59:4147-4153.
26. Yang C L, Maclean I and Brunham R C, 1993. DNA sequence polymorphism of the *Chlamydia trachomatis* omp1 gene. *J Infect Dis* 168:1225-1230.
27. Brossay L, Villeneuve A, Paradis G, Cote L, Mourad W and Hebert J, 1994. Mimicry of a neutralizing epitope of the major outer membrane protein of *Chlamydia trachomatis* by anti-idiotypic antibodies. *Infect Immun* 62:341-347.
28. Newhall W Jt, Terho P, Wilde C E, 3rd, Batteiger B E and Jones R B, 1986. Serovar determination of *Chlamydia trachomatis* isolates by using type-specific monoclonal antibodies. *J Clin Microbiol* 23:333-338.
29. Dean D, 1994. Molecular characterization of new *Chlamydia trachomatis* serological variants from a trachoma endemic region of Africa. *Chlamydial Infectons* 259-262.
30. Dean D and Millman K, 1997. Molecular and mutation trends analyses of omp1 alleles for serovar E of *Chlamydia trachomatis*. Implications for the immunopathogenesis of disease. *J. Clin. Invest.* 99:475-483.
31. Lampe M F, Suchland R J and Stamm W E, 1993. Nucleotide sequence of the variable domains within the major outer membrane protein gene from serovariants of *Chlamydia trachomatis*. *Infect. Immun.* 61:213-219.
32. Wang S P and Grayston J T, 1991. Three new serovars of *Chlamydia trachomatis*: Da, Ia, and L2a. *J. Infect. Dis.* 163:403-405.
33. Dean D, Patton M and Stephens R S, 1991. Direct sequence evaluation of the major outer membrane protein gene variant regions of *Chlamydia trachomatis* subtypes D', I', and L2'. *Infect. Immun.* 59:1579-1582.
34. Qu Z, Cheng X, de la Maza L M and Peterson E M, 1993. Characterization of a neutralizing monoclonal antibody directed at variable domain I of the major outer membrane protein of *Chlamydia trachomatis* C-complex serovars. *Infect Immun* 61:1365-1370.
35. Caldwell H D, Wood H, Crane D, Bailey R, Jones R B, Mabey D, Maclean I, Mohammed Z, Peeling R, Roshick C, Schachter J, Solomon A W, Stamm W E, Suchland R J, Taylor L, West S K, Quinn T C, Belland R J and McClarty G, 2003. Polymorphisms in *Chlamydia trachomatis* tryptophan synthase genes differentiate between genital and ocular isolates. *J Clin Invest* 111:1757-1769.
36. Bavoil P M and Hsia R C, 1998. Type III secretion in *Chlamydia*: a case of deja vu? *Mol Microbiol* 28:860-862.
37. Grimwood J and Stephens R S, 1999. Computational analysis of the polymorphic membrane protein superfamily of *Chlamydia trachomatis* and *Chlamydia pneumoniae*. *Microb Comp Genomics* 4:187-201.
38. Dean D, Oudens E, Bolan G, Padian N and Schachter J, 1995. Major outer membrane protein variants of *Chlamydia trachomatis* are associated with severe upper genital tract infections and histopathology in San Francisco. *J. Infect. Dis.* 172:1013-1022.
39. Dean D, Suchland R and Stamm W, 2000. Evidence for long-term cervical persistence of *Chlamydia trachomatis* by omp1 genotyping. *J. Infect. Dis.* 182:909-916.
40. Dean D, Suchland R J and Stamm W E, 2001. Reply. *J Infect Dis* 184:1632-1633.
41. Yuan Y, Zhang Y X, Watkins N G and Caldwell H D, 1989. Nucleotide and deduced amino acid sequences for the four variable domains of the major outer membrane proteins of the 15 *Chlamydia trachomatis* serovars. *Infect. Immun.* 57:1040-1049.
42. Millman K L, Tavare S and Dean D, 2001. Recombination in the ompA gene but not the omcB gene of *Chlamydia* contributes to serovar-specific differences in tissue tropism, immune surveillance, and persistence of the organism. *J Bacteriol* 183:5997-6008.
43. Millman K, Black C M, Johnson R, Stamm W E, Jones R, Hook E, Martin D, Bolan G, Tavaré S, and Dean D, 2004. Population-based Genetic and Evolutionary Analysis of *Chlamydia trachomatis* Urogenital Strain Variation in the United States. *J Bacteriol* 186:2457-65
44. Sowa S, Sowa J, Collier L H and Blyth W A. 1969. Trachoma vaccine field trials in The Gambia. *J Hyg (Lond)* 67:699-717.
45. Igietseme J U and Murdin A. 2000. Induction of protective immunity against *Chlamydia trachomatis* genital infection by a vaccine based on major outer membrane protein-lipophilic immune response-stimulating complexes. Infection and Immunity 68:6798-6806.
46. Fitch W M, Peterson E M and de la Maza L M. 1993. Phylogenetic analysis of the outer-membrane-protein genes of Chlamydiae, and its implication for vaccine development. Mol Biol Evol 10:892-913.
47. Dean D and Powers V C. 2001. Persistent *Chlamydia trachomatis* infections resist apoptotic stimuli. Infect Immun 69:2442-7.
48. Su H and Caldwell H D. 1992. Immunogenicity of a chimeric peptide corresponding to T helper and B cell epitopes of the *Chlamydia trachomatis* major outer membrane protein. J Exp Med 175:227-35.
49. Murdin A D, Su H, Klein M H and Caldwell H D. 1995. Poliovirus hybrids expressing neutralization epitopes from variable domains I and IV of the major outer membrane protein of *Chlamydia trachomatis* elicit broadly cross-reactive *C. trachomatis*-neutralizing antibodies. Infect Immun 63:1116-21.

50. Stagg A J, Elsley W A, Pickett M A, Ward M E and Knight S C. 1993. Primary human T-cell responses to the major outer membrane protein of *Chlamydia trachomatis*. Immunology 79:1-9.

51. Su H, Morrison R P, Watkins N G and Caldwell H D. 1990. Identification and characterization of T helper cell epitopes of the major outer membrane protein of *Chlamydia trachomatis*. J Exp Med 172:203-12.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated macromolecule comprising:
a) a heterologous bacterial protein; and
b) a polypeptide consisting of a sequence selected from:

```
                                     (SEQ ID NO: 132)
CAETIFDVTTLNPTIAGAGDVKTSAEGC;

(SEQ ID NO: 43)
CAETILDVTTLNPTIAGKGTVVTSAEC;

(SEQ ID NO: 23)
CTTLNPTIAGC;

(SEQ ID NO: 25)
CAETIFDVTTLNPTIAGC;

(SEQ ID NO: 26)
AETIFDVTTLNPTIAGAGCVKTSAEG;

(SEQ ID NO: 27)
CAETIFDVTTLNPTIAGAGCVKTSAEGC;

(SEQ ID NO: 28)
AETILDVTTLNPTIAG;

(SEQ ID NO: 29)
CAETILDVTTLNPTIAGC;

(SEQ ID NO: 30)
TTLNPTIAGAGCVKTSAEG;

(SEQ ID NO: 31)
CTTLNPTIAGAGCVKTSAEGC;

(SEQ ID NO: 32)
TTLNPTIAGAGDVKTSAE;

(SEQ ID NO: 33)
CTTLNPTIAGAGDVKTSAEC;

(SEQ ID NO: 34)
TTLNPTIAGKGTVVTSAE;

(SEQ ID NO: 35)
CTTLNPTIAGKGTVVTSAEC;

(SEQ ID NO: 36)
TTLNPTIAGKGTVVSSAE;

(SEQ ID NO: 37)
CTTLNPTIAGKGTVVSSAEC;

(SEQ ID NO: 38)
TTLNPTIAGKGTVVASSAE;

(SEQ ID NO: 39)
CTTLNPTIAGKGTVVASSAEC;

(SEQ ID NO: 40)
TTLNPTTLNPTIAGKGTVVASSAE;
and
                                      (SEQ ID NO: 42)
AETILDVTTLNPTIAGKGTVVTSAE.
```

2. An immunogenic composition comprising:
a) a macromolecule of claim 1; and
b) an adjuvant.

3. An isolated polypeptide consisting of a sequence selected from:

```
                                     (SEQ ID NO: 132)
CAETIFDVTTLNPTIAGAGDVKTSAEGC;

(SEQ ID NO: 43)
CAETILDVTTLNPTIAGKGTVVTSAEC;

(SEQ ID NO: 23)
CTTLNPTIAGC;

(SEQ ID NO: 25)
CAETIFDVTTLNPTIAGC;

(SEQ ID NO: 26)
AETIFDVTTLNPTIAGAGCVKTSAEG;

(SEQ ID NO: 27)
CAETIFDVTTLNPTIAGAGCVKTSAEGC;

(SEQ ID NO: 28)
AETILDVTTLNPTIAG;

(SEQ ID NO: 29)
CAETILDVTTLNPTIAGC;

(SEQ ID NO: 30)
TTLNPTIAGAGCVKTSAEG;

(SEQ ID NO: 31)
CTTLNPTIAGAGCVKTSAEGC;

(SEQ ID NO: 32)
TTLNPTIAGAGDVKTSAE;

(SEQ ID NO: 33)
CTTLNPTIAGAGDVKTSAEC;

(SEQ ID NO: 34)
TTLNPTIAGKGTVVTSAE;

(SEQ ID NO: 35)
CTTLNPTIAGKGTVVTSAEC;

(SEQ ID NO: 36)
TTLNPTIAGKGTVVSSAE;

(SEQ ID NO: 37)
CTTLNPTIAGKGTVVSSAEC;

(SEQ ID NO: 38)
TTLNPTIAGKGTVVASSAE;

(SEQ ID NO: 39)
CTTLNPTIAGKGTVVASSAEC;

(SEQ ID NO: 40)
TTLNPTTLNPTIAGKGTVVASSAE;
and
                                      (SEQ ID NO: 42)
AETILDVTTLNPTIAGKGTVVTSAE.
```

4. A composition comprising a polypeptide according to claim 3.

5. An immunogenic composition comprising a polypeptide according to claim 3.

6. An immunogenic composition comprising two or more different polypeptides, wherein each of the polypeptides consists of a sequence selected from:

```
                                     (SEQ ID NO: 132)
CAETIFDVTTLNPTIAGAGDVKTSAEGC;

(SEQ ID NO: 43)
CAETILDVTTLNPTIAGKGTVVTSAEC;

(SEQ ID NO: 23)
CTTLNPTIAGC;

(SEQ ID NO: 25)
CAETIFDVTTLNPTIAGC;

(SEQ ID NO: 26)
AETIFDVTTLNPTIAGAGCVKTSAEG;
```

-continued

```
                                  (SEQ ID NO: 27)
CAETIFDVTTLNPTIAGAGCVKTSAEGC;

(SEQ ID NO: 28)
AETILDVTTLNPTIAG;

(SEQ ID NO: 29)
CAETILDVTTLNPTIAGC;

(SEQ ID NO: 30)
TTLNPTIAGAGCVKTSAEG;

(SEQ ID NO: 31)
CTTLNPTIAGAGCVKTSAEGC;

(SEQ ID NO: 32)
TTLNPTIAGAGDVKTSAE;

(SEQ ID NO: 33)
CTTLNPTIAGAGDVKTSAEC;

(SEQ ID NO: 34)
TTLNPTIAGKGTVVTSAE;
```

-continued

```
                                  (SEQ ID NO: 35)
CTTLNPTIAGKGTVVTSAEC;

(SEQ ID NO: 36)
TTLNPTIAGKGTVVSSAE;

(SEQ ID NO: 37)
CTTLNPTIAGKGTVVSSAEC;

(SEQ ID NO: 38)
TTLNPTIAGKGTVVASSAE;

(SEQ ID NO: 39)
CTTLNPTIAGKGTVVASSAEC;

(SEQ ID NO: 40)
TTLNPTTLNPTIAGKGTVVASSAE;
and (SEQ ID NO: 42)
AETILDVTTLNPTIAGKGTVVTSAE.
```

\* \* \* \* \*

UNITED STATES PATENT AND TRADEMARK OFFICE
CERTIFICATE OF CORRECTION

PATENT NO. : 8,486,411 B2  
APPLICATION NO. : 12/064327  
DATED : July 16, 2013  
INVENTOR(S) : Deborah Dean Page 1 of 1

It is certified that error appears in the above-identified patent and that said Letters Patent is hereby corrected as shown below:

In the Specification

In column 1, lines 17-19, please replace "The U.S. government has certain rights in this invention, pursuant to grant nos. AI39499 and EY/AI12219 awarded by the National Institutes of Health" with --This invention was made with government support under grant no. AI39499 awarded by the National Institute of Health; and with government support under grant no. EY/AI12219 awarded by the National Institute of Health. The government has certain rights in the invention--.

Signed and Sealed this  
Twenty-ninth Day of April, 2014

Michelle K. Lee  
*Deputy Director of the United States Patent and Trademark Office*